(12) United States Patent
Chappuis et al.

(10) Patent No.: US 10,864,057 B2
(45) Date of Patent: Dec. 15, 2020

(54) UNIVERSAL INSTRUMENT GUIDE FOR ROBOTIC SURGICAL SYSTEMS, SURGICAL INSTRUMENT SYSTEMS, AND METHODS OF THEIR USE

(71) Applicant: KB MEDICAL, SA, Audubon, PA (US)

(72) Inventors: Olivier Chappuis, Lutry (CH); Szymon Kostrzewski, Lausanne (CH)

(73) Assignee: KB Medical, SA, Audubon, PA (US)

( * ) Notice: Subject to any disclaimer, the term of this patent is extended or adjusted under 35 U.S.C. 154(b) by 241 days.

(21) Appl. No.: 15/874,365

(22) Filed: Jan. 18, 2018

(65) Prior Publication Data

US 2018/0200016 A1 Jul. 19, 2018

Related U.S. Application Data

(60) Provisional application No. 62/447,712, filed on Jan. 18, 2017.

(51) Int. Cl.
*A61B 90/11* (2016.01)
*A61B 17/17* (2006.01)
(Continued)

(52) U.S. Cl.
CPC .......... *A61B 90/11* (2016.02); *A61B 17/1757* (2013.01); *A61B 34/30* (2016.02); *A61B 34/70* (2016.02); *A61B 17/1655* (2013.01); *A61B 17/1671* (2013.01); *A61B 17/1703* (2013.01); *A61B 2017/00464* (2013.01); *A61B 2017/00477* (2013.01); *A61B 2017/347* (2013.01); *A61B 2034/2055* (2016.02); *A61B 2034/303* (2016.02); *A61B 2090/103* (2016.02);
(Continued)

(58) Field of Classification Search
CPC ...................................................... A61B 90/11
See application file for complete search history.

(56) References Cited

U.S. PATENT DOCUMENTS

| 4,150,293 A | 4/1979 | Franke |
| 5,246,010 A | 9/1993 | Gazzara et al. |

(Continued)

FOREIGN PATENT DOCUMENTS

| EP | 1871267 A1 | 1/2008 |
| WO | 2006091494 A1 | 8/2006 |

*Primary Examiner* — Olivia C Chang

(57) ABSTRACT

Described herein are systems and apparatus of surgical instruments engineered for integration with robotic surgical systems to enhance precision in surgical procedures. Also described herein are methods of using such surgical instruments in performing surgical procedures. The use of such surgical instruments reduce complications arising from misalignment during surgery. The disclosed technology assists in stages of a surgical procedure that require a precise trajectory to be followed. Surgical instrument guides are attached to a universal surgical instrument guide, which is engineered to attach directly or indirectly with a robotic arm of a robotic surgical system. Surgical instruments can then be precisely guided along an axis defined by the universal surgical instrument guide. Individual instruments are easily inserted and removed from the channel of the universal surgical instrument guide, thus allowing a range of instruments to be used throughout a procedure while maintaining the surgical trajectory.

14 Claims, 38 Drawing Sheets

(51) Int. Cl.
  *A61B 34/30* (2016.01)
  *A61B 34/00* (2016.01)
  *A61B 17/16* (2006.01)
  *A61M 29/00* (2006.01)
  *A61B 17/00* (2006.01)
  *A61B 34/20* (2016.01)
  *A61B 90/00* (2016.01)
  *A61B 90/10* (2016.01)
  *A61B 17/34* (2006.01)

(52) U.S. Cl.
  CPC . *A61B 2090/373* (2016.02); *A61B 2090/3937* (2016.02); *A61B 2090/3983* (2016.02); *A61M 29/00* (2013.01)

(56) References Cited

U.S. PATENT DOCUMENTS

| | | | |
|---|---|---|---|
| 5,598,453 | A | 1/1997 | Baba et al. |
| 5,772,594 | A | 6/1998 | Barrick |
| 5,987,960 | A | 11/1999 | Messner et al. |
| 6,031,888 | A | 2/2000 | Ivan et al. |
| 6,144,875 | A | 11/2000 | Schweikard et al. |
| 6,203,196 | B1 | 3/2001 | Meyer et al. |
| 6,306,126 | B1 | 10/2001 | Montezuma |
| 6,314,311 | B1 | 11/2001 | Williams et al. |
| 6,320,929 | B1 | 11/2001 | Von Der Haar |
| 6,477,400 | B1 | 11/2002 | Barrick |
| 6,484,049 | B1 | 11/2002 | Seeley et al. |
| 6,487,267 | B1 | 11/2002 | Wolter |
| 6,490,475 | B1 | 12/2002 | Seeley et al. |
| 6,501,981 | B1 | 12/2002 | Schweikard et al. |
| 6,535,756 | B1 | 3/2003 | Simon et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,666,579 | B2 | 12/2003 | Jensen |
| 6,757,068 | B2 | 6/2004 | Foxlin |
| 6,782,287 | B2 | 8/2004 | Grzeszczuk et al. |
| 6,856,826 | B2 | 2/2005 | Seeley et al. |
| 6,856,827 | B2 | 2/2005 | Seeley et al. |
| 6,920,347 | B2 | 7/2005 | Simon et al. |
| 6,922,632 | B2 | 7/2005 | Foxlin |
| 6,988,009 | B2 | 1/2006 | Grimm et al. |
| 6,996,487 | B2 | 2/2006 | Jutras et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,301,648 | B2 | 11/2007 | Foxlin |
| 7,313,430 | B2 | 12/2007 | Urquhart et al. |
| 7,318,805 | B2 | 1/2008 | Schweikard et al. |
| 7,324,623 | B2 | 1/2008 | Heuscher et al. |
| 7,327,865 | B2 | 2/2008 | Fu et al. |
| 7,460,637 | B2 | 12/2008 | Clinthorne et al. |
| 7,493,153 | B2 | 2/2009 | Ahmed et al. |
| 7,505,617 | B2 | 3/2009 | Fu et al. |
| 7,623,902 | B2 | 11/2009 | Pacheco |
| 7,643,862 | B2 | 1/2010 | Schoenefeld |
| 7,661,881 | B2 | 2/2010 | Gregerson et al. |
| 7,683,331 | B2 | 3/2010 | Chang |
| 7,683,332 | B2 | 3/2010 | Chang |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,725,253 | B2 | 5/2010 | Foxlin |
| 7,726,171 | B2 | 6/2010 | Langlotz et al. |
| 7,760,849 | B2 | 7/2010 | Zhang |
| 7,796,728 | B2 | 9/2010 | Bergfjord |
| 7,813,838 | B2 | 10/2010 | Sommer |
| 7,835,778 | B2 | 11/2010 | Foley et al. |
| 7,835,784 | B2 | 11/2010 | Mire et al. |
| 7,840,256 | B2 | 11/2010 | Lakin et al. |
| 7,844,320 | B2 | 11/2010 | Shahidi |
| 7,853,305 | B2 | 12/2010 | Simon et al. |
| 7,853,313 | B2 | 12/2010 | Thompson |
| 7,900,524 | B2 | 3/2011 | Calloway et al. |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 8,019,045 | B2 | 9/2011 | Kato |
| 8,021,310 | B2 | 9/2011 | Sanborn et al. |
| 8,052,688 | B2 | 11/2011 | Wolf, II |
| 8,086,299 | B2 | 12/2011 | Adler et al. |
| 8,098,914 | B2 | 1/2012 | Liao et al. |
| 8,100,950 | B2 | 1/2012 | St Clair et al. |
| 8,116,430 | B1 | 2/2012 | Shapiro et al. |
| 8,121,249 | B2 | 2/2012 | Wang et al. |
| 8,150,494 | B2 | 4/2012 | Simon et al. |
| 8,208,708 | B2 | 6/2012 | Homan et al. |
| 8,224,024 | B2 | 7/2012 | Foxlin |
| 8,311,611 | B2 | 11/2012 | Csavoy et al. |
| 8,335,557 | B2 | 12/2012 | Maschke |
| 8,358,818 | B2 | 1/2013 | Miga et al. |
| 8,379,791 | B2 | 2/2013 | Forthmann et al. |
| 8,386,019 | B2 | 2/2013 | Camus et al. |
| 8,394,099 | B2 | 3/2013 | Patwardhan |
| 3,462,911 | A1 | 6/2013 | Vesel et al. |
| 8,526,700 | B2 | 9/2013 | Isaacs |
| 8,541,970 | B2 | 9/2013 | Nowlin et al. |
| 8,560,118 | B2 | 10/2013 | Green et al. |
| 8,597,198 | B2 | 12/2013 | Sanborn et al. |
| 8,611,985 | B2 | 12/2013 | Lavallee et al. |
| 8,630,389 | B2 | 1/2014 | Kato |
| 8,634,897 | B2 | 1/2014 | Simon et al. |
| 8,660,635 | B2 | 2/2014 | Simon et al. |
| 8,678,647 | B2 | 3/2014 | Gregerson et al. |
| 8,696,458 | B2 | 4/2014 | Foxlin et al. |
| 8,706,185 | B2 | 4/2014 | Foley et al. |
| 8,727,618 | B2 | 5/2014 | Maschke et al. |
| 8,738,115 | B2 | 5/2014 | Amberg et al. |
| 8,740,882 | B2 | 6/2014 | Jun et al. |
| 8,781,186 | B2 | 7/2014 | Clements et al. |
| 8,781,630 | B2 | 7/2014 | Banks et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,812,077 | B2 | 8/2014 | Dempsey |
| 8,814,793 | B2 | 8/2014 | Brabrand |
| 8,818,105 | B2 | 8/2014 | Myronenko et al. |
| 8,821,511 | B2 | 9/2014 | Von Jako et al. |
| 8,867,703 | B2 | 10/2014 | Shapiro et al. |
| 8,888,821 | B2 | 11/2014 | Rezach et al. |
| 8,964,934 | B2 | 2/2015 | Ein-Gal |
| 8,992,580 | B2 | 3/2015 | Bar et al. |
| 8,996,169 | B2 | 3/2015 | Lightcap et al. |
| 9,001,963 | B2 | 4/2015 | Sowards-Emmerd et al. |
| 9,002,076 | B2 | 4/2015 | Khadem et al. |
| 9,044,190 | B2 | 6/2015 | Rubner et al. |
| 9,107,683 | B2 | 8/2015 | Hourtash et al. |
| 9,125,556 | B2 | 9/2015 | Zehavi et al. |
| 9,131,986 | B2 | 9/2015 | Greer et al. |
| 9,215,968 | B2 | 12/2015 | Schostek et al. |
| 9,308,050 | B2 | 4/2016 | Kostrzewski et al. |
| 9,380,984 | B2 | 7/2016 | Li et al. |
| 9,393,039 | B2 | 7/2016 | Lechner et al. |
| 9,398,886 | B2 | 7/2016 | Gregerson et al. |
| 9,398,890 | B2 | 7/2016 | Dong et al. |
| 9,414,859 | B2 | 8/2016 | Ballard et al. |
| 9,420,975 | B2 | 8/2016 | Gutfleisch et al. |
| 9,492,235 | B2 | 11/2016 | Hourtash et al. |
| 9,592,096 | B2 | 3/2017 | Maillet et al. |
| 9,750,465 | B2 | 9/2017 | Engel et al. |
| 9,757,203 | B2 | 9/2017 | Hourtash et al. |
| 9,795,354 | B2 | 10/2017 | Menegaz et al. |

(56) References Cited

U.S. PATENT DOCUMENTS

| | | |
|---|---|---|
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2004/0076259 A1 | 4/2004 | Jensen et al. |
| 2006/0184396 A1 | 8/2006 | Dennis et al. |
| 2006/0291612 A1 | 12/2006 | Nishide et al. |
| 2007/0038059 A1 | 2/2007 | Sheffer et al. |
| 2007/0073133 A1 | 3/2007 | Schoenefeld |
| 2008/0004523 A1 | 1/2008 | Jensen |
| 2008/0013809 A1 | 1/2008 | Zhu et al. |
| 2008/0082109 A1 | 4/2008 | Moll et al. |
| 2008/0108991 A1 | 5/2008 | Von Jako |
| 2008/0144906 A1 | 6/2008 | Allred et al. |
| 2008/0161680 A1 | 7/2008 | Von Jako et al. |
| 2008/0235052 A1 | 9/2008 | Node-Langlois et al. |
| 2008/0269596 A1 | 10/2008 | Revie et al. |
| 2008/0287781 A1 | 11/2008 | Revie et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0185655 A1 | 7/2009 | Koken et al. |
| 2009/0198121 A1 | 8/2009 | Hoheisel |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0228117 A1 | 9/2010 | Hartmann |
| 2010/0274120 A1 | 10/2010 | Heuscher |
| 2011/0098553 A1 | 4/2011 | Robbins et al. |
| 2011/0282189 A1 | 11/2011 | Graumann |
| 2011/0286573 A1 | 11/2011 | Schretter et al. |
| 2012/0035507 A1 | 2/2012 | George et al. |
| 2012/0051498 A1 | 3/2012 | Koishi |
| 2012/0143084 A1 | 6/2012 | Shoham |
| 2012/0226145 A1 | 9/2012 | Chang et al. |
| 2012/0235909 A1 | 9/2012 | Birkenbach et al. |
| 2012/0294498 A1 | 11/2012 | Popovic |
| 2013/0016889 A1 | 1/2013 | Myronenko et al. |
| 2013/0060146 A1 | 3/2013 | Yang et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0281821 A1 | 10/2013 | Liu et al. |
| 2013/0282022 A1* | 10/2013 | Yousef .................. A61B 34/71 606/130 |
| 2013/0307955 A1 | 11/2013 | Deitz et al. |
| 2013/0342578 A1 | 12/2013 | Isaacs |
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0080086 A1 | 3/2014 | Chen |
| 2014/0081281 A1 | 3/2014 | Felder |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0196365 A1 | 7/2015 | Kostrzewski et al. |
| 2015/0213633 A1 | 7/2015 | Chang et al. |
| 2015/0305817 A1 | 10/2015 | Kostrzewski |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0256225 A1 | 9/2016 | Crawford et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

* cited by examiner

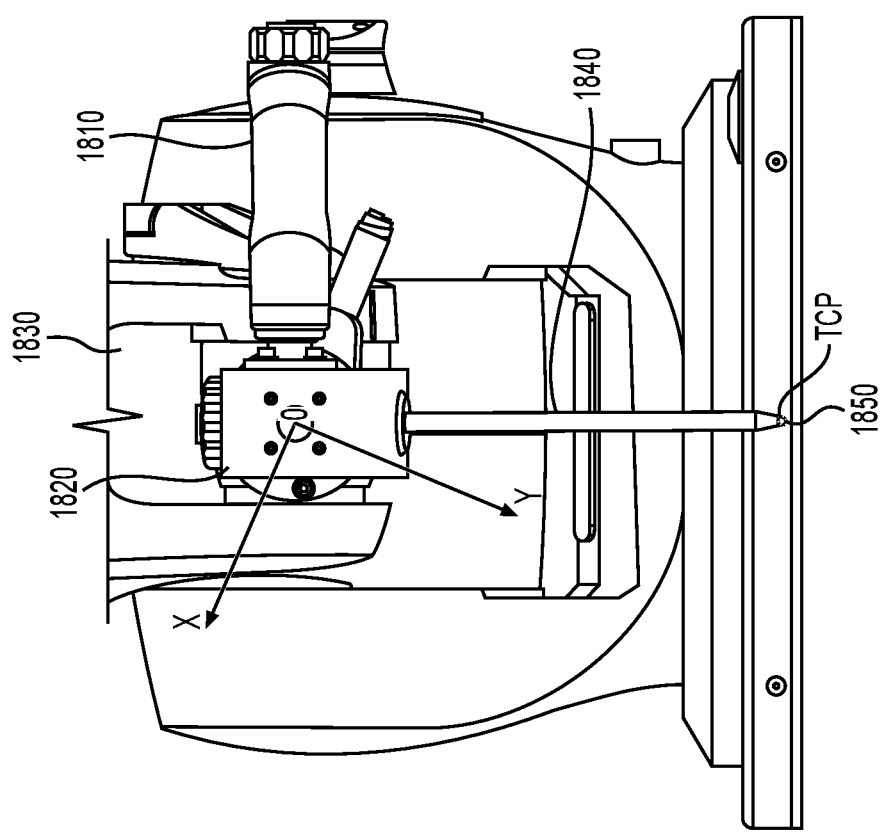
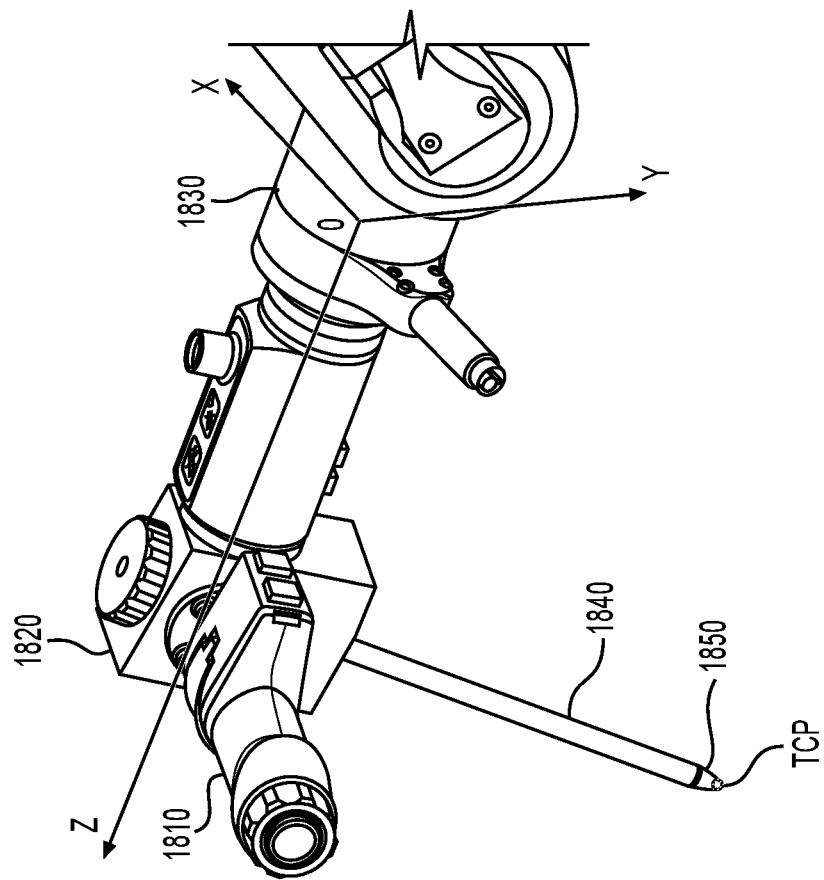
FIG. 18B
FIG. 18A

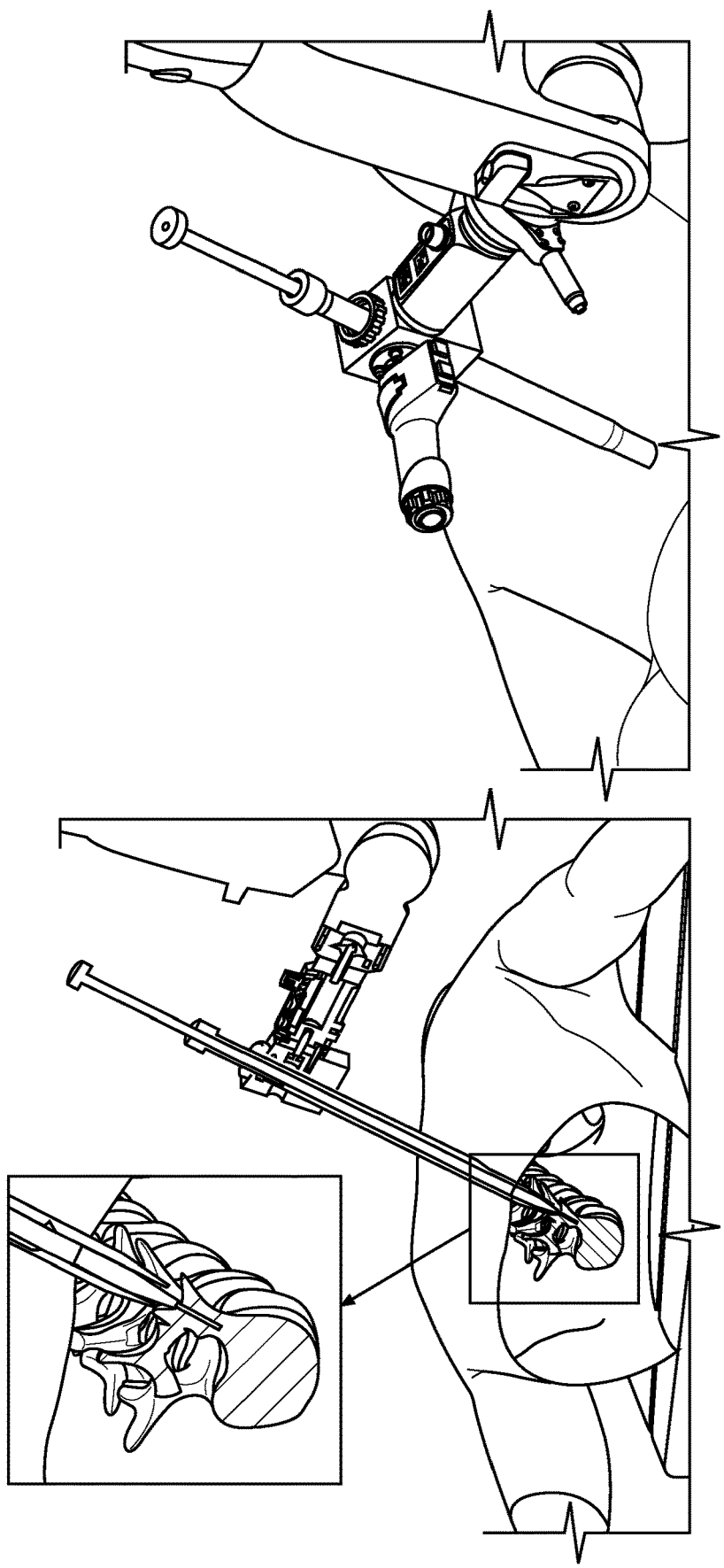

UNIVERSAL INSTRUMENT GUIDE FOR ROBOTIC SURGICAL SYSTEMS, SURGICAL INSTRUMENT SYSTEMS, AND METHODS OF THEIR USE

FIELD OF INVENTION

This invention relates generally to a universal instrument guide for use, with a robotic surgical system, in guiding surgical instruments, surgical instrument systems for use with a universal instrument guide, and methods of their use.

BACKGROUND

Surgical procedures on the spine are generally complex procedures involving many steps. When placing a pedicle screw in the vertebra, in addition to the drilling stage, the tapping and screw placement (using screwdriver) stages are important for the success of the surgery. For example, in certain types of patients (e.g., having osteoporosis), even in the case when the hole in the vertebra is precisely made, the bone is not strong enough to guide other instruments and implants without additional guidance from surgical instruments. This creates a hazardous situation when surgeon assumes that he/she is guided by the drilled hole while in reality the surgeon is placing instruments in other places (e.g., spinal canal) that can cause serious damages to the patient.

Robotic systems which provides assistance during only the drilling stage of a procedure have another potential disadvantage. In a clinical situation, the surface of a vertebra is covered by a multitude of soft tissues. Even in open surgeries, when the surgeon has wide access to the spine, it is difficult to find the hole after it is drilled because tissue often covers the entry point. In case of percutaneous surgeries, it is almost impossible due to lack of direct vision.

In order to overcome this difficulty, surgeons use a long wire, called a "k-wire," which they place inside the drilled hole to mark it for later use. K-wires are used in a range of orthopedic surgeries. When drilling and placing a screw in a bone, surgeons use cannulated instruments (e.g., taps, screwdrivers) and implants (e.g., screws) so that all of them follow the wire such that they properly enter the drilled hole.

K-wires, even though widely used, have certain disadvantages. There is a risk that the k-wire advances with the guided instrument without the surgeon realizing it. In certain cases, the k-wire can even go out of a bone on the opposite side and hurt important tissues (e.g., aorta in front of the lumbar spine). In some cases, when the instrument advances along a different axis than the k-wire inside bone, the wire might bend and break or block the instrument inside the bone creating a very difficult problem to resolve. There are known cases in which the k-wire came loose and out of the bone without the surgeon realizing it. The surgeon followed this loose k-wire during the tapping and implantation (i.e., screw placement) stages which ultimately led to the screw being placed in a completely random place relative to the original drilled hole, thereby creating a hazard for the patient. At best, in this situation a surgeon might realize that the k-wire is loose, however, upon realizing the k-wire is loose, the surgeon must drill a new hole which might weaken the bone locally, for example, because now two holes will be drilled in close to each other. Furthermore, redrilling unnecessarily prolongs the surgery. The likelihood of complications in k-wire use is significantly increased in percutaneous and minimally invasive surgeries (MIS) due to the obstructed view of the surgeon.

For these reasons spinal surgery is difficult to execute without complication. The use of a robotic surgical system to assist in precise bone drilling is of great use to a surgeon, but additional risks arising from maintaining precise trajectories during tapping and implant placement remain.

There is a need for surgical instruments and surgical instrument systems engineered for use with robotic surgical systems that allow for precise trajectories to be followed during all stages of surgical procedures. Particularly, surgical instruments engineered for use in drilling, tapping, and placing of implants are needed for use in orthopedic and spinal procedures, as well as neurological procedures.

SUMMARY

Described herein are systems and apparatus of surgical instruments engineered for integration with robotic surgical systems to enhance precision in surgical procedures. Also described herein are methods of using such surgical instruments in performing surgical procedures. The use of such surgical instruments reduce complications arising from misalignment during surgery. Collectively a set of engineered surgical instruments as described herein (referred to herein collectively as "a universal surgical instrument system") assist in stages of a surgical procedure that require a precise trajectory to be followed. Surgical instrument guides are attached to a universal surgical instrument guide, which is engineered to attach directly or indirectly with a robotic arm of a robotic surgical system. Surgical instruments can then be precisely guided along an axis defined by the universal surgical instrument guide. In certain embodiments, the surgical trajectory is defined by an axis along a channel in the universal surgical instrument guide. Individual instruments are easily inserted and removed from the channel of the universal surgical instrument guide, thus allowing a range of instruments to be used throughout a procedure while maintaining the surgical trajectory.

Universal surgical instrument guides provide an engineered interface between a robotic arm and surgical instruments and their guides that eliminates the need for intraoperative realignment when switching between instruments or instrument guides. Universal surgical instrument guides are engineered to securely attach to a robotic arm using alignment members (e.g., pins) that are received by openings in a portion of the robotic arm. The use of alignment members ensures the consistent alignment of the universal surgical instrument guide relative to the robotic arm. Universal surgical instrument guides have a channel for holding surgical instrument guides and surgical instruments. In certain embodiments, surgical instrument guides are inserted through a channel on a universal surgical instrument guide and are secured in place by releasably attaching the surgical instrument guide to the universal surgical instrument guide. In certain embodiments, the surgical instrument guide is releasably attached using threads on the universal surgical instrument guide and the surgical instrument guide that engage each other. Universal surgical instrument guides additionally have an opening for attaching a navigation marker. When combined with patient measurements (e.g., CT data) taken pre- or intra-operatively, navigation markers enable surgeons to monitor the position and trajectories of surgical instruments relative to a patient's anatomy intraoperatively with high precision.

The surgical instruments described herein may be used in conjunction with the universal surgical instrument guides described herein to assist a surgeon in performing surgical procedures. Systems and apparatus described herein may be used in orthopedic (e.g., spinal) surgical procedures to eliminate the need for a k-wire. Systems and apparatus described herein may also be used with k-wires if desired or necessary for a given procedure. In certain embodiments, the systems and apparatus described herein provide guidance of all important surgical instruments necessary in methods of placing pedicle screws: a drill, a tap and a screwdriver. In certain embodiments, systems and methods described herein use an anti-skiving drill bit to ensure correct drilling even in very demanding anatomy.

In certain embodiments, sets of guides used in surgical procedures have a similar length such that a terminal end of each guide terminates in substantially the same plane when each of the guides is inserted into the universal surgical instrument guide. Thus, when tracking the location of surgical instruments during a procedure, the position of the terminal end of a guide can be used for intraoperative planning and trajectory calculations by calculating the location of the terminal end based on its engineered position relative to the universal surgical instrument guide (whose position is determined from the attached navigation marker).

In certain embodiments, surgical methods comprise: trajectory planning, vertebrae approach, drilling, dilating, tapping, and screw placement.

In certain embodiments, trajectory planning is done using haptic, hands-on planning. No incision is necessary at this point as a surgeon uses a navigation system and a projected trajectory (e.g., based on the orientation of the universal surgical instrument guide and patient measurements from medical images and additional navigation markers) in order to find an optimal entry point for the surgical procedure. When the surgeon finds an optimal trajectory, the surgeon can block movement of the robotic arm on an axis defined by the orientation of the surgical instrument guide inserted in the universal surgical instrument guide.

In certain embodiments, to approach a bone, a surgeon makes a small incision under the drill guide (after it is aligned using the robotic arm) and approaches the bone surface in a trajectory mode (e.g., the surgical instrument guide and any surgical instrument place therethrough slides along a virtual line in space). In certain embodiments, the surgeon has haptic feedback when going through various levels of soft tissue and can feel when the instrument touches the bone. Haptic feedback allows surgeon to confirm that the visual feedback the surgeon sees on a navigation screen is precise (e.g., if surgeon feels touching the bone and navigation shows that he is far away from it, it means that there is some navigation error). In certain embodiments, drilling is performed using an anti-skiving drill bit.

In certain embodiments, dilators are used to provide clear access to surgical sites while simultaneously facilitating surgical instrument guidance. It is necessary to use dilators in percutaneous approaches in order to protect soft tissue from destruction when tapping and screw placement. Additionally, dilators can provide access channels wide enough for pedicle screw extenders.

In certain embodiments, tapping is performed using standard bone tap adapted to fit in an engineered surgical tap guide. Utilizing a robotic surgical system to provide surgical tap guidance during this step is important for patient safety because a sharp tap could potentially take different trajectory than drilled hole. In certain embodiments, a screw is placed together with a screw extender. A screw extender is necessary in certain percutaneous procedures in order to later place a rod and perform reduction (i.e., re-alignment of spine).

The systems, apparatus, and methods described herein are particular beneficial in percutaneous and MIS procedures, but can additionally provide benefit in open surgeries. Systems and apparatus described herein enable surgeons to do percutaneous screw placement without using k-wires. In certain embodiments, by guiding all instruments used in a surgical procedure, systems described herein simplify surgical procedures for surgeons as they are not required to find the same trajectory several times (e.g., during planning, drilling, tapping and screw placement). Additionally, potential risks are removed (e.g., surgeon making an error and placing subsequent instruments in incorrect trajectories) and surgery is potentially shortened.

In one aspect, the disclosed technology includes a universal surgical instrument guide for accommodating surgical instruments to facilitate precise positioning of the surgical instruments using a robotic surgical system, the universal surgical instrument guide including: a body arranged to be mechanically coupled to a robotic arm of the robotic surgical system, the body comprising: a first channel comprising an interior surface sized and shaped to accommodate a tightening screw that, upon insertion and engaging of the tightening screw, securely attaches the body directly or indirectly to the robotic arm of the robotic surgical system, a second channel (e.g., wherein a diameter of the second channel is greater than a diameter of the first channel) having an interior surface shaped and sized to accommodate a portion of a surgical instrument guide, wherein: the second channel comprises a first opening, wherein a portion of the second channel adjacent to the first opening is threaded such that when the surgical instrument guide is inserted in the second channel, threads of the threaded portion of the second channel engage threads on the surgical instrument guide to securely hold the surgical instrument guide, and the interior surface of the second channel defines an axis such that, when the surgical instrument guide is inserted into the universal surgical instrument guide (e.g., when the threads of the threaded portion of the second channel engage the threads on the surgical instrument guide), movement of a surgical instrument is constrained along the axis when the surgical instrument guide is moved within the surgical instrument guide; and an opening (e.g., a threaded opening) sized and shaped to receive a fastener to attach a navigation marker used by a navigation camera to track the position of the surgical instrument guide; and one or more alignment members (e.g., 3 pins) extending from the body such that the one or more alignment members, upon mechanically coupling the body to the robotic arm, engage one or more openings in the robotic arm (e.g., a tool support of the robotic arm), thereby precisely locating the universal instrument guide relative to the robotic arm.

In certain embodiments, the body comprises an opening (e.g., four openings) (e.g., a threaded opening) sized and shaped to receive a fastener to attach a handle support member (e.g., a rod) to the body (e.g., such that a sterile handle can be securely attached to the body).

In certain embodiments, the universal surgical instrument guide includes the handle support member, wherein the handle support member is attached to the body.

In certain embodiments, universal surgical instrument guide includes the navigation marker attached to the body (e.g., wherein the navigation marker comprising a plurality of navigation marker elements wherein the plurality of navigation marker elements are used to triangulate a position of the universal surgical instrument guide).

In certain embodiments, the body comprises a threaded bushing having an interior surface.

In certain embodiments, the interior surface of the threaded bushing defines an axis parallel to an axis defined by the interior surface of the first channel and the interior surface of the threaded bushing is threaded such that the threads on the tightening screw engage the threads on the threaded bushing as the tightening screw is inserted through the threaded bushing.

In certain embodiments, the tightening screw includes: a tip on a proximate end of a screw body; a head on a distal end of the screw body; and threads along a portion of the screw body.

In certain embodiments, the threads along the portion of the screw body are along a portion of the screw body closest to the tip of the tightening screw.

In certain embodiments, the portion of the screw body closest to the head is smooth such that the tightening screw is loosely held in place by the threaded bushing when the tightening screw is fully inserted into the threaded bushing.

In certain embodiments, the surgical instrument guide has a hollow tubular structure sized and shaped to receive a surgical instrument therethrough (e.g., the surgical instrument comprising a member selected from the group consisting of: a drill bit, a tubular dilator, a rod dilator, a surgical tap, a screw driver, a screw extender, and an awl).

In certain embodiments, the surgical instrument guide is a drill guide.

In certain embodiments, the surgical instrument is a drill bit and the drill bit is an anti-skiving drill bit.

In certain embodiments, the surgical instrument guide is a master guide.

In certain embodiments, the robotic surgical system is for use in a member selected from the group consisting of: spinal surgery, ENT surgery, neurosurgery, and orthopedic surgery.

In certain embodiments, an axis along a length of the first channel and an axis of along a length of the second channel are on a common plane.

In certain embodiments, the axis of along the length of the first channel and the axis along the length of the second channel are not perpendicular.

In certain embodiments, the axis along the length of the first channel and the axis along the length of the second channel are perpendicular.

In another aspect, the disclosed technology includes a universal surgical instrument system for use in precise positioning and orienting of surgical instruments using a robotic surgical system, the universal surgical instrument system including: a universal surgical instrument guide comprising: a body arranged to be mechanically coupled to a robotic arm of the robotic surgical system, the body comprising: a first channel having an interior surface sized and shaped to accommodate a tightening screw that, upon insertion and engaging of the tightening screw, securely attaches the body directly or indirectly to the robotic arm of the robotic surgical system, a second channel (e.g., wherein a diameter of the second channel is greater than a diameter of the first channel) having an interior surface shaped and sized to accommodate a portion of a surgical instrument guide, wherein: the second channel comprises a first opening, wherein a portion of the second channel adjacent to the first opening is threaded such that when the surgical instrument guide is inserted in the second channel, threads of the threaded portion of the second channel engage threads on the surgical instrument guide to securely hold the surgical instrument guide, and the interior surface of the second channel defines an axis such that, when the surgical instrument guide is inserted into the universal surgical instrument guide (e.g., when the threads of the threaded portion of the second channel engage the threads on the surgical instrument guide), movement of a surgical instrument is constrained along the axis when the surgical instrument guide is moved within the surgical instrument guide; an opening (e.g., four openings) (e.g., a threaded opening) sized and shaped to receive a fastener to attach a navigation marker used by a navigation camera to track the surgical instrument guide; and one or more alignment members (e.g., 3 pins) extending from the body such that the one or more alignment members, upon mechanically coupling the body to the robotic arm, engage one or more openings in the robotic arm (e.g., a tool support of the robotic arm) thereby precisely locating the universal instrument guide relative to the robotic arm.

In certain embodiments, the universal surgical instrument system includes an opening (e.g., four openings) (e.g., at least one threaded opening) sized and shaped to receive a fastener to attach a handle support member (e.g., a rod) to the body (e.g., such that a sterile handle can be securely attached to the body).

In certain embodiments, the universal surgical instrument system includes the handle support member, wherein the support member is attached to the body.

In certain embodiments, the body comprises an opening (e.g., four openings) (e.g., a threaded opening) sized and shaped to receive a fastener to attach a handle support member (e.g., a rod) to the body (e.g., such that a sterile handle can be securely attached to the body).

In certain embodiments, the handle support member is attached to the body.

In certain embodiments, the universal surgical instrument system includes the navigation marker attached to the body (e.g., wherein the navigation marker comprising a plurality of navigation marker elements wherein the plurality of navigation marker elements are used to triangulate a position of the universal surgical instrument guide).

In certain embodiments, the body comprises a threaded bushing having an interior surface.

In certain embodiments, the interior surface of the threaded bushing defines an axis parallel to an axis defined by the interior surface of the first channel and the interior surface of the threaded bushing is threaded such that the threads on the tightening screw engage the threads on the threaded bushing as the tightening screw is inserted through the threaded bushing.

In certain embodiments, the tightening screw comprises: a tip on a proximate end of a screw body; a head on a distal end of the screw body; and threads along a portion of the screw body.

In certain embodiments, the threads along the portion of the screw body are along a portion of the screw body closest to the tip of the tightening screw.

In certain embodiments, the portion of the screw body closest to the head is smooth such that the tightening screw is loosely held in place by the threaded bushing when the tightening screw is fully inserted into the threaded bushing.

In certain embodiments, universal surgical instrument system includes the surgical instrument guide, wherein the surgical instrument guide has a hollow tubular structure sized and shaped to receive a surgical instrument therethrough (e.g., the surgical instrument comprising a member selected from the group consisting of: a drill bit, a tubular dilator, a rod dilator, a surgical tap, a screw driver, a screw extender, and an awl).

In certain embodiments, the universal surgical instrument system includes the surgical instrument guide, wherein the surgical instrument guide is a drill guide.

In certain embodiments, the universal surgical instrument system includes the surgical instrument, wherein the surgical instrument is a drill bit and the drill bit is an anti-skiving drill bit.

In certain embodiments, the surgical instrument guide is a master guide.

In certain embodiments, the robotic surgical system is for use in a member selected from the group consisting of: spinal surgery, ENT surgery, neurosurgery, and orthopedic surgery.

In certain embodiments, an axis along a length of the first channel and an axis of along a length of the second channel are on a common plane.

In certain embodiments, the axis of along the length of the first channel and the axis along the length of the second channel are not perpendicular.

In certain embodiments, the axis along the length of the first channel and the axis along the length of the second channel are perpendicular.

In certain embodiments, the universal surgical instrument system includes a drill guide, the drill guide comprising: a proximal portion comprising: a first exterior surface that is substantially in contact with the interior surface of the second channel when the drill guide is accommodated therethrough, a second exterior surface comprising threads that engage the threads of the threaded portion of the second channel to securely hold the drill guide when the drill guide is accommodated therethrough, and a collar adjacent to the first exterior surface, wherein a diameter of the collar is larger than a diameter of the first exterior surface such that a distance the drill guide can be threaded through the second channel is limited by the collar; and a guiding shaft attached to the proximal portion, wherein the guiding shaft is sized and shaped to guide a drill bit therethrough along an axis defined by the interior surface of the second channel to a surgical site.

In certain embodiments, the drill bit is an anti-skiving drill bit.

In certain embodiments, the guiding shaft of the drill guide is cylindrical.

In certain embodiments, the universal surgical instrument system includes a master guide, the master guide comprising: a proximal portion comprising: a first exterior surface that is substantially in contact with the interior surface of the second channel when the master guide is accommodated therethrough, a second exterior surface comprising threads that engage the threads of the threaded portion of the second channel to securely hold the master guide when the master guide is accommodated therethrough, and a collar adjacent to the first exterior surface, wherein a diameter of the collar is larger than a diameter of the first exterior surface such that a distance the master guide may be threaded through the second channel is limited by the collar, a guiding shaft attached to the proximal portion, wherein the guiding shaft has an interior surface having a dimension such that a first surgical instrument or second surgical instrument guide can be accommodated therethrough along an axis defined by the interior surface of the second channel to a surgical site.

In certain embodiments, the guiding shaft of the master guide is cylindrical.

In certain embodiments, the proximal portion of the master guide comprises: a first channel, wherein the first channel has an axis coincident with an axis of the guiding shaft, and a first opening, wherein a portion of the first channel of the master guide adjacent to the first opening is threaded such that when the second surgical instrument is accommodated therethrough, threads of the threaded portion of the first channel of the master guide engage threads on the second surgical instrument to securely hold the second surgical instrument.

In certain embodiments, the universal surgical instrument system includes a master guide, wherein the master guide has a length such that when the master guide is fully threaded into the universal surgical instrument guide, the distance from the first opening of the universal surgical instrument guide to a terminal end of the guiding shaft of the master guide is the distance of a terminal end of the guiding shaft of the drill guide to the first opening of the universal surgical instrument guide when the drill guide is fully threaded into the universal surgical instrument guide.

In certain embodiments, the universal surgical instrument system includes a tubular dilator, the tubular dilator comprising: a body with a cross-section such that the body can be accommodated within and through the guiding shaft of the master guide such that the tubular dilator is constrained to move only along an axis defined by the guiding shaft of the master guide, the body comprising: a guiding shaft having an interior surface having a dimension such that a third surgical instrument can be accommodated therethrough along an axis defined by the interior surface of the second channel to a surgical site.

In certain embodiments, the guiding shaft of the tubular dilator is cylindrical.

In certain embodiments, the guiding shaft has a tapered end.

In certain embodiments, the universal surgical instrument system includes a rod dilator, the rod dilator comprising: a body with a cross-section such that the body can be accommodated within and through the guiding shaft of the tubular dilator such that the rod dilator is constrained to move only along the axis defined by the guiding shaft of the tubular dilator.

In certain embodiments, the universal surgical instrument system includes a surgical tap guide, the surgical tap guide comprising: a proximal portion comprising: an exterior surface comprising threads that engage the threads of the threaded portion of the first channel of the master guide to securely hold the surgical tap guide when the surgical tap guide is accommodated therethrough, and a collar adjacent to the first exterior surface, wherein a diameter of the collar is larger than a diameter of the exterior surface of the surgical tap guide such that a distance the surgical tap guide may be threaded through the master guide is limited by the collar; and one or more stabilizing ends, each of the one or more stabilizing ends having: an exterior surface substantially in contact with the first channel of the master guide when the tap guide is accommodated therethrough, and an interior surface sized and shaped to guide a surgical tap along an axis defined by the interior surface of the second channel to a surgical site.

In certain embodiments, each of the one or more stabilizing ends of the surgical tap guide is cylindrical.

In certain embodiments, the surgical tap guide has a length such that when the surgical tap guide is fully threaded into the master guide, a terminal end of the surgical tap guide is approximately flush with a terminal end of the guiding shaft of the master guide.

In certain embodiments, the universal surgical instrument system includes a modified surgical tap, the modified surgical tap comprising: a body having an elongated member with homogeneous diameter; a proximal end comprising a handle sized and shaped for gripping by a surgeon; and a pointed, threaded distal end.

In certain embodiments, the universal surgical instrument system includes a screw extender having a body sized and shaped to be pass through the guiding shaft of the master guide in a manner that is constrained in all directions except a direction along the axis of the second channel, wherein the screw extender has an interior surface sized and shaped to accommodate a portion of a screwdriver and a distal end for releasably holding a surgical screw.

In certain embodiments, the universal surgical instrument system includes the surgical screw for placing in a bone of a patient, wherein the surgical screw can be releasably held by the screw extender.

In certain embodiments, the universal surgical guide system includes a k-wire.

In another aspect, the disclosed technology includes a method of using a robotic surgical system, the method including the steps of: attaching a universal surgical instrument guide to an end effector of a robotic arm, the universal surgical instrument guide arranged to securely hold a surgical instrument guide and restrict movement of a surgical instrument therethrough, wherein the universal surgical instrument guide comprises: a body comprising: a first channel comprising an interior surface sized and shaped to accommodate a tightening screw that, upon insertion and engaging of the tightening screw, securely attaches the body directly or indirectly to the robotic arm of the robotic surgical system, a second channel (e.g., wherein a diameter of the second channel is greater than a diameter of the first channel) having an interior surface shaped and sized to accommodate a portion of a surgical instrument guide, wherein the second channel comprises a first opening, wherein a portion of the second channel adjacent to the first opening is threaded such that when the surgical instrument guide is inserted in the second channel, threads of the threaded portion of the second channel engage threads on the surgical instrument guide to securely hold the surgical instrument guide, and the interior surface of the second channel defines an axis such that, when the surgical instrument guide is inserted into the universal surgical instrument guide (e.g., when the threads of the threaded portion of the second channel engage the threads on the surgical instrument guide), movement of a surgical instrument ins is constrained along the axis when the surgical instrument guide is moved within the surgical instrument guide.

In certain embodiments, the body comprises a threaded bushing having an interior surface.

In certain embodiments, the interior surface of the threaded bushing defines an axis parallel to an axis defined by the interior surface of the first channel and the interior surface of the threaded bushing is threaded such that the threads on the tightening screw engage the threads on the threaded bushing as the tightening screw is inserted through the threaded bushing.

In certain embodiments, the tightening screw comprises: a tip on a proximate end of a screw body; a head on a distal end of the screw body; and threads along a portion of the screw body.

In certain embodiments, the threads along the portion of the screw body are along a portion of the screw body closest to the tip of the tightening screw.

In certain embodiments, the portion of the screw body closest to the head is smooth such that the tightening screw is loosely held in place by the threaded bushing when the tightening screw is fully inserted into the threaded bushing.

In certain embodiments, attaching the universal surgical instrument guide to an end effector of the robotic arm comprises: aligning the universal surgical instrument guide to the end effector, wherein the universal surgical instrument guide comprises one or more alignment members (e.g., 3 pins) extending from the body such that the one or more alignment members, upon mechanically coupling the body to the robotic arm, engage one or more openings in the robotic arm (e.g., a tool support of the robotic arm) thereby precisely locating the universal instrument guide relative to the robotic arm; and engaging the tightening screw.

In another aspect, the disclosed technology includes a robotic surgical system for performing surgery, the system comprising: a robotic arm with an end effector comprising a universal surgical instrument guide arranged to securely hold a surgical instrument guide and restrict movement of a surgical instrument therethrough; and a manipulator arranged to allow robotically-assisted or unassisted positioning and/or movement of the surgical instrument guide by a user with at least four degrees of freedom to align an axis defined by the universal surgical instrument guide at a desired trajectory in relation to a patient situation, wherein the universal surgical instrument guide comprises: a body arranged to be mechanically coupled to the robotic arm, the body comprising: a first channel having an interior surface sized and shaped to accommodate a tightening screw that, upon insertion and engaging of the tightening screw, securely attaches the body directly or indirectly to the robotic arm of the robotic surgical system, a second channel (e.g., wherein a diameter of the second channel is greater than a diameter of the first channel) having an interior surface shaped and sized to accommodate a portion of a surgical instrument guide, wherein: the second channel comprises a first opening, wherein a portion of the second channel adjacent to the first opening is threaded such that when the surgical instrument guide is inserted in the second channel, threads of the threaded portion of the second channel engage threads on the surgical instrument guide to securely hold the surgical instrument guide, and the interior surface of the second channel defines an axis such that, when the surgical instrument guide is inserted into the universal surgical instrument guide (e.g., when the threads of the threaded portion of the second channel engage the threads on the surgical instrument guide), movement of a surgical instrument guide is constrained along the axis when the surgical instrument guide is moved within the surgical instrument guide, a handle support member (e.g., a rod) arranged for the manipulator to be securely held thereto, and an opening (e.g., a threaded opening) sized and shaped to receive a fastener to attach a navigation marker used by a navigation camera to track the position of the surgical instrument guide.

In certain embodiments, the body comprises: an opening (e.g., four openings) (e.g., at least one threaded opening) sized and shaped to receive a fastener to attach a handle support member (e.g., a rod) to the body (e.g., such that a sterile handle can be securely attached to the body).

In certain embodiments, the robotic surgical system includes the handle support member, wherein the support member is attached to the body.

In certain embodiments, the universal surgical guide comprises: the navigation marker attached to the body (e.g., the navigation marker comprising a plurality of navigation marker elements wherein the plurality of navigation marker elements are used to triangulate a position of the universal surgical instrument guide).

In certain embodiments, robotic surgical system includes a drill guide, the drill guide comprising: a proximal portion comprising: a first exterior surface that is substantially in contact with the interior surface of the second channel when the drill guide is accommodated therethrough, a second exterior surface comprising threads that engage the threads of the threaded portion of the second channel to securely hold the drill guide when the drill guide is accommodated therethrough, and a collar adjacent to the first exterior surface, wherein a diameter of the collar is larger than a diameter of the first exterior surface such that a distance the drill guide can be threaded through the second channel is limited by the collar; and a guiding shaft attached to the proximal portion, wherein the guiding shaft is sized and shaped to guide a drill bit therethrough along an axis defined by the interior surface of the second channel to a surgical site.

In certain embodiments, the drill bit is an anti-skiving drill bit.

In certain embodiments, the guiding shaft of the drill guide is cylindrical.

In certain embodiments, robotic surgical system includes a master guide, the master guide comprising: a proximal portion comprising: a first exterior surface that is substantially in contact with the interior surface of the second channel when the master guide is accommodated therethrough, a second exterior surface comprising threads that engage the threads of the threaded portion of the second channel to securely hold the master guide when the master guide is accommodated therethrough, and a collar adjacent to the first exterior surface, wherein a diameter of the collar is larger than a diameter of the first exterior surface such that a distance the master guide may be threaded through the second channel is limited by the collar, a guiding shaft attached to the proximal portion, wherein the guiding shaft has an interior surface having a dimension such that a first surgical instrument or second surgical instrument guide can be accommodated therethrough along an axis defined by the interior surface of the second channel to a surgical site.

In certain embodiments, the guiding shaft of the master guide is cylindrical.

In certain embodiments, the proximal portion of the master guide comprises: a first channel, and a first opening, wherein a portion of the first channel of the master guide adjacent to the first opening is threaded such that when the second surgical instrument is accommodated therethrough, threads of the threaded portion of the first channel of the master guide engage threads on the second surgical instrument to securely hold the second surgical instrument.

In certain embodiments, robotic surgical system includes a tubular dilator, the tubular dilator comprising: a body with a cross-section such that the body can be accommodated within and through the guiding shaft of the master guide such that the tubular dilator is constrained to move only along an axis defined by the guiding shaft of the master guide, the body comprising: a guiding shaft having an interior surface having a dimension such that a third surgical instrument can be accommodated therethrough along an axis defined by the interior surface of the second channel to a surgical site.

In certain embodiments, the guiding shaft of the tubular dilator is cylindrical.

In certain embodiments, the robotic surgical system includes a rod dilator, the rod dilator comprising: a body with a cross-section such that the body can be accommodated within and through the guiding shaft of the tubular dilator such that the rod dilator is constrained to move only along the axis defined by the guiding shaft of the tubular dilator.

In certain embodiments, the robotic surgical system includes a surgical tap guide, the surgical tap guide comprising: a proximal portion comprising: an exterior surface comprising threads that engage the threads of the threaded portion of the first channel of the master guide to securely hold the surgical tap guide when the surgical tap guide is accommodated therethrough, and a collar adjacent to the first exterior surface, wherein a diameter of the collar is larger than a diameter of the exterior surface of the surgical tap guide such that a distance the surgical tap guide may be threaded through the master guide is limited by the collar; and one or more stabilizing ends, each of the one or more stabilizing ends having: an exterior surface substantially in contact with the first channel of the master guide when the tap guide is accommodated therethrough, and an interior surface sized and shaped to guide a surgical tap along an axis defined by the interior surface of the second channel to a surgical site.

In certain embodiments, the each of the one or more stabilizing ends of the surgical tap guide is cylindrical.

In certain embodiments, robotic surgical system includes a modified surgical tap, the modified surgical tap comprising: a body having an elongated member with homogeneous diameter; a proximal end comprising a handle sized and shaped for gripping by a surgeon; and a pointed, threaded distal end.

In certain embodiments, robotic surgical system including a screw extender having a body sized and shaped to be pass through the guiding shaft of the master guide in a manner that is constrained in all directions except a direction along the axis of the second channel, wherein the screw extender has an interior surface sized and shaped to accommodate a portion of a screwdriver and a distal end for releasably holding a surgical screw.

In certain embodiments, robotic surgical system including the surgical screw for placing in a bone of a patient, wherein the surgical screw can be removably attached to the screw extender.

In another aspect, the disclosed technology includes a method of using a robotic surgical system, the method including the steps of: moving a mobile cart transporting a robotic surgical system comprising a robotic arm in proximity to an operating table, wherein the robotic arm has an end effector comprising a universal surgical instrument guide attached thereto, the universal surgical instrument guide arranged to securely hold a surgical instrument guide and restrict movement of a surgical instrument therethrough, wherein the universal surgical instrument guide comprises: a body comprising: a first channel having an interior surface shaped and sized to accommodate a portion of a surgical instrument guide, wherein the first channel comprises a first opening, wherein a portion of the second channel adjacent to the first opening is threaded such that when the surgical instrument guide is inserted in the second channel, threads of the threaded portion of the second channel engage threads on the surgical instrument guide to securely hold the surgical instrument guide, and the interior surface of the second channel defines an axis such that, when the surgical instrument guide is inserted into the universal surgical instrument guide (e.g., when the threads of the threaded portion of the second channel engage the threads on the surgical instrument guide), movement of a surgical instrument is constrained along the axis when the surgical instrument guide is moved within the surgical instrument guide, and a navigational marker (e.g., wherein the navigational marker comprising a plurality of navigation marker elements wherein the plurality of navigation marker elements are used to triangulate a position of the surgical instrument guide (e.g., and/or the universal surgical instrument guide)) is attached to the universal surgical instrument guide for use by a navigation camera to track the position of the surgical instrument guide; stabilizing the mobile cart; inserting the surgical instrument guide by threading the surgical instrument guide into the universal surgical instrument guide, wherein the surgical instrument guide comprises: a proximal portion comprising: a first exterior surface that is substantially in contact with the interior surface of the first channel when the surgical instrument guide is accommodated therethrough, a second exterior surface comprising threads that engage the threads of the threaded portion of the first channel to securely hold the surgical instrument guide when the surgical instrument guide is accommodated therethrough, and a collar adjacent to the first exterior surface, wherein a diameter of the collar is larger than a diameter of the first exterior surface such that a distance the surgical instrument guide may be threaded through the first channel is limited by the collar, and a guiding shaft attached to the proximal portion, wherein the guiding shaft has an interior surface having a dimension such that the surgical instrument can be accommodated therethrough along an axis defined by the interior surface of the first channel to a surgical site; maneuvering the robotic arm to a desired position to align the axis defined by the interior surface of the first channel of the universal surgical instrument guide (e.g., an axis defined by the guiding shaft of the surgical instrument guide) at a desired trajectory in relation to the surgical site; limiting movement of the robotic arm to only along the axis defined by the interior surface of the first channel; and temporarily fixing the position of the robotic arm (and, therefore, the position of the universal surgical instrument guide and the surgical instrument guide).

In certain embodiments, the method includes the steps of: inserting the surgical instrument through the surgical instrument guide; and maneuvering the surgical instrument in a manner that is constrained by the surgical instrument guide.

In certain embodiments, the robotic arm is active and non-backdrivable.

In certain embodiments, the robotic surgical system comprises a force sensor attached to the robotic arm capable of providing haptic feedback to a user.

In certain embodiments, the robotic surgical system provides haptic feedback when the surgical instrument guide contacts bone.

In certain embodiments, the surgical instrument guide is a drill guide.

In certain embodiments, the method includes inserting a drill bit through the guide shaft of the drill guide to direct the drill bit to the surgical site.

In certain embodiments, the drill bit is an anti-skiving drill bit.

In certain embodiments, the method includes the steps of: removing the drill bit from the guiding shaft of the drill guide; and inserting a k-wire through the guiding shaft of the drill guide.

In certain embodiments, the method includes the steps of: removing the drill bit from the guiding shaft of the drill guide; removing the drill guide from universal surgical instrument guide; inserting a master guide into the first channel of the universal surgical instrument guide; and releasably securing the master guide to the universal surgical instrument guide by threading the master guide such that the threads of the portion of the first channel engage with threads on an exterior surface of the master guide.

In certain embodiments, the master guide comprises: a proximal portion comprising: a first exterior surface that is substantially in contact with the interior surface of the second channel when the master guide is accommodated therethrough, a second exterior surface comprising threads that engage the threads of the threaded portion of the second channel to securely hold the master guide when the master guide is accommodated therethrough, and a collar adjacent to the first exterior surface, wherein a diameter of the collar is larger than a diameter of the first exterior surface such that a distance the master guide may be threaded through the second channel is limited by the collar, a first channel, and a first opening, wherein a portion of the first channel of the master guide adjacent to the first opening is threaded such that when the second surgical instrument is accommodated therethrough, threads of the threaded portion of the first channel of the master guide engage threads on the second surgical instrument to securely hold the second surgical instrument; and a guiding shaft (e.g., a cylindrical shaft) attached to the proximal portion, wherein the guiding shaft has an interior surface having a dimension such that a first surgical instrument or second surgical instrument guide can be accommodated therethrough along an axis defined by the interior surface of the second channel to a surgical site.

In certain embodiments, the method includes the steps of inserting a tubular dilator into a guiding shaft of the master guide; and inserting a rod dilator into a guiding shaft of the tubular dilator.

In certain embodiments, the tubular dilator comprises: a body (e.g., a cylindrical body) with a cross-section such that the body can be accommodated within and through the guiding shaft of the master guide such that the tubular dilator is constrained to move only along an axis defined by the guiding shaft of the master guide, the body comprising: a guiding shaft having an interior surface having a dimension such that a third surgical instrument can be accommodated therethrough along an axis defined by the interior surface of the second channel to a surgical site.

In certain embodiments, the method includes the steps of: removing the rod dilator from the guiding shaft of the tubular dilator; removing the tubular dilator from the guiding shaft of the master guide; inserting a surgical tap guide into the guiding shaft of the master guide; and releasably securing the surgical tap guide to the master guide by threading the surgical tap guide such that threads on an internal surface of the master guide engage with threads on an exterior surface of the surgical tap guide.

In certain embodiments, the surgical tap guide comprises: a proximal portion comprising: an exterior surface comprising threads that engage the threads of the threaded portion of the first channel of the master guide to securely hold the surgical tap guide when the surgical tap guide is accommodated therethrough, and a collar adjacent to the first exterior surface, wherein a diameter of the collar is larger than a diameter of the exterior surface of the surgical tap guide such that a distance the surgical tap guide may be threaded through the master guide is limited by the collar; and one or more stabilizing ends, each of the one or more stabilizing ends having: an exterior surface substantially in contact with the first channel of the master guide when the tap guide is accommodated therethrough, and an interior surface sized and shaped to guide a surgical tap along an axis defined by the interior surface of the second channel to a surgical site.

In certain embodiments, the method includes the step of: inserting a surgical tap into the surgical tap guide.

In certain embodiments, the method includes the steps of: removing the surgical tap from the surgical tap guide; removing the surgical tap guide; and inserting a screw extender and screw into the guiding shaft of the master guide, wherein the screw is releasably held by the screw extender.

In certain embodiments, the method includes the steps of: inserting a screwdriver into the screw extender, such that the screwdriver is in contact with a head of the screw; and removing the screwdriver.

In certain embodiments, the method includes the step of: moving the robotic arm along the axis defined by the interior surface of the first channel such that no portion of the screw extender resides within the guiding shaft of the master guide.

BRIEF DESCRIPTION OF THE DRAWINGS

Drawings are presented herein for illustration purposes, not for limitation. The foregoing and other objects, aspects, features, and advantages of the invention will become more apparent and may be better understood by referring to the following description taken in conjunction with the accompanying drawings, in which:

FIG. 18 and FIG. 18B show a coordinate system for defining the location of a tool center point where the center of terminal aspect of a robotic arm defines the origin of the coordinate system, according to an illustrative embodiment of the invention;

FIGS. 21-52 are illustrations of a patient's anatomy and a surgical robotic system during a method of performing a surgical procedure on the patient's spine using the robotic surgical system with a universal surgical instrument system attached thereto, according to an illustrative embodiment of the invention.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Figure 1:
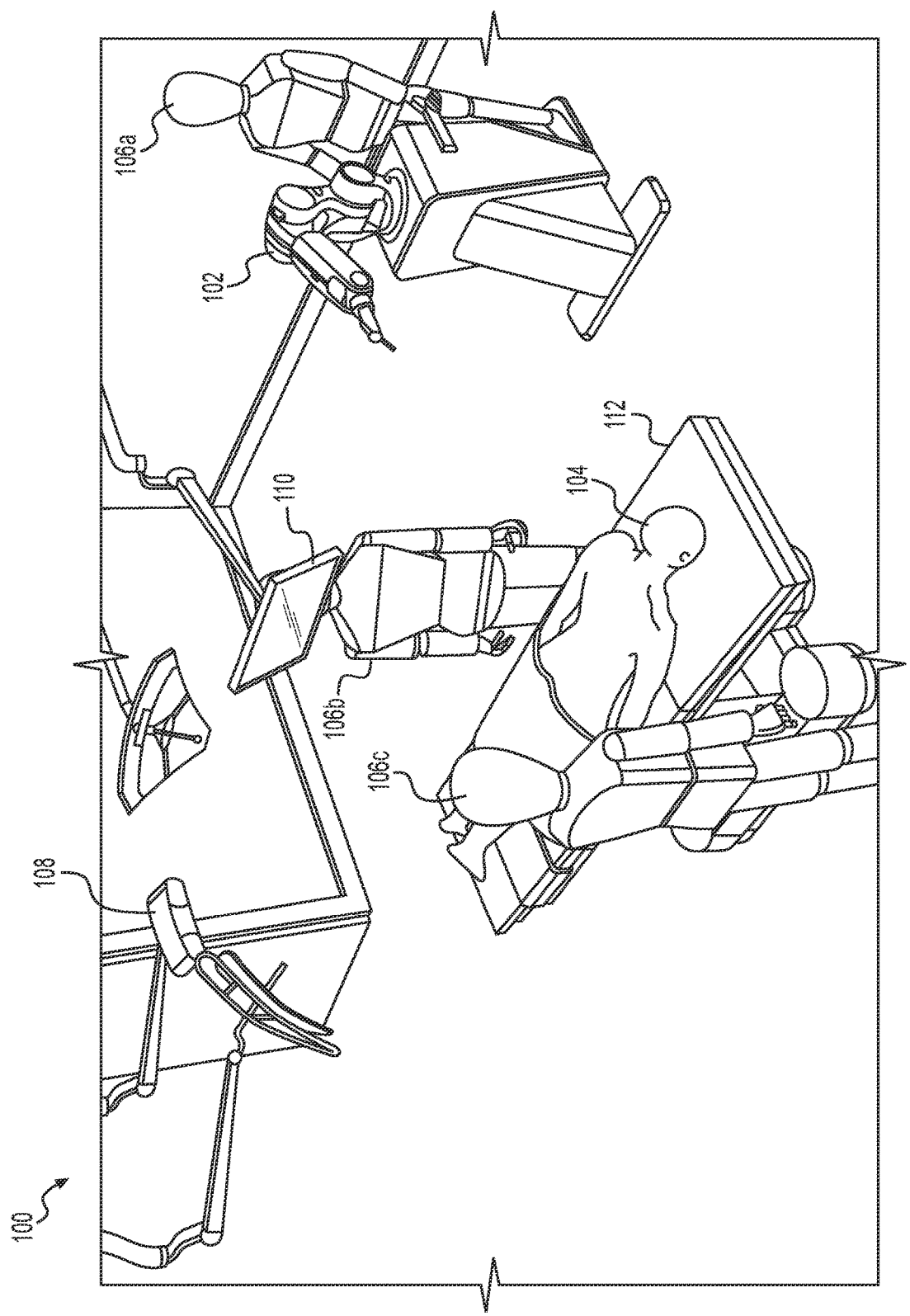
FIG. 1 is an illustration of a robotic surgical system in an operating room, according to an illustrative embodiment of the invention.

FIG. 1 illustrates an example robotic surgical system in an operating room 100. In some implementations, one or more surgeons, surgical assistants, surgical technologists and/or other technicians, (106a-c) perform an operation on a patient 104 using a robotic-assisted surgical system. In the operating room the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion. In some implementations, the surgical robotic system includes a surgical robot 102 on a mobile cart. The surgical robot 102 may be positioned in proximity to an operating table 112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

The mobile cart may permit a user (operator) 106a, such as a technician, nurse, surgeon, or any other medical personnel in the operating room, to move the surgical robot 102 to different locations before, during, and/or after a surgical procedure. The mobile cart enables the surgical robot 102 to be easily transported into and out of the operating room 100. For example, a user 106a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

For safety reasons, the mobile cart may be provided with a stabilization system that may be used during a surgical procedure performed with a surgical robot. The stabilization system increases the global stiffness of the mobile cart relative to the floor in order to ensure the accuracy of the surgical procedure. In some implementations, the wheels include a locking system that prevents the cart from moving. The stabilizing, braking, and/or locking system may be activated when the machine is turned on. In some implementations, the mobile cart includes multiple stabilizing, braking, and/or locking systems. In some implementations, the stabilizing system is electro-mechanical with electronic activation. The stabilizing, braking, and/or locking system(s) may be entirely mechanical. The stabilizing, braking, and/or locking system(s) may be electronically activated and deactivated.

In some implementations, the surgical robot 102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, a tracking detector 108 monitors the location of patient 104 and the surgical robot 102. The tracking detector may be a camera, a video camera, an infrared detector, field generator and sensors for electromagnetic tracking or any other motion detecting apparatus. In some implementation, based on the patient and robot position, the display screen displays a projected trajectory and/or a proposed trajectory for the robotic arm of robot 102 from its current location to a patient operation site. By continuously monitoring the patient and robotic arm positions, using tracking detector 108, the surgical system can calculate updated trajectories and visually display these trajectories on display screen 110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure.

Figure 2:
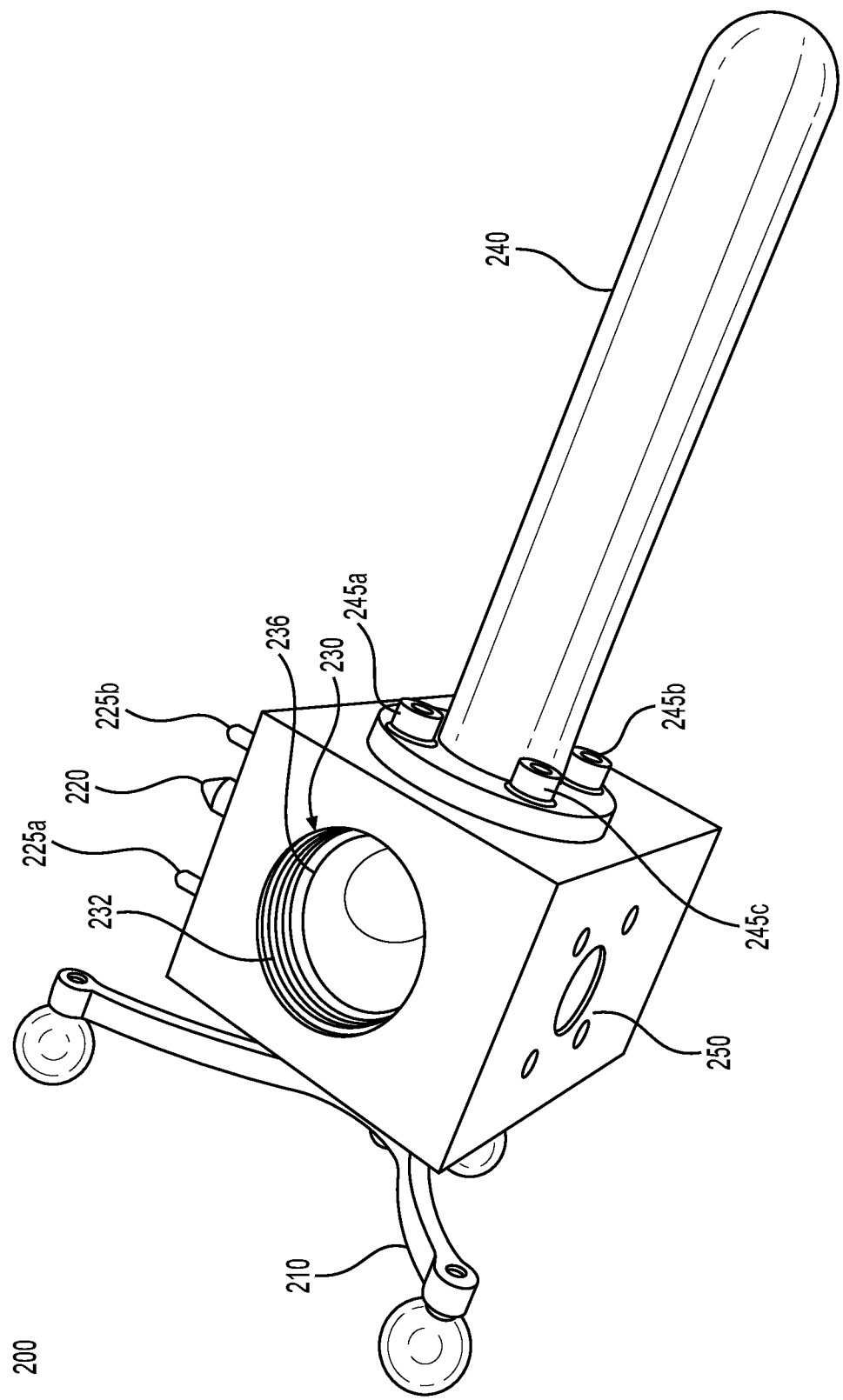
FIG. 2 shows a universal surgical instrument guide, according to an illustrative embodiment of the invention.

FIG. 2 shows a universal surgical instrument guide 200 for attachment to a robotic surgical system. Universal surgical instrument guide attaches to a proximal end of a robotic surgical system with high precision and rigidity using pins 225a-c (pin 225c not shown in FIG. 2) and threaded screw 220. Threaded screw 220 is accessed through first channel 250. The attachment system is described in greater detail below. Second channel 230 is sized for surgical instrument guides to be received therethrough such that a portion of the surgical instrument guides resides in the second channel 230. Additionally, second channel 230 has a threaded portion 232 near one of its openings such that surgical instrument guides can engage the threaded portion 232 to be securely held while in use. The distal end of the threaded portion 232 of second channel 230 has a lip 236 to eliminate the possibility of over-threading a surgical instrument guide. Alternative temporary secure attachment means may be used with the second channel 230 such as tension sleeves, pressure connections, quick connect type fittings, or similar. In some embodiments, surgical instruments are inserted directly through the second channel 230 of a universal surgical instrument guide without the use of an additional surgical instrument guide. In those embodiments, surgical instruments may be appropriately threaded as to engage threads in the second channel 230 of the body of a universal surgical instrument guide. First channel 250 is shown to be oriented perpendicular to second channel 230.

In some embodiments of a universal surgical instrument guide, the first channel 250 and second channel 230 are non-parallel and not perpendicularly oriented.

Figure 4A:
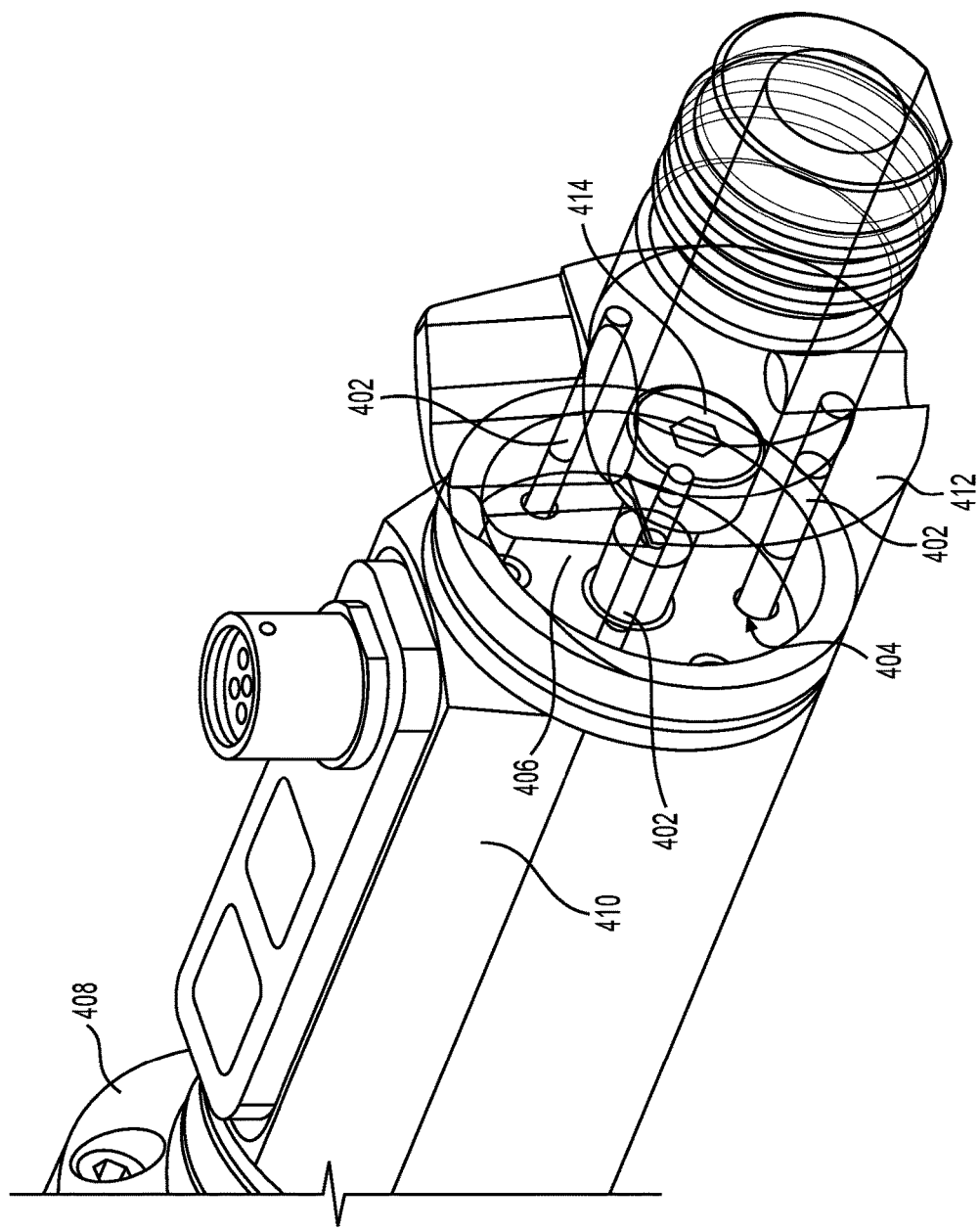
FIGS. 4A and 4B are illustrations of a system for securing an instrument holder (e.g., a universal surgical instrument guide) on a robotic arm, according to an illustrative embodiment of the invention.
Figure 4B:
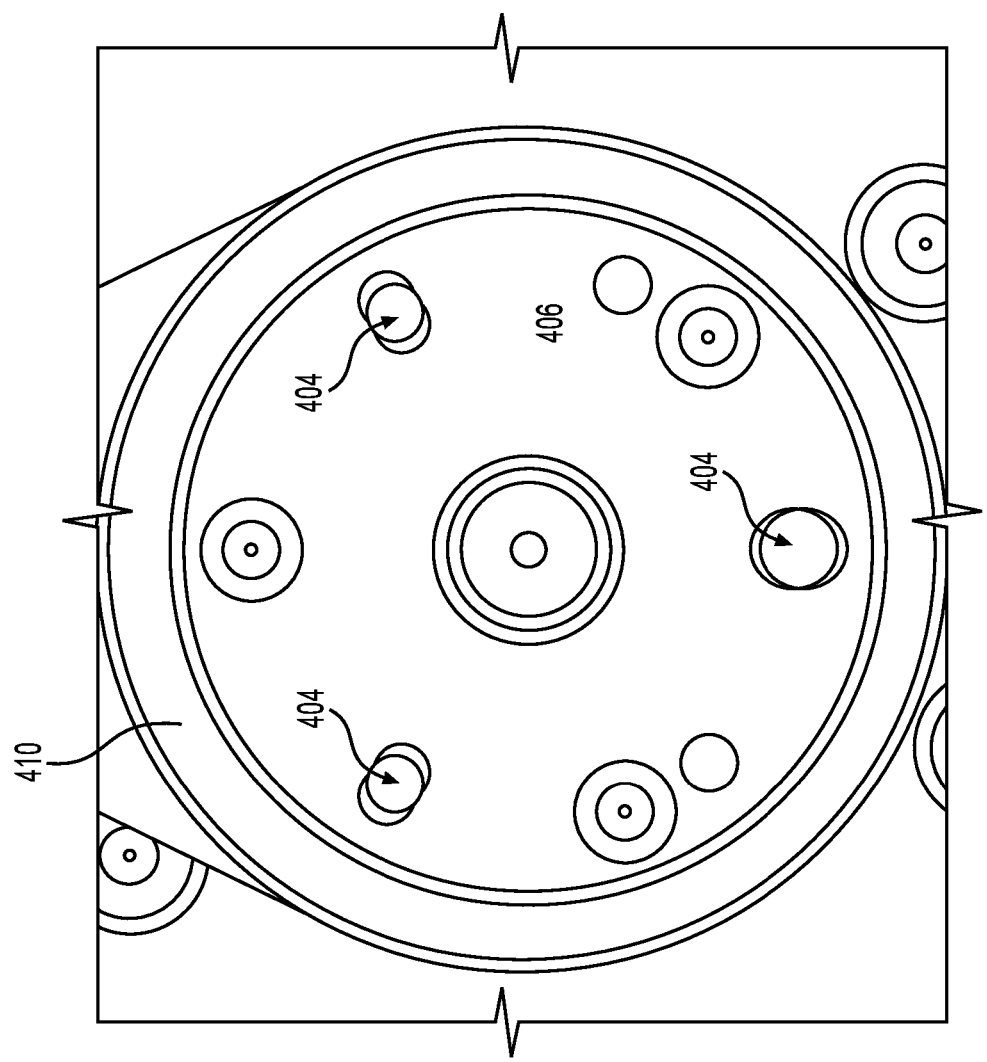

FIGS. 4A-B are illustrations of a system for securing universal surgical instrument guide body 412 on robotic arm 408. Such an illustrative attachment system may be used with universal surgical instrument guides as disclosed herein. In some implementations, the universal surgical instrument guide needs to be sterilized (e.g., in autoclave) prior to attachment. The disclosed universal surgical instrument guide may be easily installed and removed from the robotic system without deteriorating localization precision as well as attachment rigidity. Localization precision may be achieved by, for example, by three localization pins 402 extending from the body. A different number of localization pins 402 may be used (e.g., 1 to 5 pins). The pins 402 may come in contact with oblong openings 404 in a thin localization plate 406 precisely held on the robotic arm 408 (e.g., held on a base of the robotic arm 410). The universal guide's body 412 may be localized on the robotic arm 408 (e.g., held on a base of the robotic arm 410) using pins 402 that come in contact with oblong openings 404 in a localization plate 406 precisely held on the robot 408. A screw 414 may be tightened directly into the robot 408 to rigidly attached the universal guide's body 412 to the robot 408. FIG. 4B illustrates a front view of an example localization plate 406. The one or more pins 402 may extend from the body such that the one or more pins 402, upon mechanically coupling the body to the robotic arm, engage one or more openings 404 in a robotic arm 408 (e.g., in a localization plate 406 of the robotic arm 408) thereby precisely locating the surgical instrument holder relative to the robotic arm 408 (e.g., the one or more openings 404 may be wider than the one or more pins and the one or more openings may taper long their lengths).

In certain embodiments, the body of a universal surgical instrument guide comprises a threaded bushing having a threaded interior surface for receiving a torque screw therethrough. The first channel of the universal surgical instrument guide passes through the interior surface of the threaded bushing. The interior surface of the threaded bushing is threaded such that the threads on the torque screw engage the threads on the threaded bushing as the tightening screw is inserted through the threaded bushing. The torque screw is received by a threaded opening in the localization plate of the robotic arm such that the torque screw may be tightened to securely attach the universal surgical instrument guide to the robotic arm.

Figure 4D:
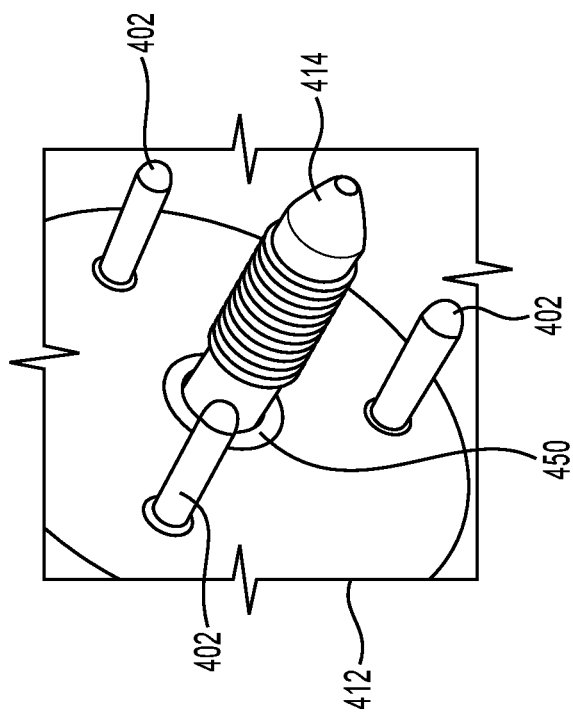
FIG. 4D shows a torque screw inserted through a threaded bushing that is press fit into the body of a universal surgical instrument guide for attaching the guide to a robotic arm, according to an illustrative embodiment of the invention.
Figure 4C:
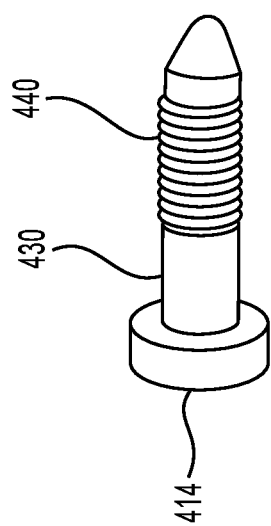
FIG. 4C shows a torque screw appropriate for use in attaching a universal surgical instrument guide to a robotic arm, according to an illustrative embodiment of the invention.

FIG. 4C shows torque screw 414 with threaded portion 440 and smooth stem 430. FIG. 4D shows torque screw 414 inserted into threaded bushing 450. In some implementations, a threaded bushing 450 is press fitted into universal surgical instrument guide body 412. Torque screw 414 is made of metal such that it provides a strong attachment to the robot and satisfies cleaning and sterilization requirements. Threaded portion 440 of torque screw 414 engages threaded bushing 450 that is press fitted into universal surgical instrument guide body 450. As torque screw 414 is tightened, threaded portion 440 of torque screw 414 passes through threaded bushing 450 such that smooth stem 430 closest to the torque screw head resides in threaded bushing 450 (e.g., somewhat loosely since there are no threads on smooth stem 430 and thus a smaller diameter). The advantage here is the torque screw 414 and universal surgical instrument guide body 412 can then be mounted on the robot without the risk of losing torque screw 414 during assembly as torque screw 414 cannot slide out of threaded bushing 450 without unscrewing torque screw 414 from bushing 450. The universal surgical instrument guide in this example includes localization pins 402 as described above. Smooth stem 430 also provides a gap between the torque screw 414 and bushing 450 for cleaning.

Referring again to FIG. 2, universal surgical instrument guide 200 has sterile handle support member 240. Sterile handle support member 240 is attached to universal surgical instrument guide 200 with fasteners 245a-d (fastener 245d not shown). Sterile handle support member 240 is sized and shaped to accommodate a sterile handle assembly for gripping by a surgeon in order to manipulate the position of the end-effector of the robotic surgical system. Sterile handle support member 240 is removably attached to universal surgical instrument guide 200. Removable attachment can, for example, assist in sterilization of a universal surgical instrument guide and its handle support member. In some embodiments, robotic surgical systems comprise a manipulator for the end-effector located in an alternative location (i.e., not on the universal surgical instrument guide). Removable attachment of the handle support member 240 additionally allows the support member 240 to be removed from the robotic surgical system when it is not necessary as to not have an unnecessary obstruction on the universal surgical instrument guide 200.

Figure 3:
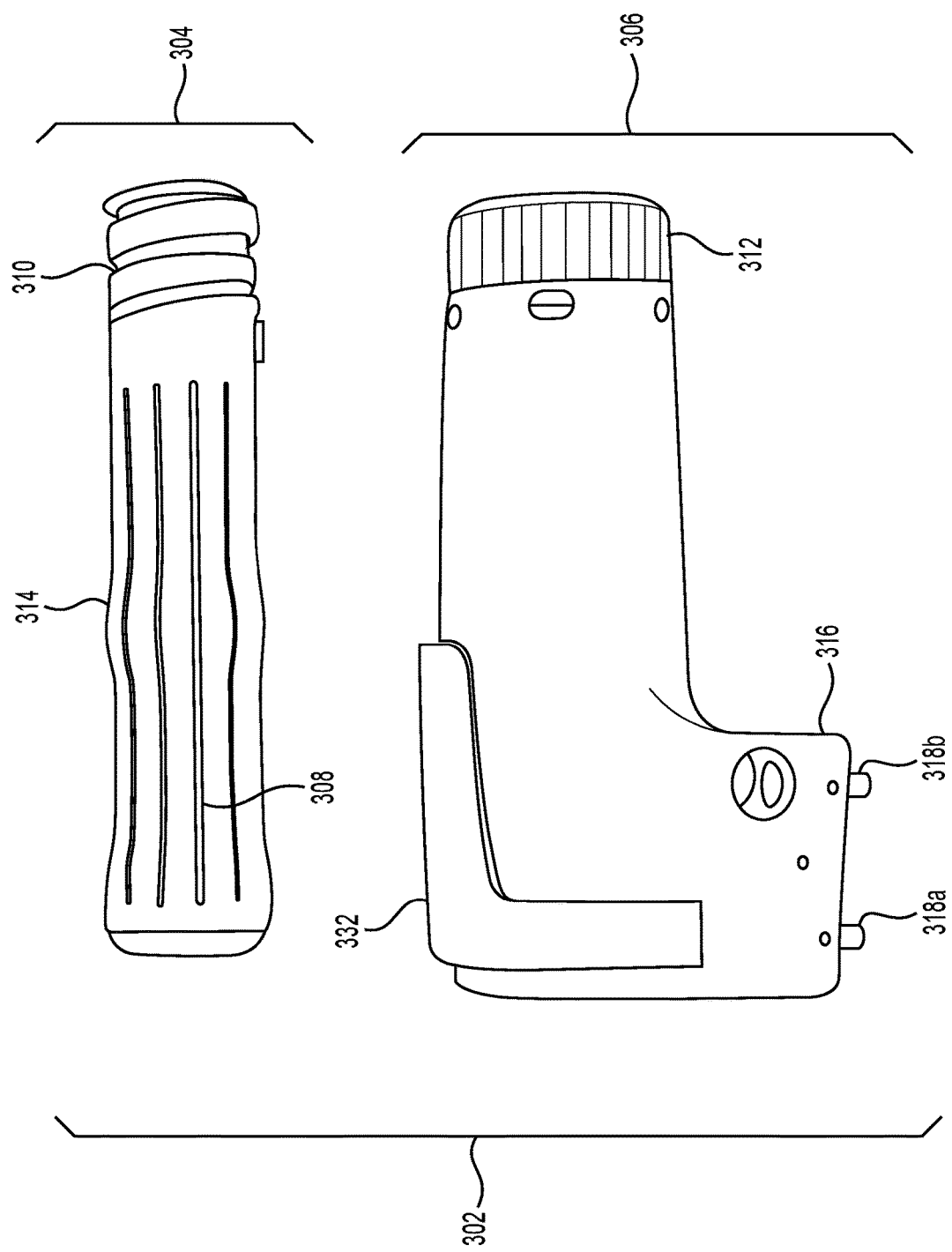
FIG. 3 is an illustration of a sterile handle and tightening sleeve, according to an illustrative embodiment of the invention.

FIG. 3 shows a sterile handle mounting on a support member (e.g., 240) of a universal instrument guide for use with a robotic surgical system. In some implementations, the sterile handle 302 includes a tightening sleeve 304 with a hollow tubular structure having a first open end. In some implementations, the structure of the tightening sleeve 304 defines an axis along which a portion of the support member (e.g., 240) may be inserted into the tightening sleeve 304.

A sterile handle housing 306 may include a hollow tubular structure having a first open end. The sterile handle housing 306 structure may defining an axis along which the tightening sleeve 304 may be inserted into the sterile handle housing 306.

The tightening sleeve 304 may include two or more openings along a length of the tightening sleeve allowing the tightening sleeve to mechanically flex under tension. In some implementations, the two or more openings are two or more slots, holes, or perforations.

A tightening nut 312 may be permanently and removably coupled to the sterile handle housing 306. The tightening nut 312 includes a thread on an interior of the tightening nut. The tightening nut 312 is configured to engage a thread 310 on exterior of the tightening sleeve 304 and thereby tighten the tightening sleeve 304 such that a diameter of a portion of the tightening sleeve decreases and securely holds a portion of a support member 240 inserted into the tightening sleeve 304. The tightening sleeve 304 includes a wedge 314 that engages a wedge on the interior of the sterile handle housing 306 as the tightening nut 312 is tightened and the threads inside the tightening nut 312 engage the threads 310 on the tightening sleeve 304 and pull the tightening sleeve in the direction of the tightening nut 312. The wedges force the tightening sleeve to flex and increase the friction between the portion of the support member 240 and the tightening sleeve 304 when the sterile handle 302 is assembled with the portion of the support member 240 inserted into the tightening sleeve 304. Thus, tightening the tightening nut 312 enables the sterile handle to securely hold the universal surgical instrument guide.

In some implementations, the sterile handle 302 includes an electrical assembly 316. The electrical assembly 316 may include one or more input devices 318 for commanding the robotic surgical system. The one or more input devices 318 may include two or more buttons 318*a* and 318*b* configured to enable a user to place the robotic surgical system in one of a rotation mode, a translation mode, or a combined translation and rotation mode. In some implementations, upon selection of a first button 318*a* of the two or more buttons, the robotic surgical system is in the rotation mode, upon selection of a second button 318*b* of the two or more buttons, the robotic surgical system is in the translation mode, and upon selection of both the first and second buttons 318*a-b*, the robotic surgical system is in the combined translation and rotation mode. In some implementations, the handle 302 and input device(s) thereon (e.g., buttons) can be used for instructing the robotic system to translate along a line when the translation button is pressed, rotate around the line if the rotation button is pressed, and/or translate and rotate around the line if both buttons are pressed.

The electrical assembly 316 may be directly integrated into the sterile handle 302. In some implementations, the electrical assembly 316 can be done separately (e.g., using overmolding on buttons and cable or epoxy resin to form an assembly which is integrated into the handle using a rapid locking system).

In some implementations, the sterile handle 302 is ambidextrous. In some implementations, the sterile handle 302 is configured such that a robotic surgical system may be used on either side of an operating table when the handle 302 is in use. The sterile handle is configured to be attached directly or indirectly to an end-effector of the robotic surgical system. In some implementations, the robotic surgical system is configured to allow robotically-assisted or unassisted positioning and/or movement of the sterile handle by a user with at least six degrees of freedom. The six degrees of freedom may be three degrees of translations and three degrees of rotations.

The sterile handle 302 may be completely or partially disposable. For example, in some implementations, the electrical assembly 316 may be disposable. All disposable parts may be produced in molded plastic. In some implementations, reusable parts may be made of either metal or plastic. In some implementations, the entire sterile handle 302 is reusable. Assembly of the sterile handle 302 may be performed pre-operatively. For example, a disposable sterile handle 302 may be completely assembled in the packaging. In some implementations, the sterile handle 302 may be assembled intra-operatively. In some implementations, the electrical assembly 316 may be fixed in the handle before mounting the sterile handle 302 on the universal surgical instrument guide.

The sterile handle 302 may be made of a sterile material or a material that may be sterilized. In some implementations, the sterile handle 302 may be sterilized using different technologies, such as using Ethylene Oxide (EtO), autoclave, radiation, or other sterilization methods. Different components of the sterile handle 302 using different technologies, for example, mechanical assembly in an autoclave, electrical assembly in an EtO. In some implementations, sterilization is achieved by draping. In some implementations, the sterile handle comprises one or more sensors configured to detect a presence of a surgeon's hand in proximity to the sterile handle. In some implementations, the one or more sensors include a presence detector 332 that is engaged by a surgeon's hand when the surgeon holds the handle such that presence of the hand is detected. The presence detector may be a lever-button detector. In some implementations, the presence detector 332 includes one or more capacitive or resistive sensors, or a combination thereof.

Referring again to FIG. 2, navigation marker 210 is attached to universal surgical instrument guide using a fastener inserted into an opening in the body of universal surgical instrument guide 200 sized and shaped to receive such a fastener. Navigation marker 210 can be any navigation marker suitable for tracking the position of a universal surgical instrument guide. Navigation marker 210 comprises three navigation member elements that can be used to triangulating the position of the universal surgical instrument guide with high precision. In certain embodiments, a navigation marker may have more or less constituent navigation member elements (e.g., 2 or 4). In certain embodiments, the position of a navigation marker is tracked using a navigation camera, wherein the navigation camera is part of a robotic surgical system. In some embodiments, a navigation marker has more or less navigation member elements. Navigation marker 210 is located on the opposite side of universal surgical instrument guide 200 from handle support member 240 to reduce the likelihood of the support member, any sterile handle attached thereto, and any part of a surgeon's body near the sterile handle during use from interfering with tracking of navigation marker 210.

Fasteners used to attach navigation marker 210 or handle support member 240 to universal surgical instrument guide body or to attach the universal surgical instrument guide body to a robotic arm (i.e., fastener 220) may be any fastener suitable to securely hold the respective components together. For example, the fastener may be an expansion fastener, screw, bolt, peg, flange or similar.

Figure 5:
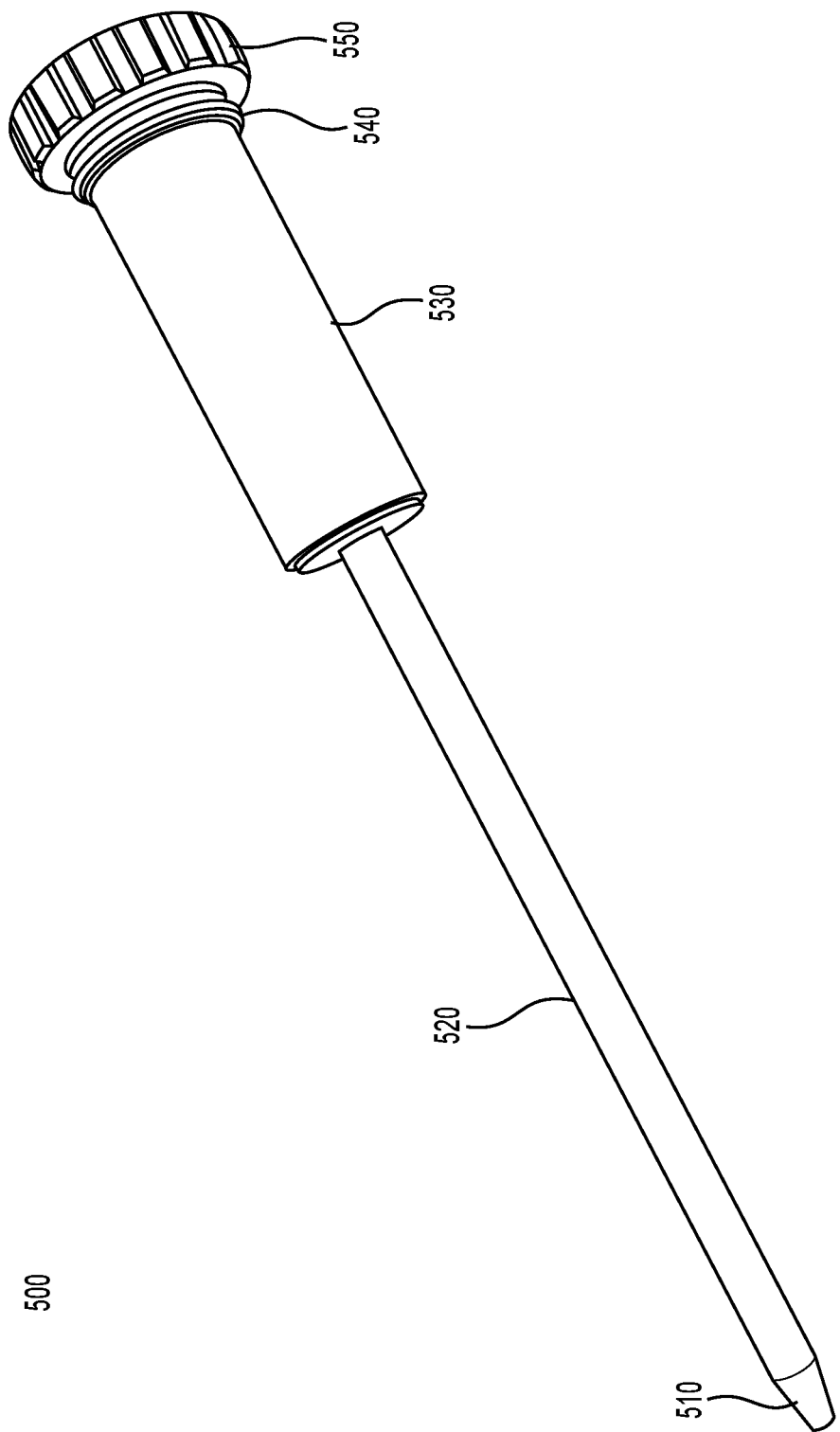
FIG. 5 shows a drill guide, according to an illustrative embodiment of the invention.

FIG. 5 shows a drill guide 500 engineered for use with a universal surgical instrument guide (e.g., the guide 200 of FIG. 2). Drill guide 500 comprises tapered end 510, guiding shaft 520, and a proximal portion comprising first exterior surface 530, second exterior surface 540, and collar 550. Guiding shaft 520 is sized such that the hollow internal portion of the shaft is of appropriate size to accommodate the stem of a drill bit. Guiding shaft 520 runs from tapered end 510 to the terminal aspect of the collar such that a drill bit enters drill guide 500 at an opening near collar 550 and exits drill guide 500 at tapered end 510 with its movement restricted along an axis along the long dimension of guiding shaft 520. First exterior surface 530 is substantially in contact with a second channel (e.g., 230) of a universal surgical instrument guide when drill guide 500 is inserted therein such that drill guide 500 cannot be easily deflected. Furthermore, threads on second exterior surface 540 engage threads (e.g., 232) of the universal surgical instrument guide's second channel such that drill guide 500 is securely held by the universal surgical instrument guide. Collar 550 can be gripped by a surgeon to thread drill guide 500 into a universal surgical instrument guide and additionally acts as a limiter to prevent over-threading of drill guide 500.

Figure 6:
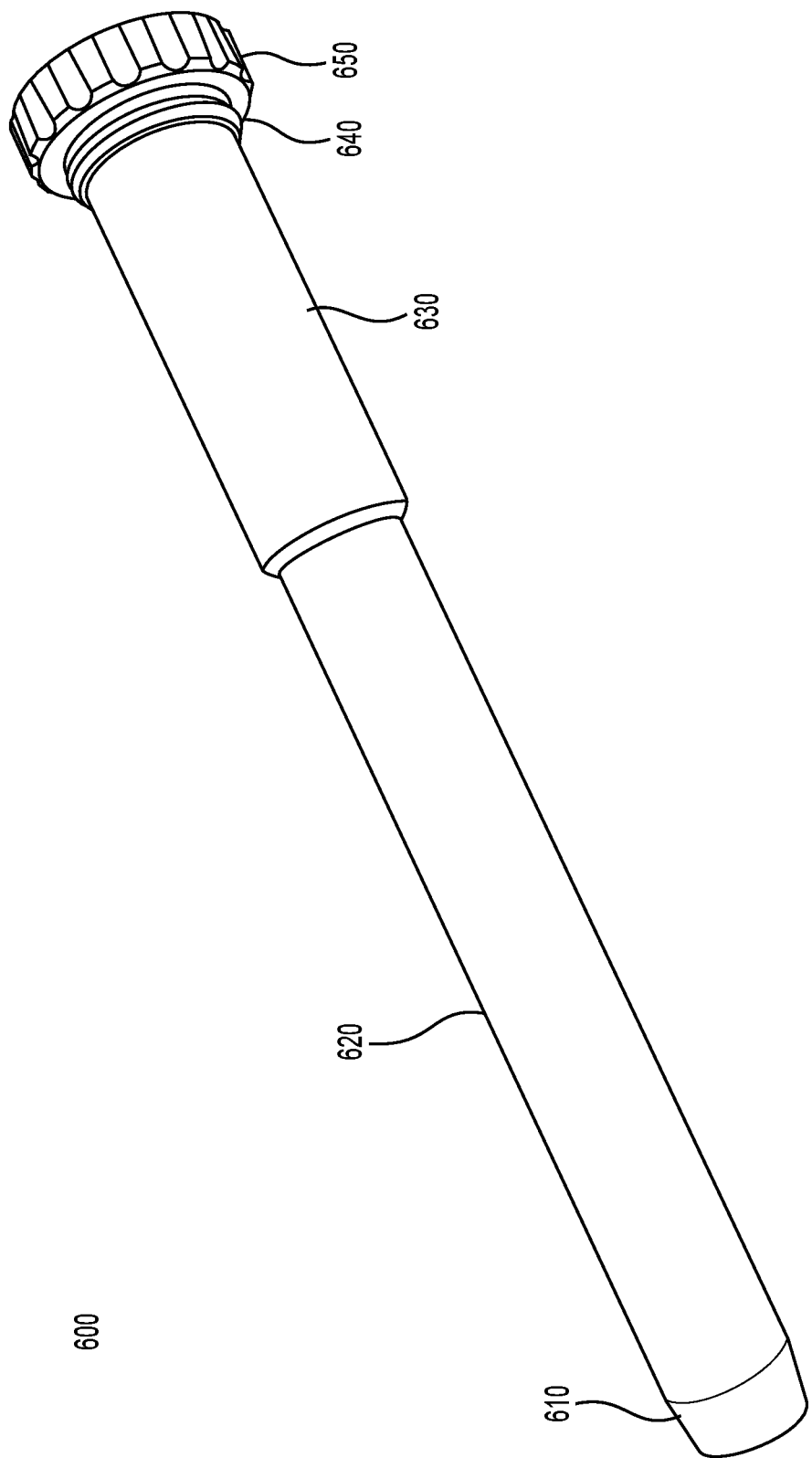
FIG. 6 shows a master guide, according to an illustrative embodiment of the invention.

FIG. 6 shows a master guide 600 engineered for use with a universal surgical instrument guide (e.g., the guide of FIG. 2). Master guide 600 comprises tapered end 610, guiding shaft 620, and a proximal portion comprising first exterior surface 630, second exterior surface 640, and collar 650. Guiding shaft 620 is sized such that the hollow internal portion of the shaft is of appropriate size to accommodate additional surgical instrument guides (e.g., for use with narrower instruments) as well as dilators. Guiding shaft 620 runs from tapered end 610 to the terminal aspect of the collar 650 such that a surgical instrument or surgical instrument guide enters master guide 600 at an opening near collar 650 and exits master guide 600 at tapered end 610 with its movement restricted along an axis along the long dimension of guiding shaft 620. In some embodiments, a second surgical instrument guide is inserted into guiding shaft 620, wherein the second surgical instrument is of a length such that the distal end of the second surgical instrument guide terminates in substantially the same plane defined by the terminal aspect of tapered end 610. First exterior surface 630 is substantially in contact with a second channel (e.g., 230) of a universal surgical instrument guide when master guide 600 is inserted therein such that master guide 600 cannot be easily deflected. Furthermore, threads on second exterior surface 640 engage threads of the universal surgical instrument guide's second channel (e.g., 230) such that master guide 600 is securely held by the universal surgical instrument guide. Collar 650 can be gripped by a surgeon to thread master guide 600 into a universal surgical instrument guide and additionally acts as a limiter to prevent over-threading of master guide 600.

Figure 7:
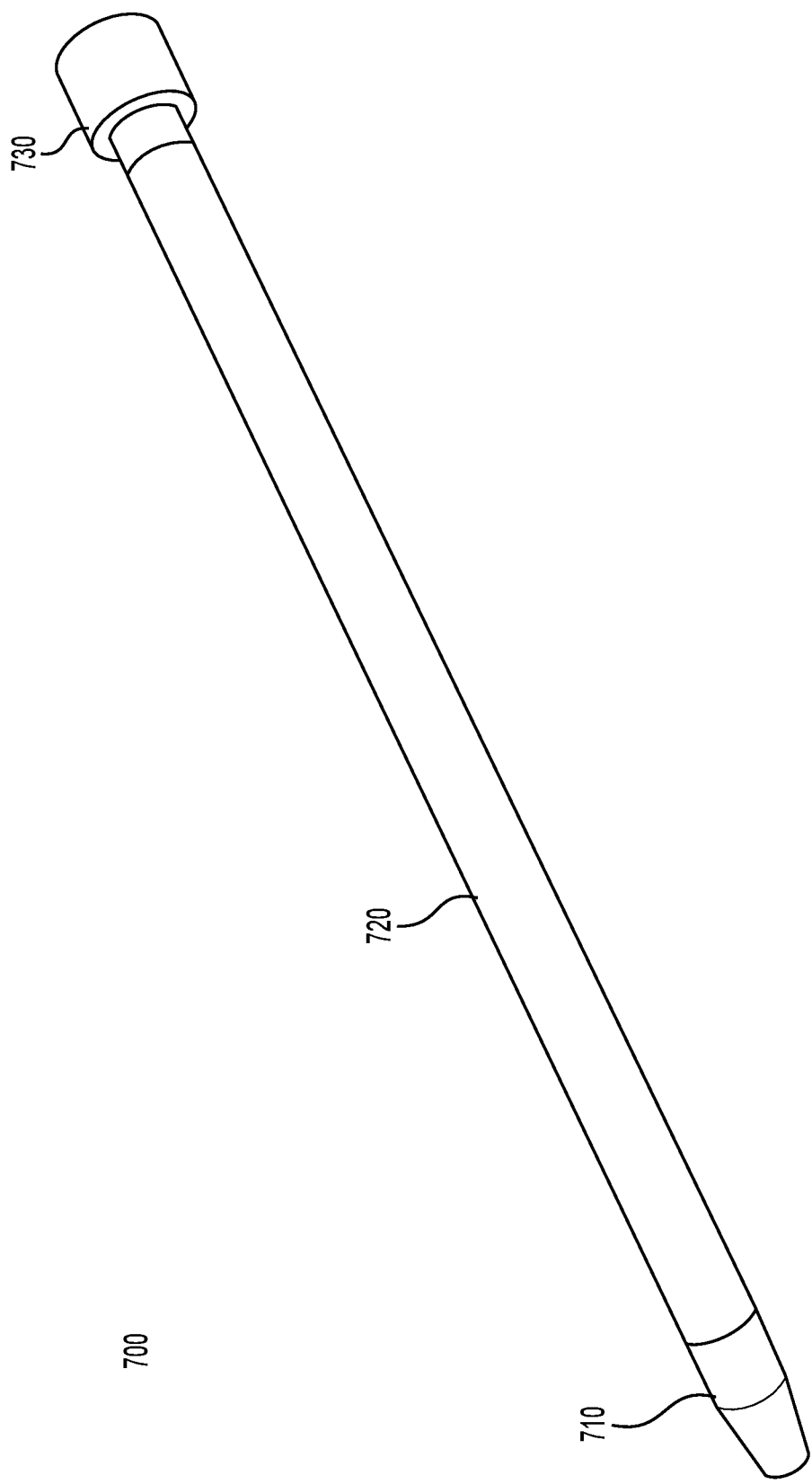
FIG. 7 shows a tubular dilator, according to an illustrative embodiment of the invention.

FIG. 7 shows a tubular dilator 700 engineered for use with a master guide (e.g., the master guide of FIG. 6). Tubular dilator 700 comprises tapered end 710, guiding shaft 720, and collar 730. Guiding shaft 720 is sized to be accommodated by the hollow internal portion of the guiding shaft of a master guide. Guiding shaft 720 additionally has a hollow internal portion sized for accommodating the stem of a rod dilator therein. A surgeon can grip tubular dilator 700 using collar 730.

Figure 8:
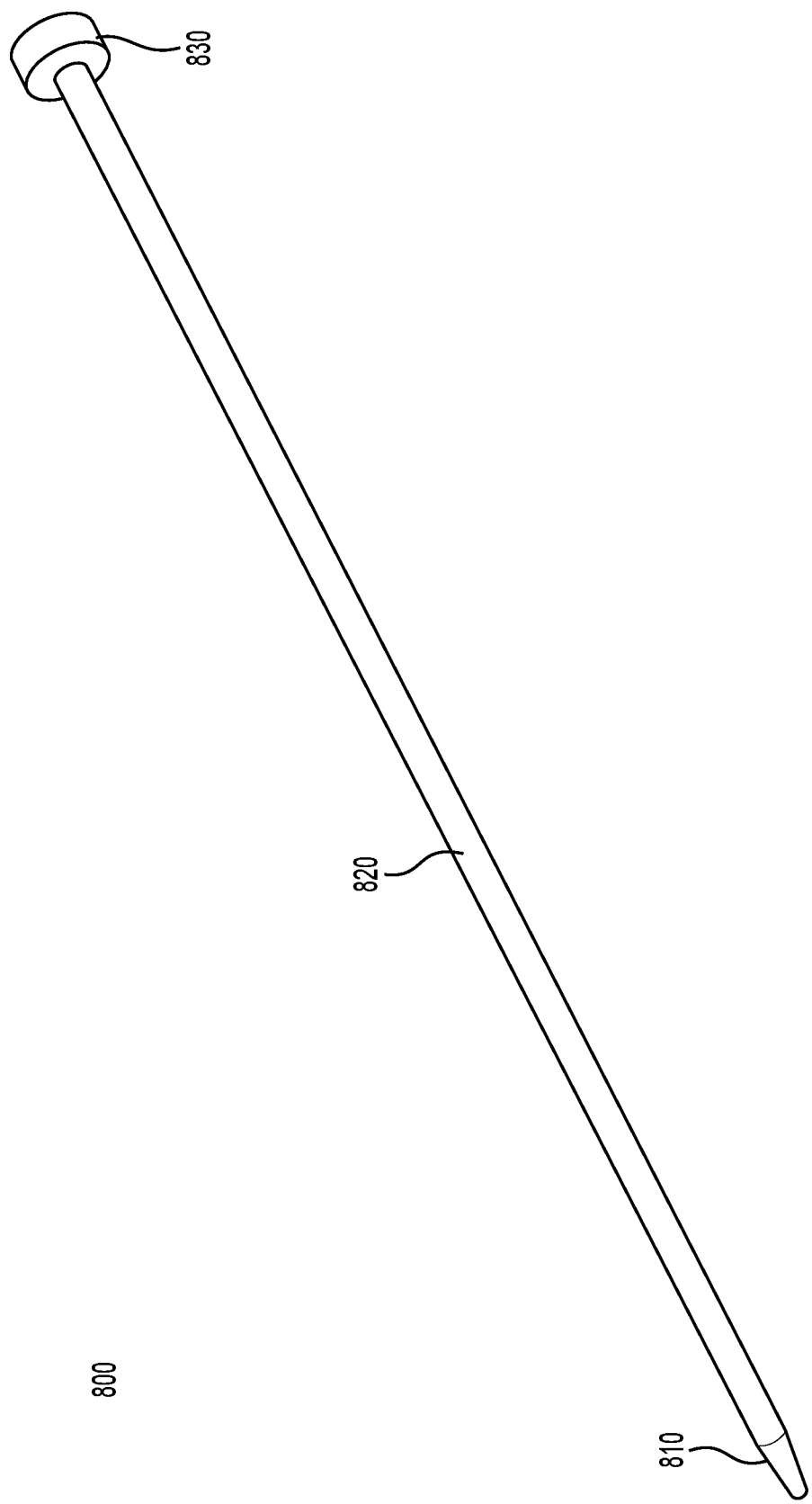
FIG. 8 shows a rod dilator, according to an illustrative embodiment of the invention.

FIG. 8 shows a rod dilator engineered for use with a tubular dilator (e.g., the tubular dilator of FIG. 7). Rod dilator 800 comprises tapered end 810, rod 820, and collar 830. Rod 820 is sized to be accommodated within the hollow internal portion of the guiding shaft of a tubular dilator. A surgeon can grip rod dilator 800 using collar 830.

Figure 9:
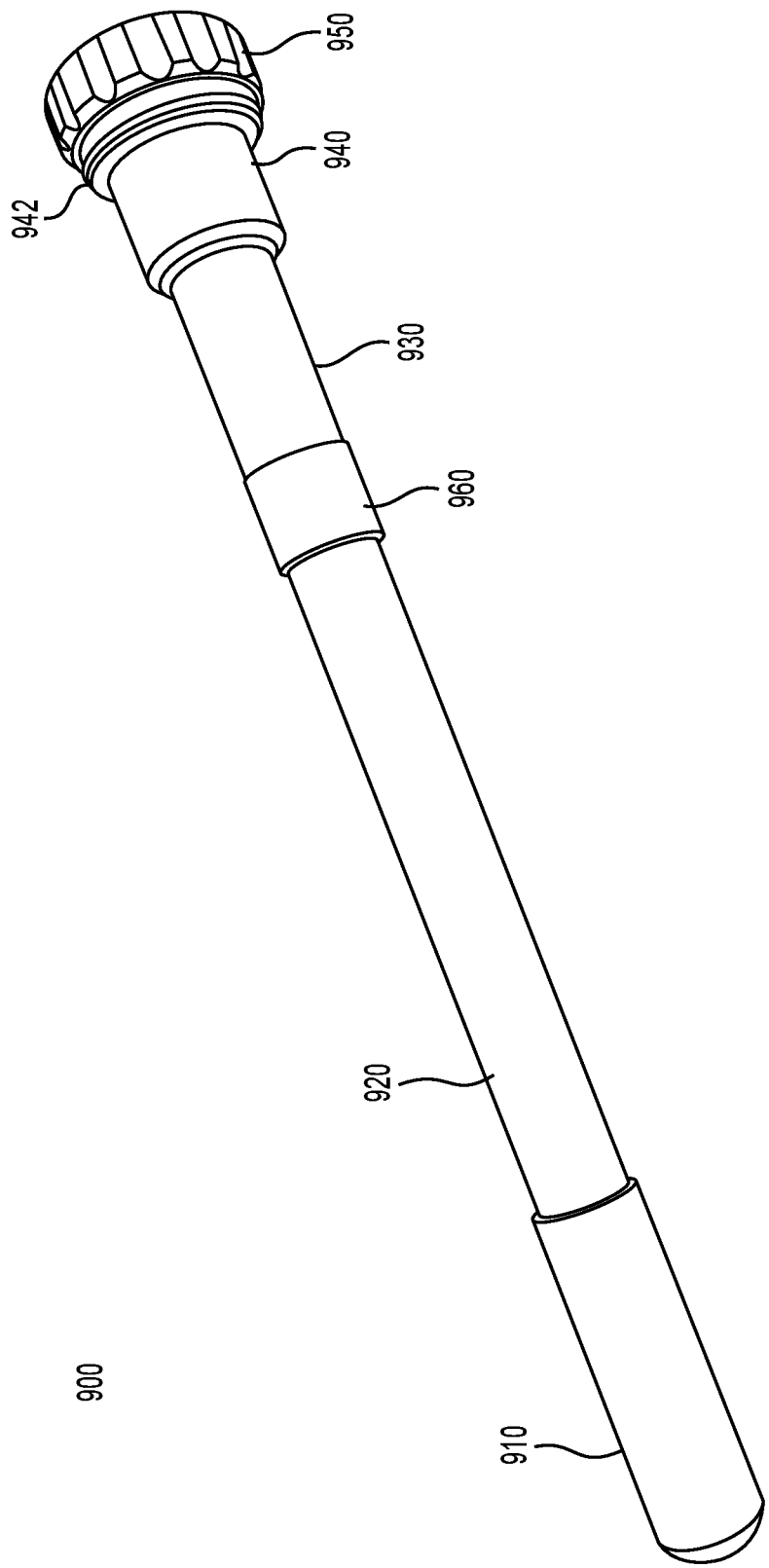
FIG. 9 shows a surgical tap guide, according to an illustrative embodiment of the invention.

FIG. 9 shows a surgical tap guide engineered for use with a master guide (e.g., the guide of FIG. 6). Surgical tap guide 900 comprises stabilizing ends 910 and 960, shaft 920, and a proximal portion comprising first exterior surface 930, second exterior surface 940, and collar 950. Shaft 920 is sized such that the hollow internal portion of the shaft is of appropriate size to accommodate the stem of a surgical tap guide therein. In certain embodiments, the diameter of the hollow internal portion of the shaft 920 is larger than the diameter of the hollow internal portions of stabilizing ends 910 and 960. In certain embodiments, the hollow internal portions of stabilizing ends 910, 930, and 960 are of appropriate size to accommodate the stem of a surgical tap therein. Shaft 920 runs from stabilizing end 910 to the terminal aspect of the collar such that a surgical tap enters surgical tap guide 900 at an opening near collar 950 and exits surgical tap guide 900 at stabilizing end 910 with its movement restricted along an axis along the long dimension of shaft 920. In certain embodiments, this movement is restricted by the hollow internal portions of the stabilizing ends 910 and 960, by the hollow internal portions of stabilizing ends 910 and 960 and the hollow internal portion of the first exterior surface 930, or by the hollow internal portions of stabilizing end 910 and the hollow internal portion of the first exterior surface 930. Stabilizing ends 910 and 960 are substantially in contact with the internal surface of the guiding shaft of a master guide when surgical tap guide 900 is inserted therein such that surgical tap guide 900 cannot be easily deflected. Stabilizing ends 910 and 960 can be of a larger exterior diameter than the shaft 920 and/or first exterior surface 930. Threads 942 on second exterior surface 940 engage threads of the internal surface of the shaft of a master guide such that surgical tap guide 900 is securely held by the master guide. Collar 950 can be gripped by a surgeon to thread surgical tap guide 900 into a master guide and additionally acts as a limiter to prevent over-threading of surgical tap guide 900. In some embodiments, a surgical tap guide may be sized to be attached to a universal surgical instrument guide (i.e., without using a master guide).

Figure 10:
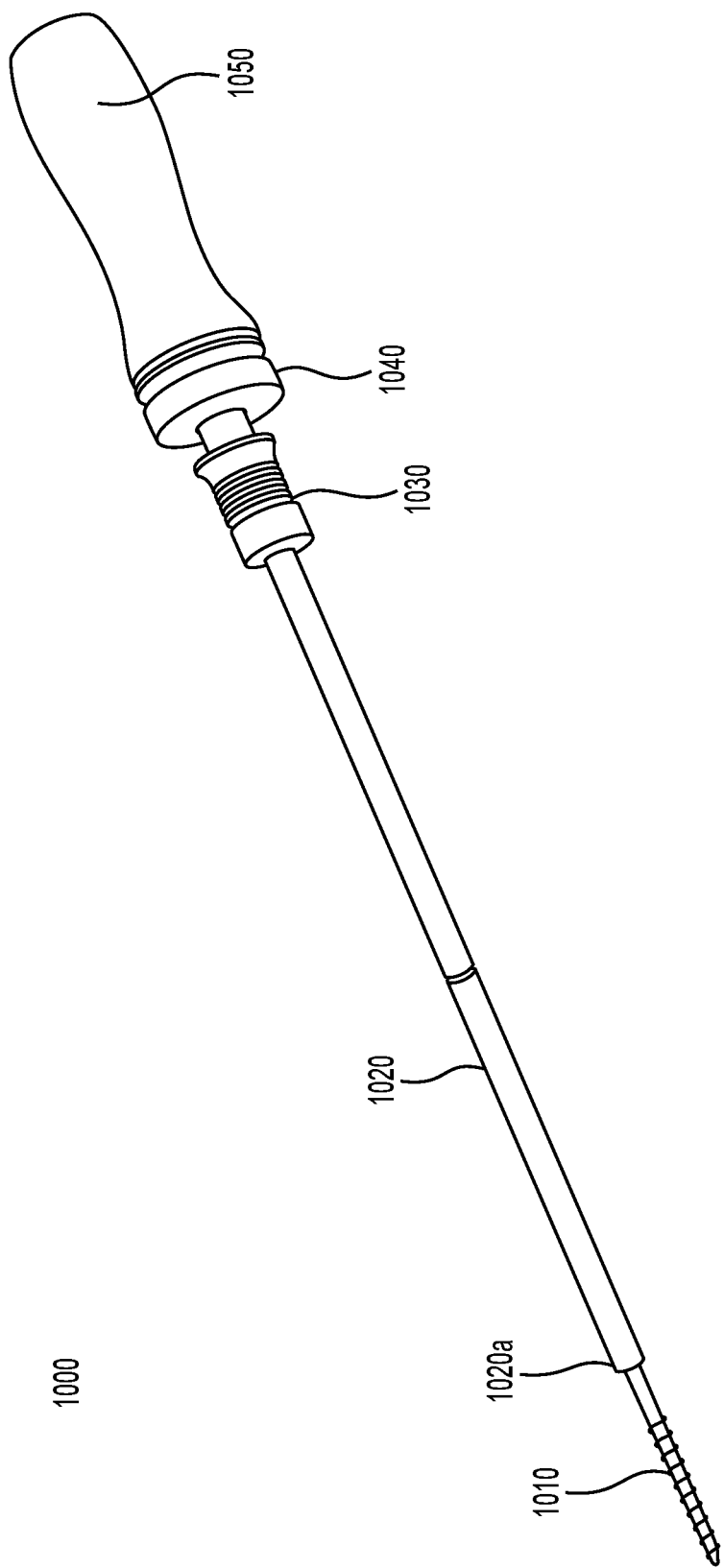
FIG. 10 shows a surgical tap, according to an illustrative embodiment of the invention.

FIG. 10 shows a modified surgical tap engineered for use with a surgical tap guide (e.g., the surgical tap guide of FIG. 9). In certain embodiments, a standard commercially available surgical tap may be modified for use with a surgical tap guide described herein (e.g., the surgical tap guide of FIG. 9). In general, a commercial surgical tap's shoulder or collar may need to be adapted to be of the appropriate diameter for use with a surgical tap guide. In some embodiments, no modification of the surgical tap is necessary. Surgical tap 1000 comprises tap end 1010, stem 1020, shoulder 1030, locking ring 1040, and grip 1050. Tap end 1010 is used for creating threads in a hole drilled in bone in order to retain a screw. Shoulder 1030 limits the distance surgical tap 1000 may be inserted into a surgical tap guide. Stem 1020 is sized in length such that when shoulder 1030 limits surgical tap 1000 from further insertion by contacting a portion of the surgical tap guide, distal end 1020a of stem 1020 is flush with the terminal aspect of the surgical tap guide. Locking ring 1040 engages a ratchet that limits the modified surgical tap to being driven either in or out from a drilled hole. The surgeon can grip the surgical tap with grip 1050.

Figure 11:
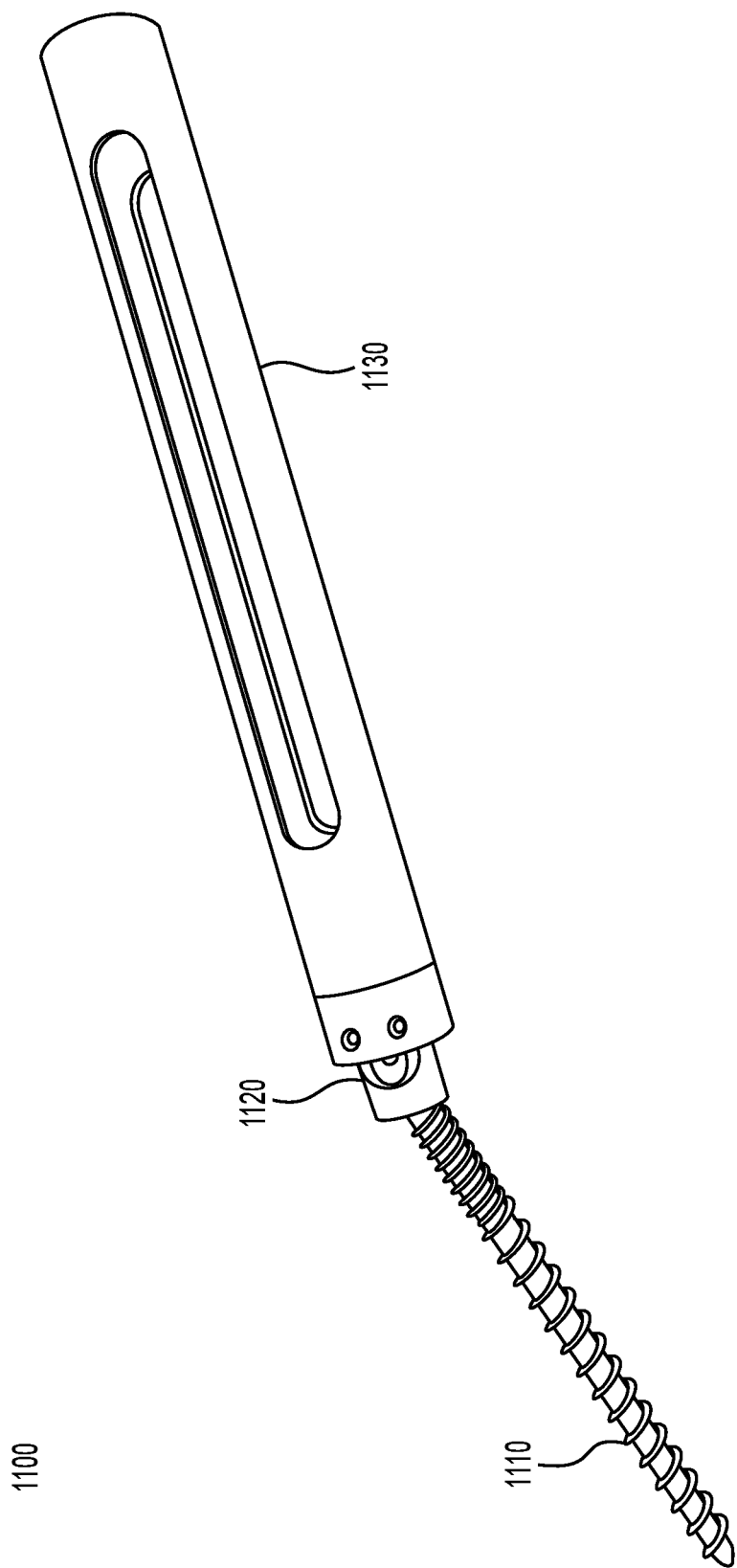
FIG. 11 shows a screw with screw extender, according to an illustrative embodiment of the invention.

FIG. 11 shows a surgical screw with screw extender engineered for use with a master guide (e.g., the master guide of FIG. 6). Surgical screw 1110 is releasably attached to screw extender 1130 at attachment point 1120. Screw extender 1130 is sized to be accommodated within the hollow internal portion of the guiding shaft of a master guide. Screw extender 1130 has a hollow structure such that a screwdriver can be accommodated within in order to contact the head of screw 1110 in order to drive it into the drilled and tapped hole in a patient's bone.

The surgical instruments, surgical instrument guides, and universal surgical instrument guides described herein are constructed from medical grade materials. In certain embodiments, components of the instruments and guides described herein that will not come in contact with the patient are constructed of medical grade plastic. Any plastic should be easily sterilizable for reuse of the instruments. In some embodiments, the surgical instruments are disposable. Components of the instruments and guides described herein that contact the patient are made of metal. For example, they made be made of stainless steel, titanium, tantalum, cobalt-chromium, or alloys thereof. In certain embodiments, all components and aspects of a universal surgical instrument system are made of or housed with metal.

The surgical instruments and surgical instrument guides described herein may be engineered to have a range of cross-sections. In certain embodiments, the second channel of a universal surgical instrument guide has a circular cross-section and, consequently, surgical instruments and surgical instrument guides for use therewith have circular cross-sections as well. Surgical instruments and surgical instrument guides with circular-cross section are substantially cylindrical in shape. In some embodiments, elliptical or other curved cross-sections are used. Requirements arising from the type of procedures to be performed may dictate what shape cross-section is appropriate for a particular universal surgical instrument system.

FIGS. 18A and 18B are illustrations of a universal surgical instrument guide attached to a robotic arm with an overlay of a coordinate system used to define a tool center point (TCP) that facilitates precise positioning and trajectory planning for surgical instrument guides and surgical instruments inserted through the universal surgical instrument guide. Universal surgical instrument guide 1820 is attached indirectly to robotic arm 1830. Sterile handle (i.e., manipulator) 1810 is mounted on a support member (e.g., 240) of universal surgical instrument guide 1820. Surgical instrument guide 1840 is inserted into universal surgical instrument guide 1820. Surgical instrument guide 1840 is engineered such that when inserted into universal surgical instrument guide 1820, there is a defined tool center point 1850 with known coordinates relative to robotic arm 1830. The origin of a coordinate system used to define the tool center point may be located at a flange of a robotic arm. It may additionally be located at any convenient to define point such as an interface, joint, or terminal aspect of a component of a robotic surgical system.

Other surgical instrument guides engineered for use with universal surgical instrument guide 1820 and surgical instrument guide 1840 will have terminal ends that end at tool center point 1850. For example, when a master guide is inserted into universal surgical instrument guide 1820, another guide such as a surgical tap guide may additionally be inserted into universal surgical instrument guide 1820 by inserting the surgical tap guide into the previously inserted master guide. The surgical tap guide and master guide are engineered such that the distal (relative to the universal surgical instrument guide) end of the guiding shafts of both guides terminates at substantially the same plane, wherein said plane contains the tool center point such that the tool center point is located at approximately a center point of the cross sections of the guides. A surgical instrument inserted into one or more guides inserted into universal surgical instrument guide 1820 will be constrained in its movement along the axis defined by the long dimension of guiding shaft of the guides such that the surgical instrument can move along the axis and exits the guides (e.g., to enter a surgical site) at the tool center point.

In certain embodiments, because the TCP is in a constant position relative to the robotic arm, regardless of whether a surgical guide or surgical instrument is being used with the universal surgical instrument guide, a surgeon can be provided visualization of the orientation, trajectory, and position of an instrument or instrument guide inserted into the universal surgical instrument guide. A navigation marker attached to universal surgical instrument guide 1820 can be used to track the position and orientation of the universal surgical instrument guide to update the position, orientation, and current trajectory based on manipulation of robotic arm 1830 by a surgeon using sterile handle 1810. Additional information provided by patient imaging (e.g., CT data, radio imaging data, or similar) taken pre- or intra-operatively as well as navigation markers attached to a patient's body may be combined with data from a navigation marker attached to a universal surgical instrument guide and displayed on a screen viewable by the surgeon such that the surgeon can see the location of necessary features of the patient's anatomy and the position, trajectory, and orientation of a surgical instrument or surgical instrument guide relative to said anatomy. The use of engineered universal surgical instrument systems eliminates the need for navigation markers to be attached to the end of surgical guides or tools in order to precisely determine the position, orientation, and trajectory of a surgical instrument guide relative to a patient's anatomy.

Figure 19:
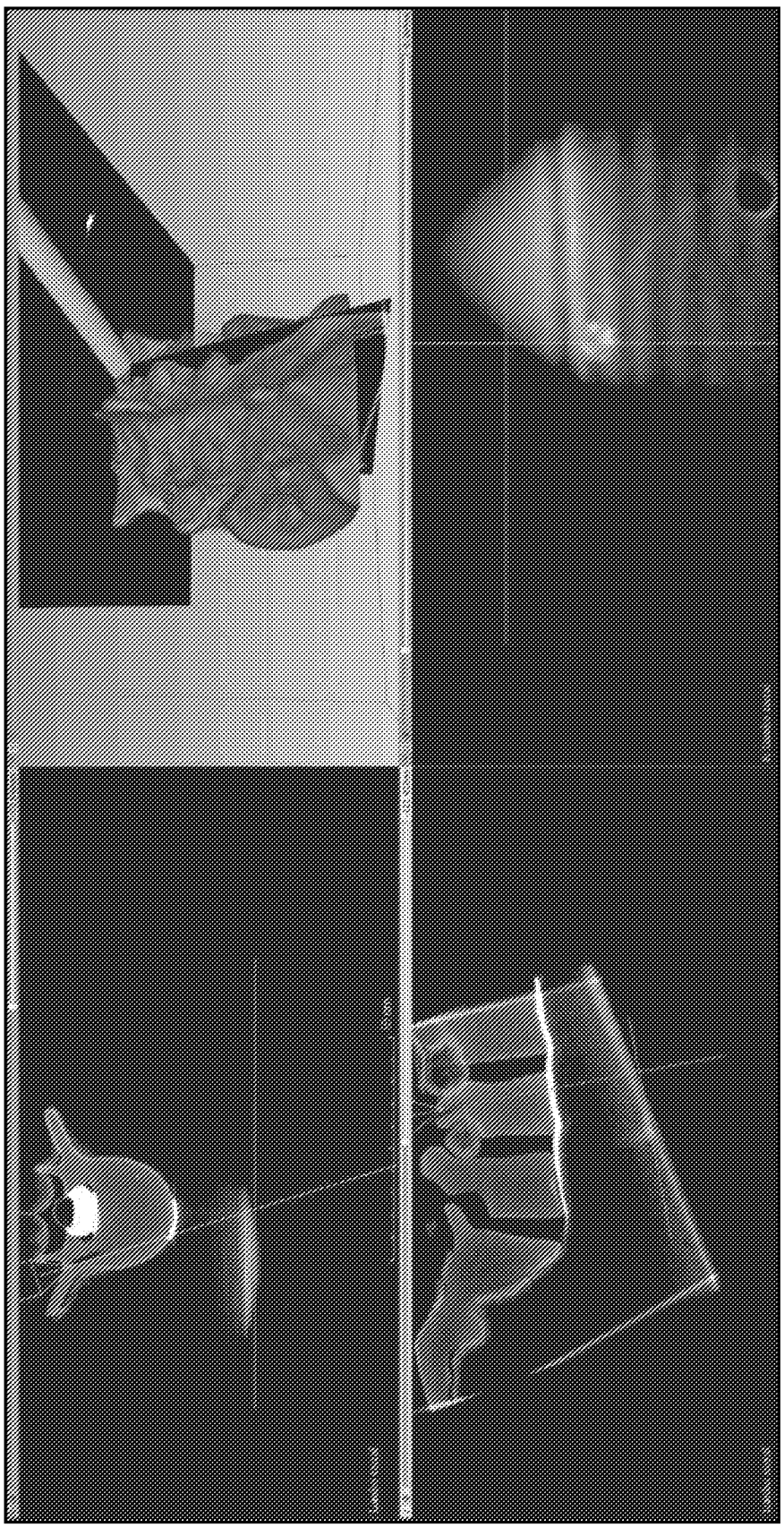
FIG. 19 shows a navigation screen that may be viewed by a surgeon or surgical staff during a spinal procedure in order to visualize the position, orientation, and trajectory of a surgical instrument guide relative to a patient's anatomy, according to an illustrative embodiment of the invention.

FIG. 19 shows an exemplary navigation screen as viewed by a surgeon or surgical staff during a spinal procedure. Three of the four panels show radio images of the patient's anatomy with an overlay showing the position of a surgical instrument guide with its tool center point highlighted and a line segment emanating from the tool center point demonstrating the current trajectory of the surgical instrument guide or any surgical instrument guided therethrough. The fourth panel shows a 3D reconstruction of the patient's spine with a rendering of the surgical instrument guide shown to further acclimate the surgeon and surgical staff to the current position, orientation, and trajectory of the surgical instrument guide. Such a display changes as the position or orientation of the universal surgical instrument guide are updated by manipulation of the robotic arm by the surgeon. The surgeon may consult the current projected trajectory, position, or orientation of the surgical instrument guide relative to the patient's anatomy to intraoperatively adjust the position of the robotic arm to update the trajectory, position, and/or orientation of surgical instrument guide (and any surgical instrument inserted therethrough).

Figure 20:
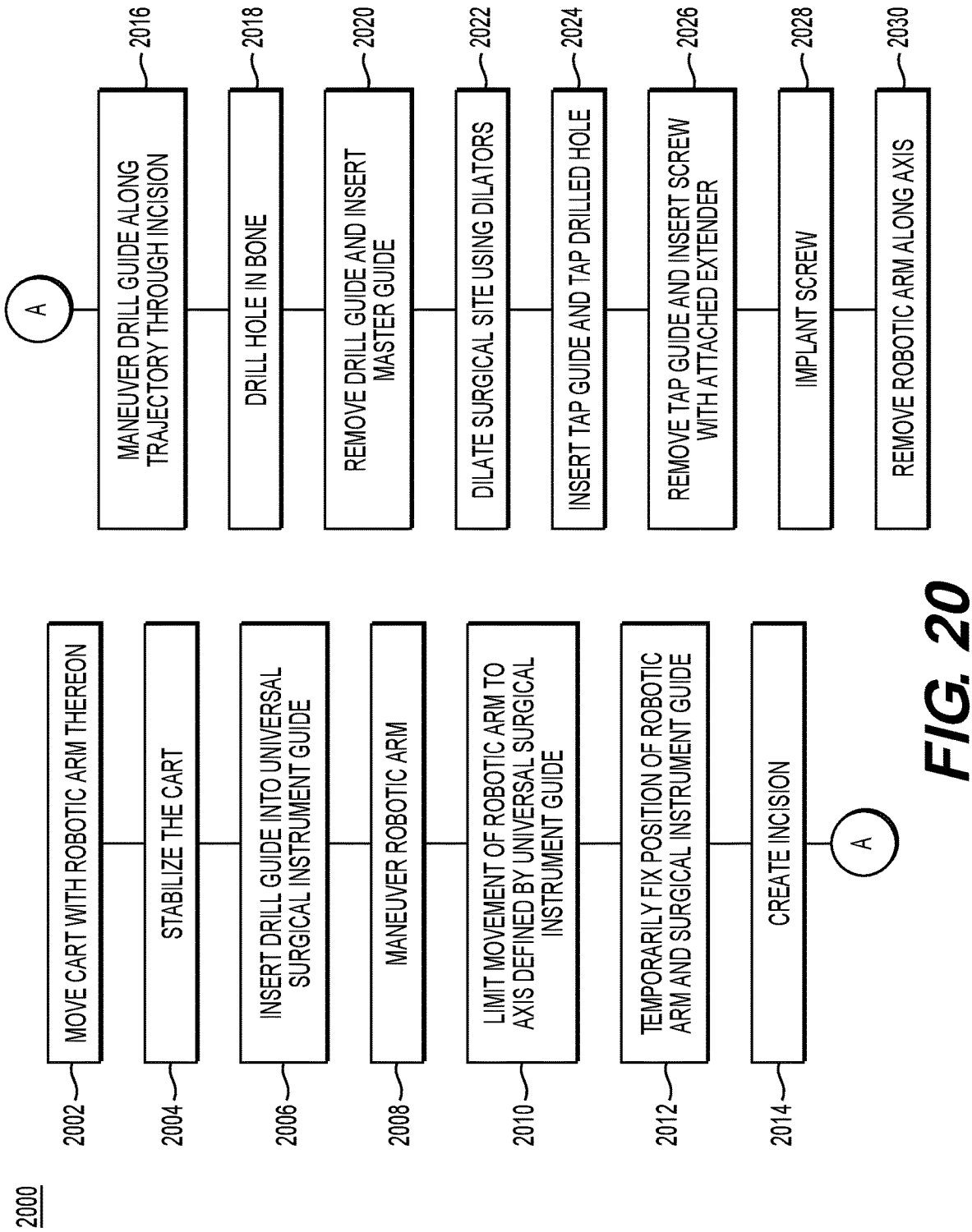
FIG. 20 is a block diagram of a method for performing surgery using a universal surgical instrument system, according to an illustrative embodiment of the invention.

FIG. 20 is a block diagram of a method for implanting a surgical screw with a releasable screw extender into a vertebra of a patient. FIGS. 21-52 show internal and external views of a patient during the method described in FIG. 20. Method 2000 involves the use of a universal surgical instrument system and a robotic surgical system mounted on a cart. The surgical procedure results in a screw (with screw extender) being placed in a vertebra of a patient. This procedure may be repeated several times, for example, in order to install a surgical rod for stabilization and alignment of the patient's spine.

Figure 12B:
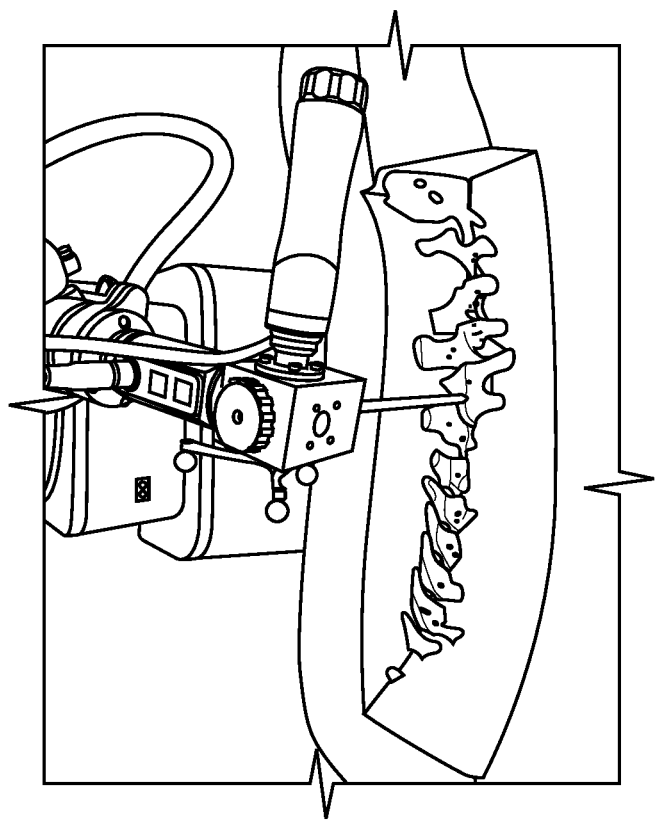
FIG. 12A and FIG. 12B show inserting a drill guide into a universal surgical instrument guide, according to an illustrative embodiment of the invention.
Figure 12A:
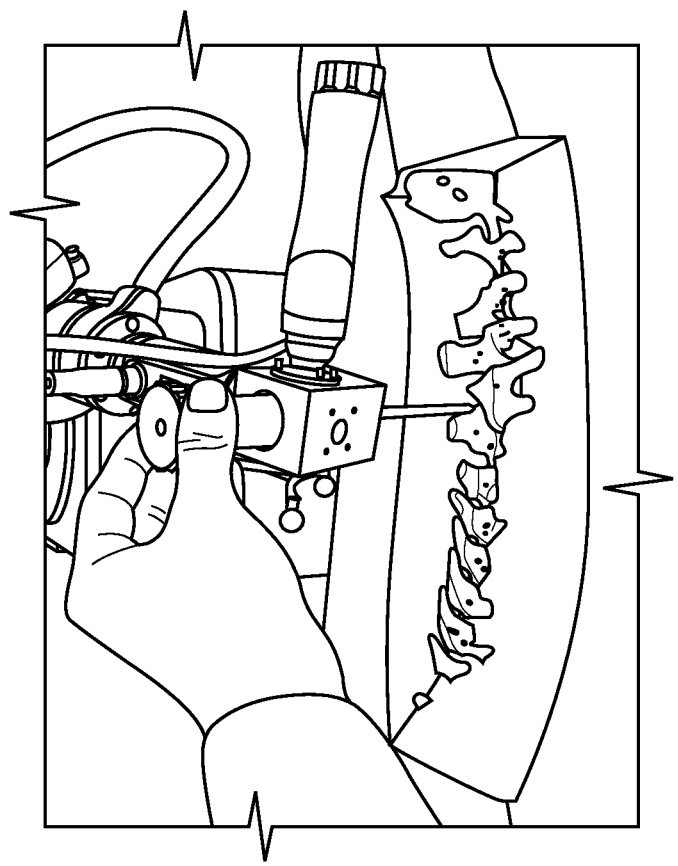

In step 2002, the cart holding on which a robotic arm is mounted is moved into a position in an operating room appropriate for performing the surgical procedure. A universal surgical instrument guide has been attached to the robotic arm (e.g., using an attachment system described herein above). In step 2004, the cart is stabilized after it is moved into position. In step 2006, a drill guide is inserted into the universal surgical instrument guide (see FIGS. 12A-12B for drill guide during and after insertion).

Figure 22:
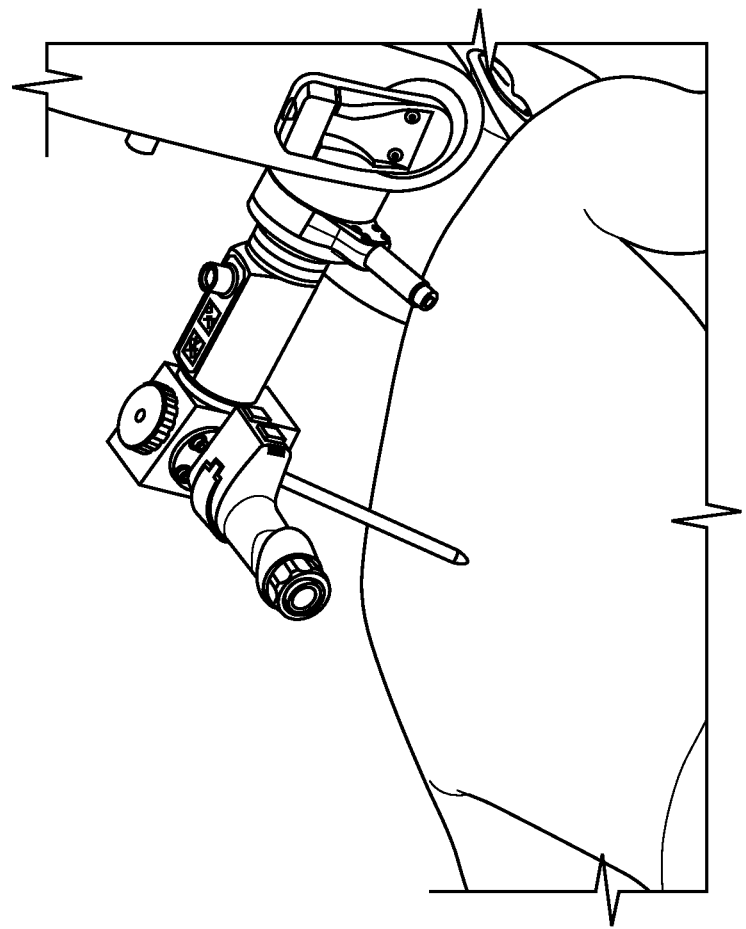
Figure 21:
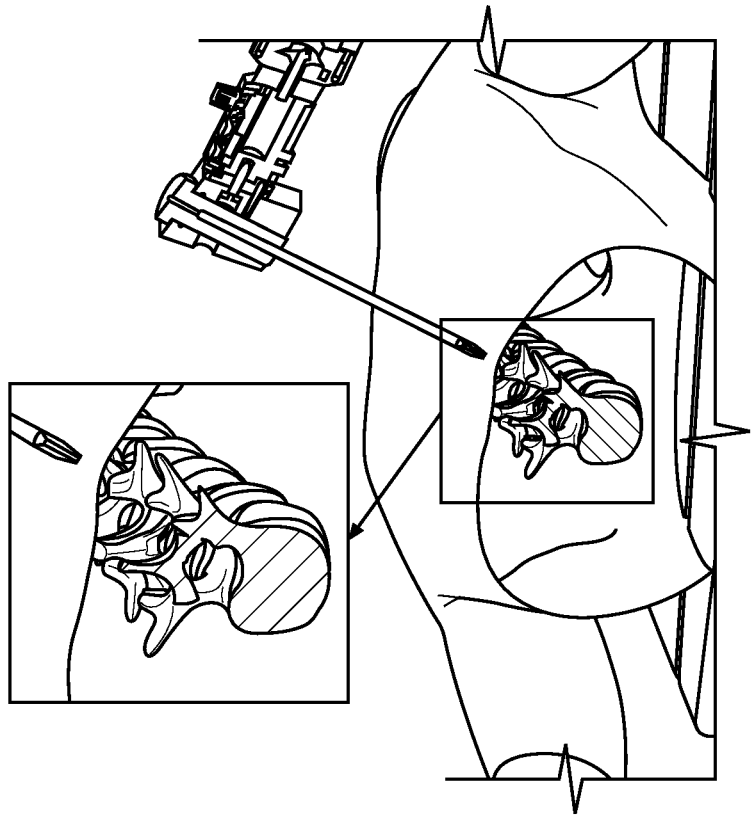

In step 2008 of method 2000, the surgeon maneuvers the robotic arm of the robotic surgical system into a desired position and orientation (i.e., such that a desired trajectory is achieved). In step 2008, the desired trajectory is one that allows access to the surgical site (i.e., the patient's vertebra). FIGS. 21 and 22 show two illustrations of a drill guide attached to a robotic arm by a universal surgical instrument guide oriented to follow a trajectory to a patient's vertebra. Maneuvering may be assisted by a navigation subsystem that uses a navigation marker attached to the universal surgical instrument guide, the tool center point defined for the universal surgical instrument system, and a display that visualizes the position, orientation, and trajectory of the drill guide relative to the patient's anatomy for the surgeon. The surgeon manipulates the robotic arm in step 2008 using a manipulator (i.e., sterile handle) having one or more inputs that limit the motion of the robotic arm. For example, the robotic arm may be able to move with six degrees of freedom while one input on the manipulator limits the motion to only translational degrees of freedom and another input on the manipulator limits the motion to only rotational degrees of freedom. Thus, the position and orientation of the universal surgical instrument guide can be independently updated.

In step 2010 of method 2000, the surgeon limits the movement of the robotic arm to an axis defined by the universal surgical instrument guide and the drill guide (e.g., by the channel of the universal guide through which the drill guide is inserted). The surgeon may press a button or other similar input on the manipulator or robotic arm to enter such a "trajectory" mode. Trajectory modes allow the surgeon to easily manipulate the robotic arm along a trajectory while preventing unwanted lateral movements. In this way, a surgeon's applied force cannot cause the orientation or trajectory of a surgical instrument guide to be altered while in a trajectory mode. Only once the trajectory mode has been exited (i.e., by pressing the button or similar again) can the robotic arm move freely along any trajectory.

In step 2012 of method 2000, the position of the robotic arm (and thus, the drill guide) is temporarily fixed. In certain embodiments, robotic surgical systems have activation sensors mounted on the manipulator such that the position of the robotic arm is fixed whenever the surgeon is not gripping the manipulator. The robotic arm may thus be temporarily fixed by releasing the activation sensor.

Figure 24:
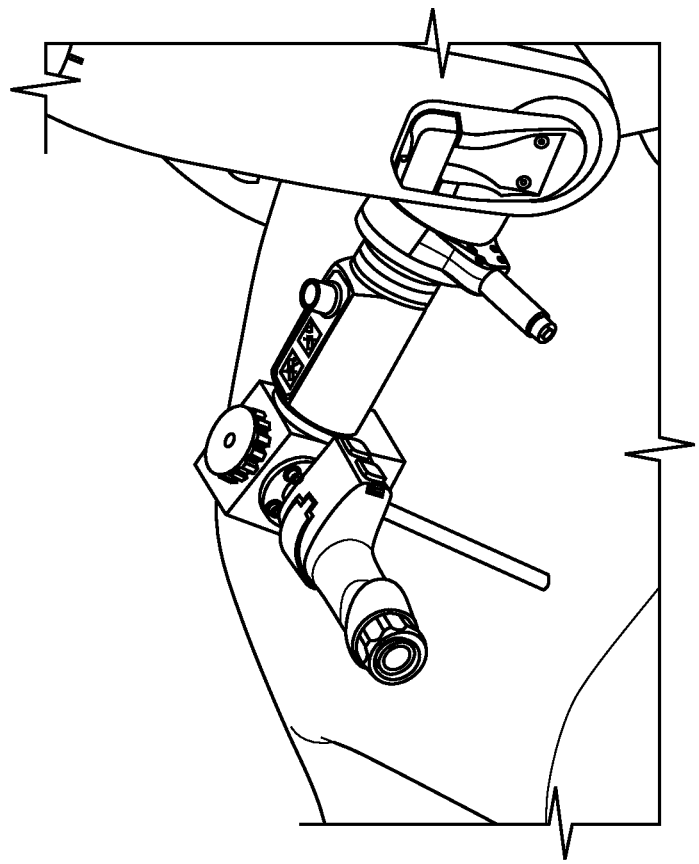
Figure 23:
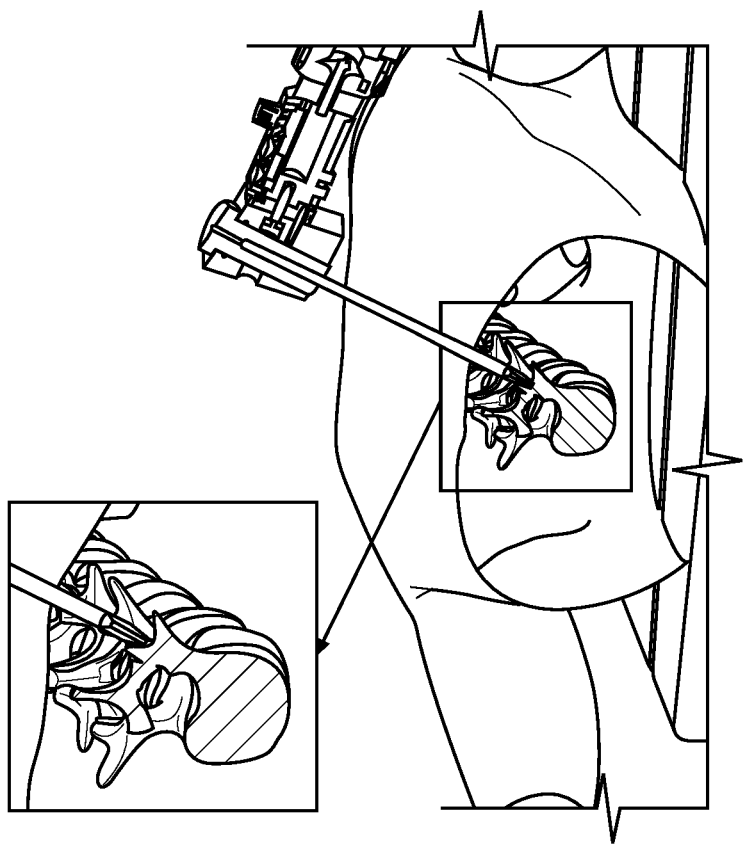

In step 2014, the surgeon creates an incision in the skin of the patient in order to access the vertebra with surgical instruments and surgical instrument guides. In step 2016, the surgeon unfixes the position of the robotic arm to maneuver the drill guide along the defined trajectory through the incision to the surgical site. FIGS. 23 and 24 show two illustrations of the drill guide that has been maneuvered to the surgical site (the patient's vertebra). The robotic arm being limited in its motion by the engagement of the trajectory mode ensures precise movement of the drill guide from outside the patient to the patient's vertebra. The surgeon may monitor the progress of the drill guide on the navigation display. Without a navigation display with a known precise location of the guide's tip, the surgeon would not be able to monitor the trajectory for accuracy during maneuvering in such a percutaneous approach. The robotic surgical system may comprise a force sensor that provides haptic feedback to the surgeon when contact is made with the bone to avoid excess pressure being applied.

Figure 25:
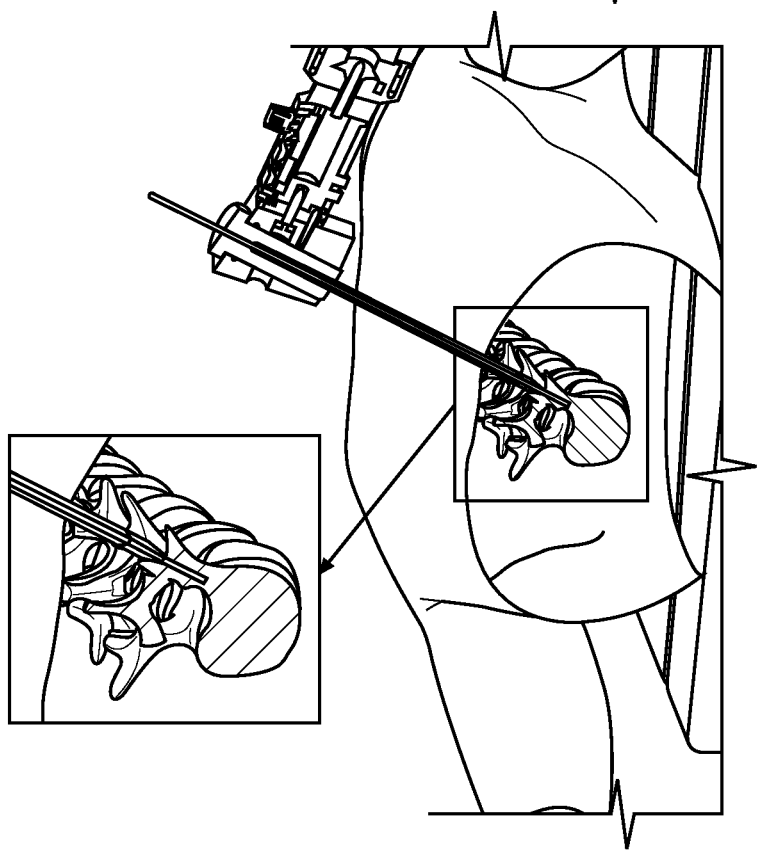
Figure 26:
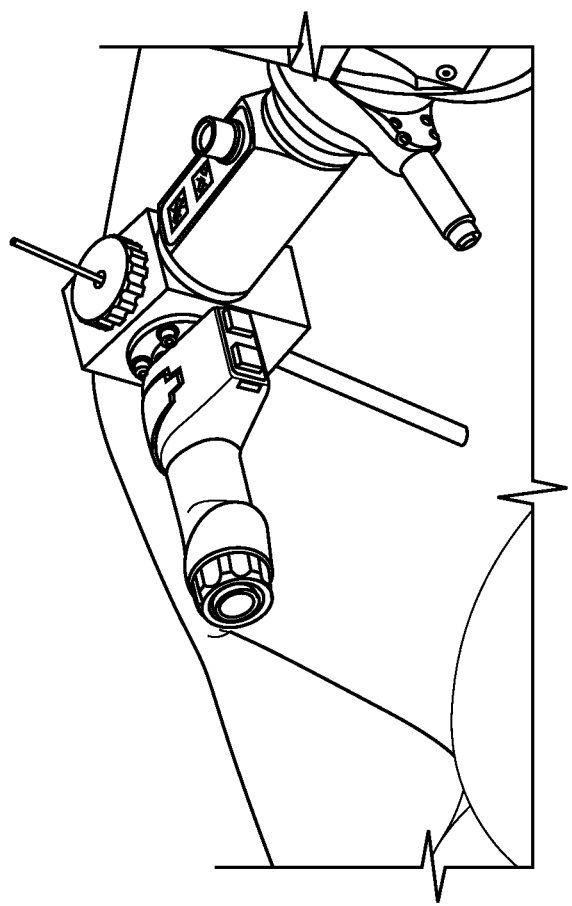

In step 2018 of method 2000, a drill bit is inserted through the drill guide and a hole is drilled in the patient's bone. A lip on the internal surface of the drill guide's guiding shaft may limit the distance the bit can protrude from the guide and thus limit the drilling depth. In certain embodiments, the drill bit is an anti-skiving drill bit in order to ensure the intended trajectory is followed during drilling. Skiving alters the alignment of the drilled hole such that it does not align with the trajectory of the drill guide. Misalignment of the drilled hole makes subsequent surgical steps difficult to follow without complication. FIGS. 25 and 26 show a drill bit guided by a drill guide through an incision site and to a patient's vertebra for drilling a hole.

Figure 13A:
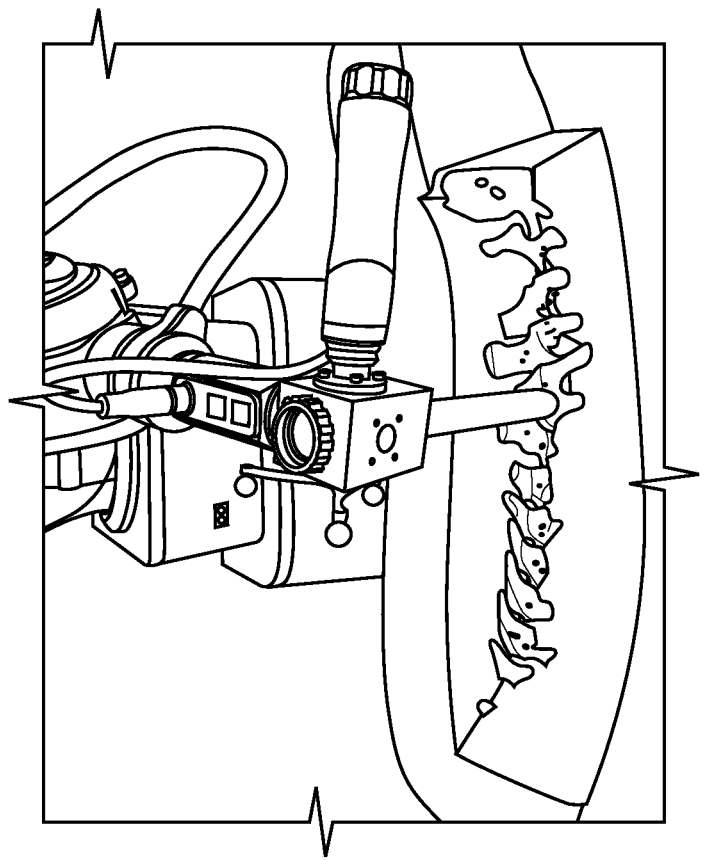
FIG. 13A and FIG. 13B show inserting a master guide into a universal surgical instrument guide, according to an illustrative embodiment of the invention.
Figure 13B:
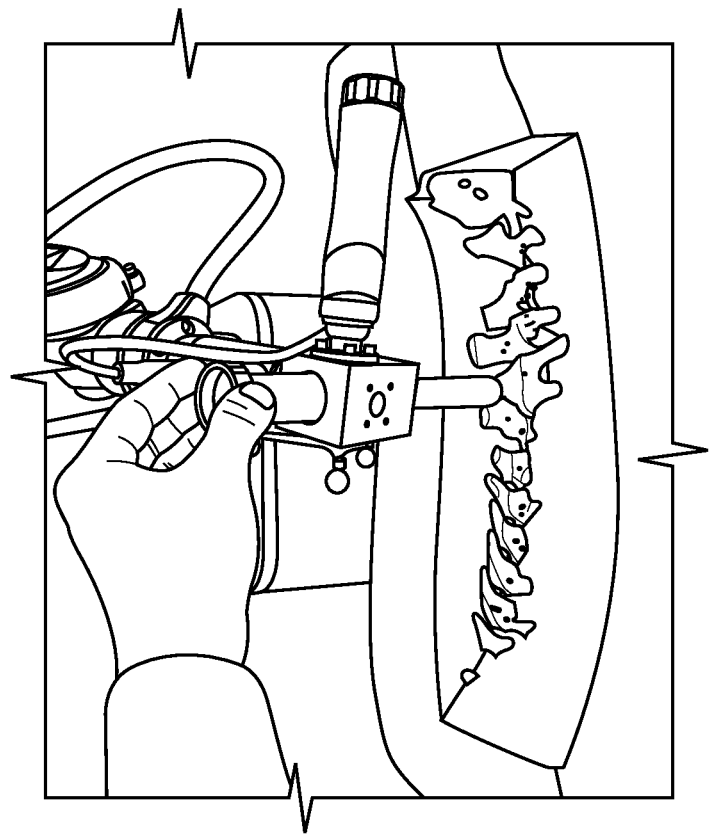
Figure 28:
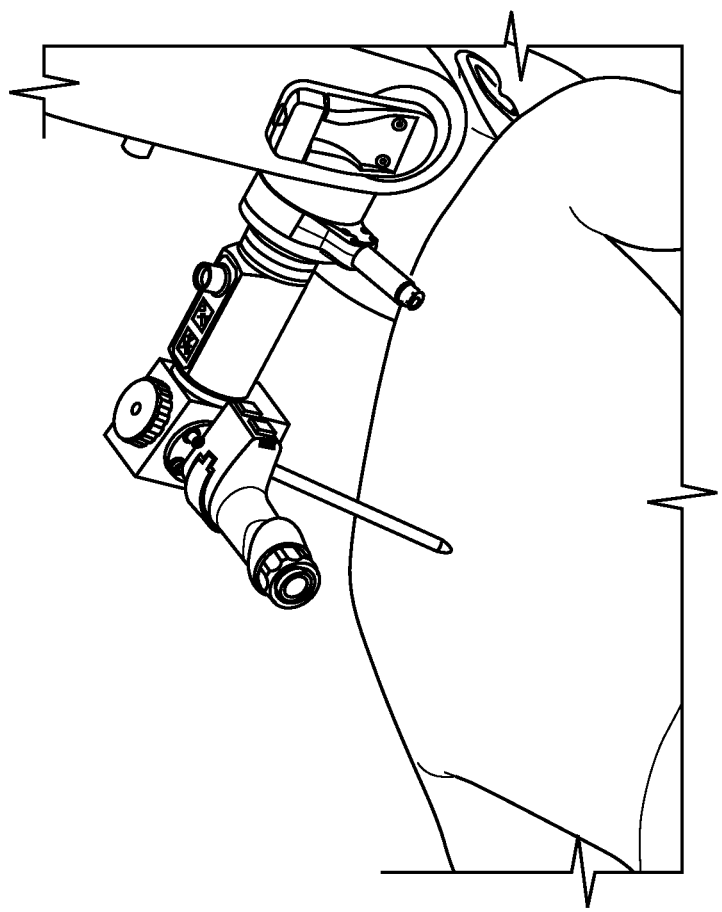
Figure 27:
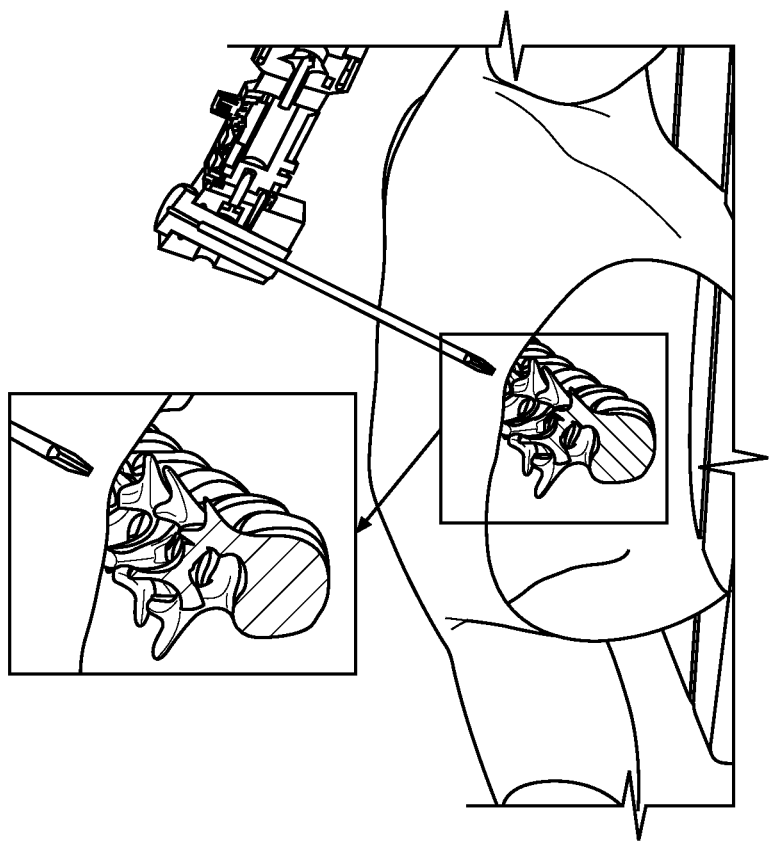
Figure 30:
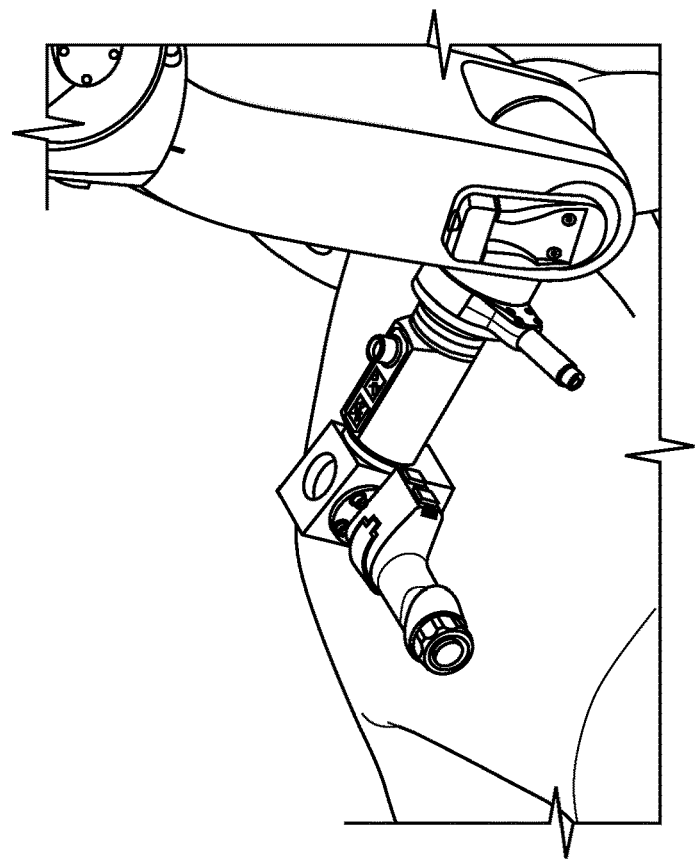
Figure 29:
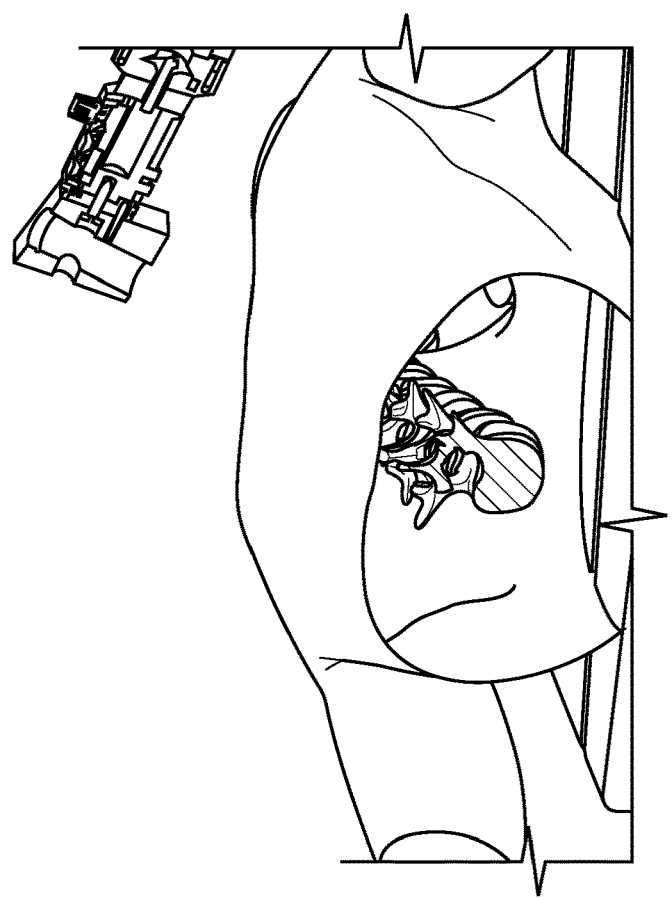
Figure 32:
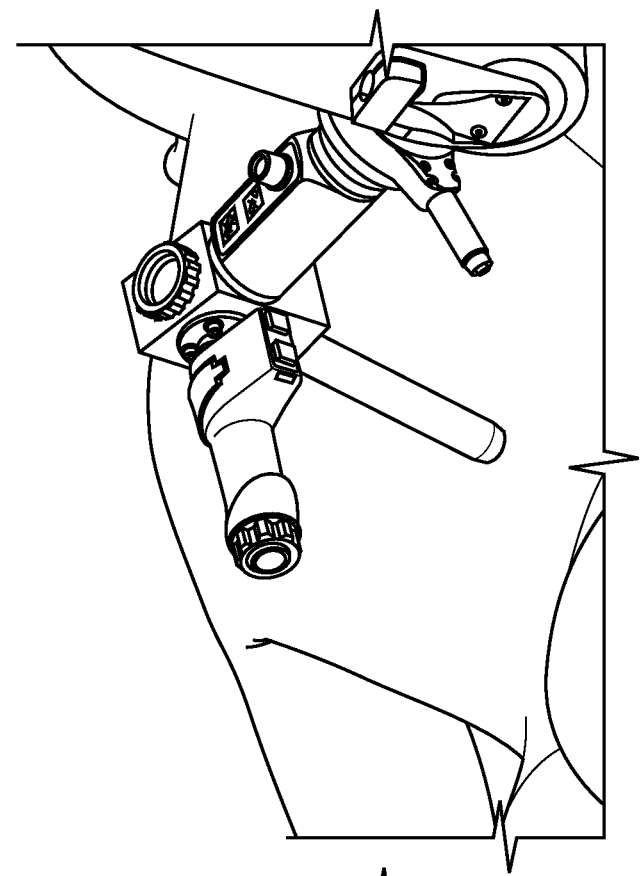
Figure 31:
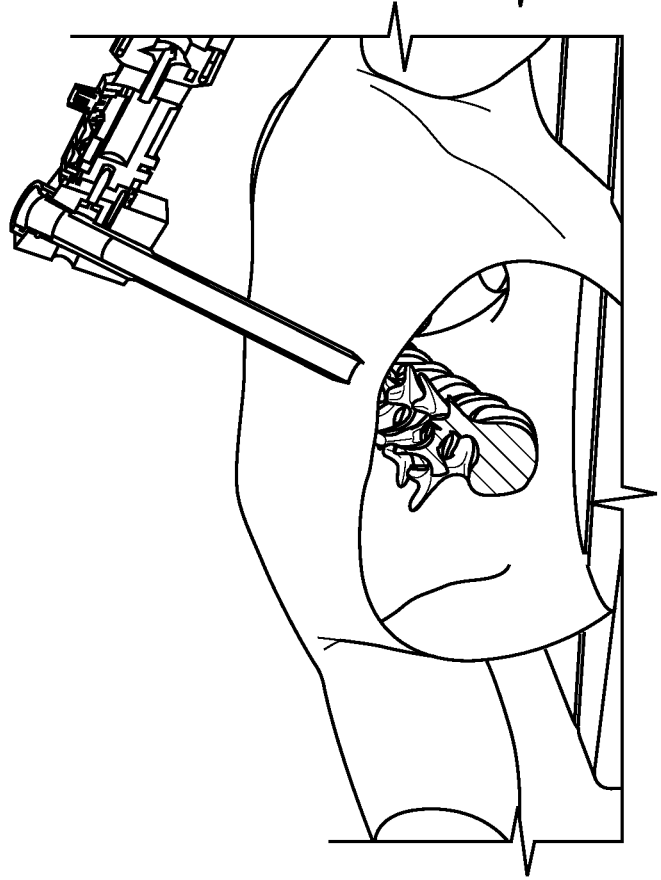

In step 2020 of method 2000, the drill guide is removed and the master guide is inserted into the universal surgical instrument guide. FIGS. 27 and 28 show two illustrations of the drill guide removed from the patient. FIGS. 29 and 30 show two illustrations of the drill guide removed from the universal surgical instrument guide. FIGS. 31 and 32 show two illustrations of a master guide inserted into the universal surgical instrument guide. Note that the orientation and position of the universal surgical instrument guide do not change as the drill guide is removed and master guide is inserted. FIGS. 13A and 13B show a master guide being inserted into a universal surgical instrument guide.

Figure 14:
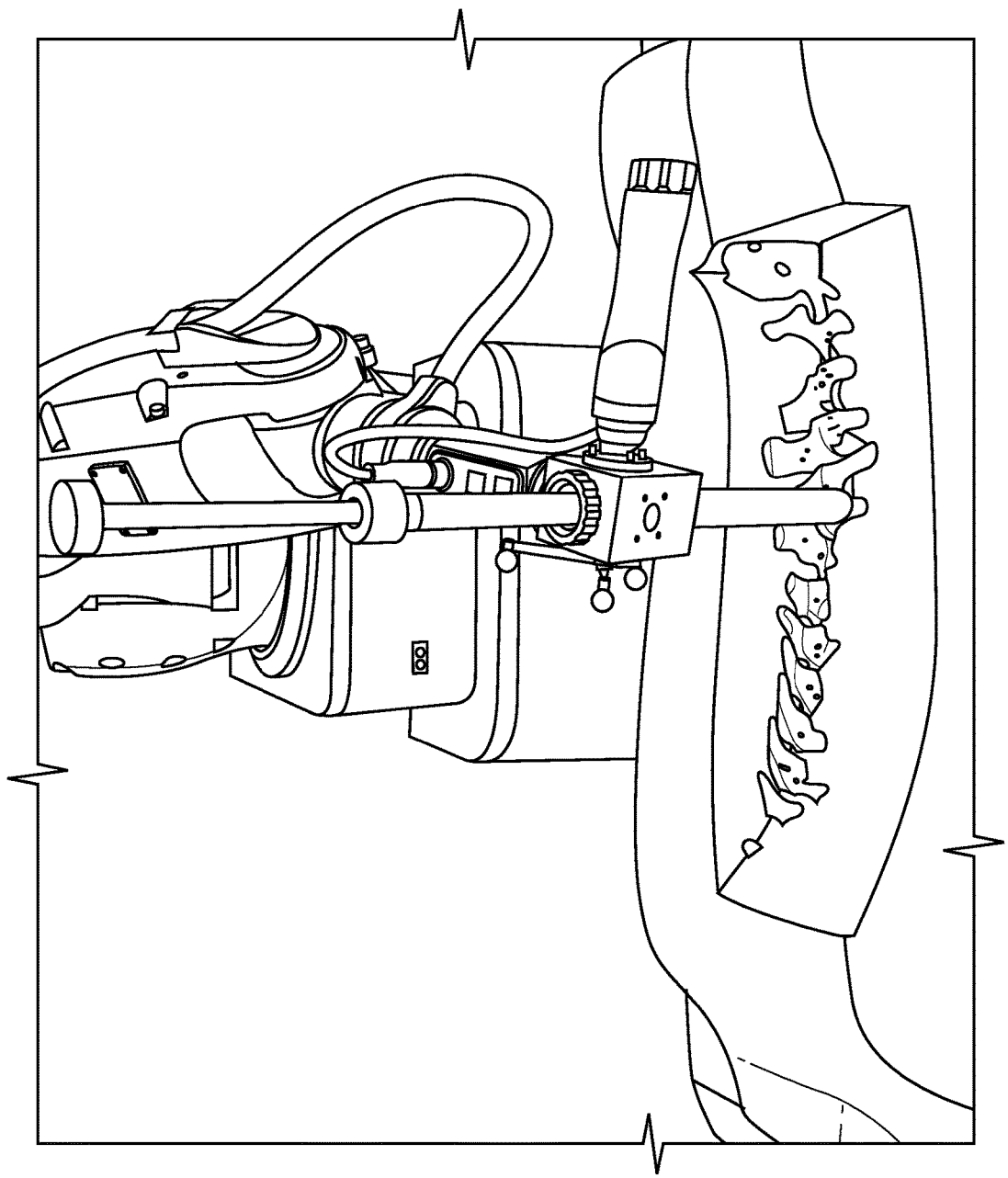
FIG. 14 show inserting a tubular dilator and rod dilator into a master guide, according to an illustrative embodiment of the invention.
Figure 34:
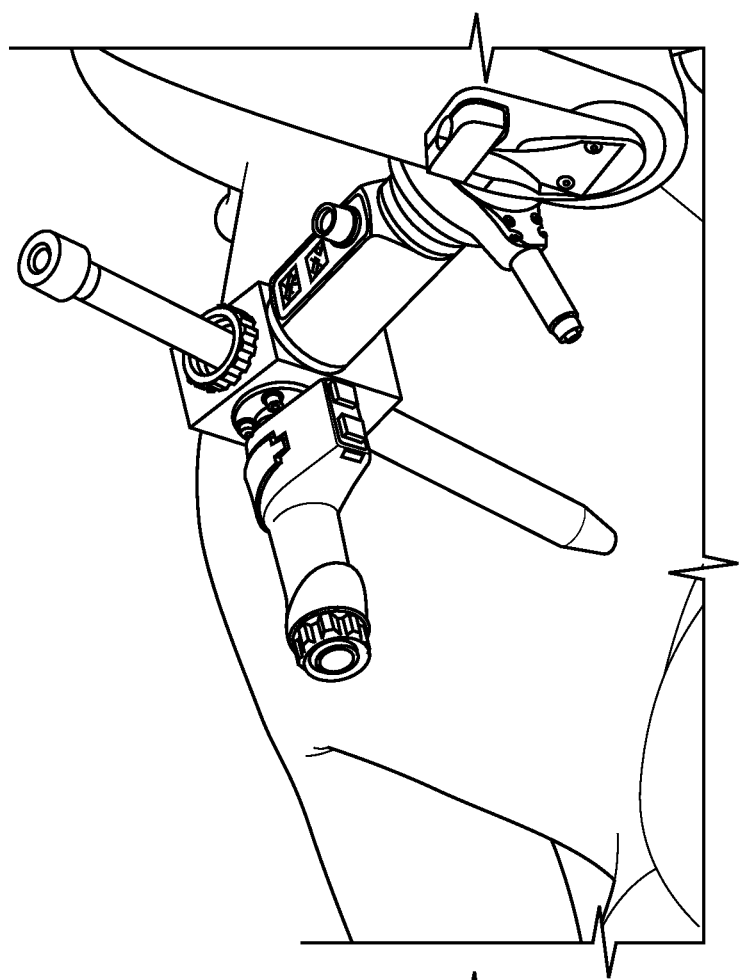
Figure 33:
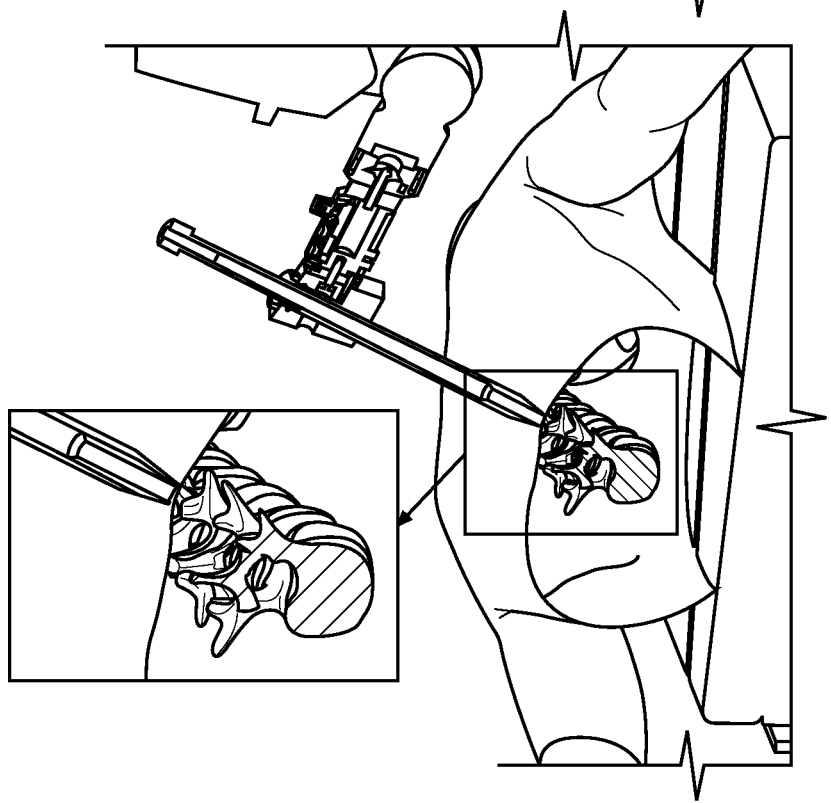
Figures 35, 36:
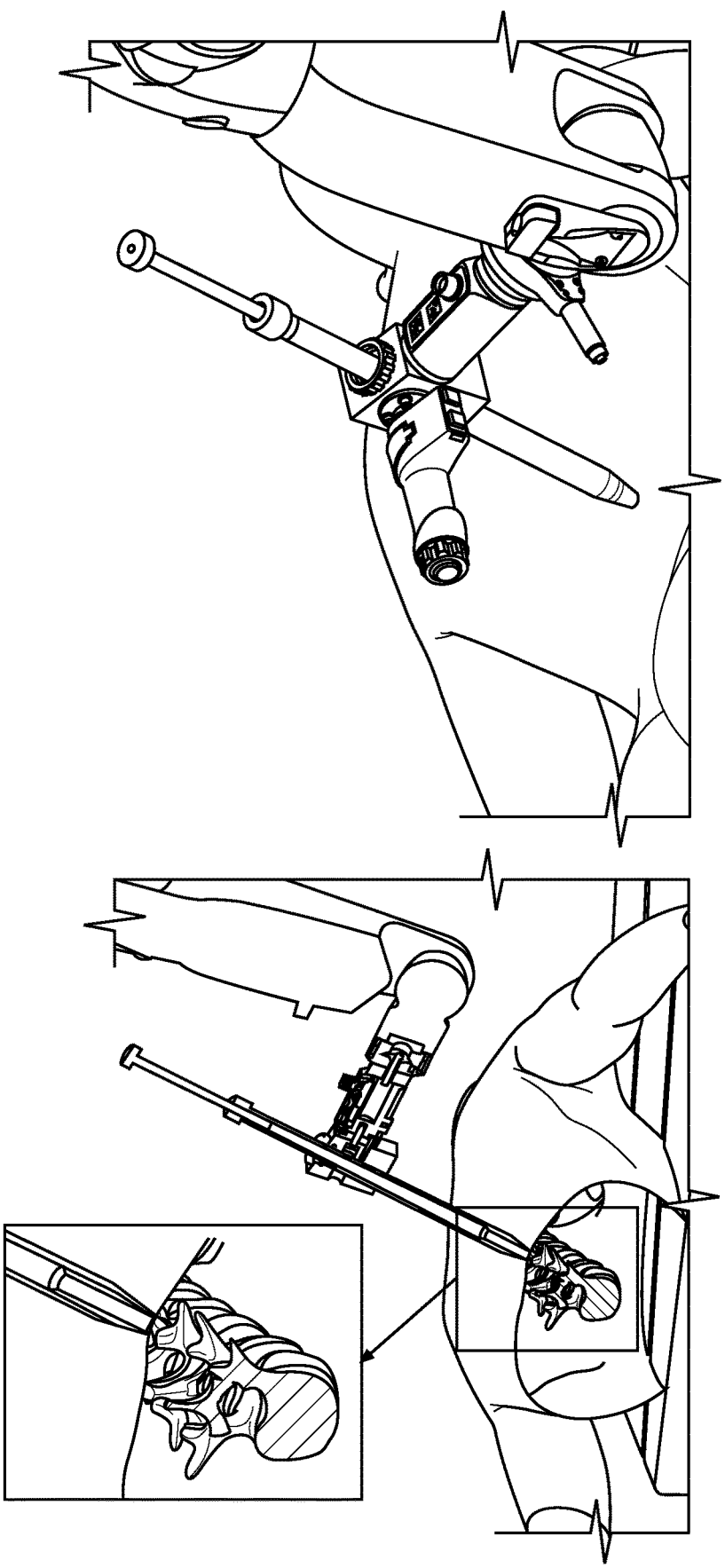
Figures 37, 38:
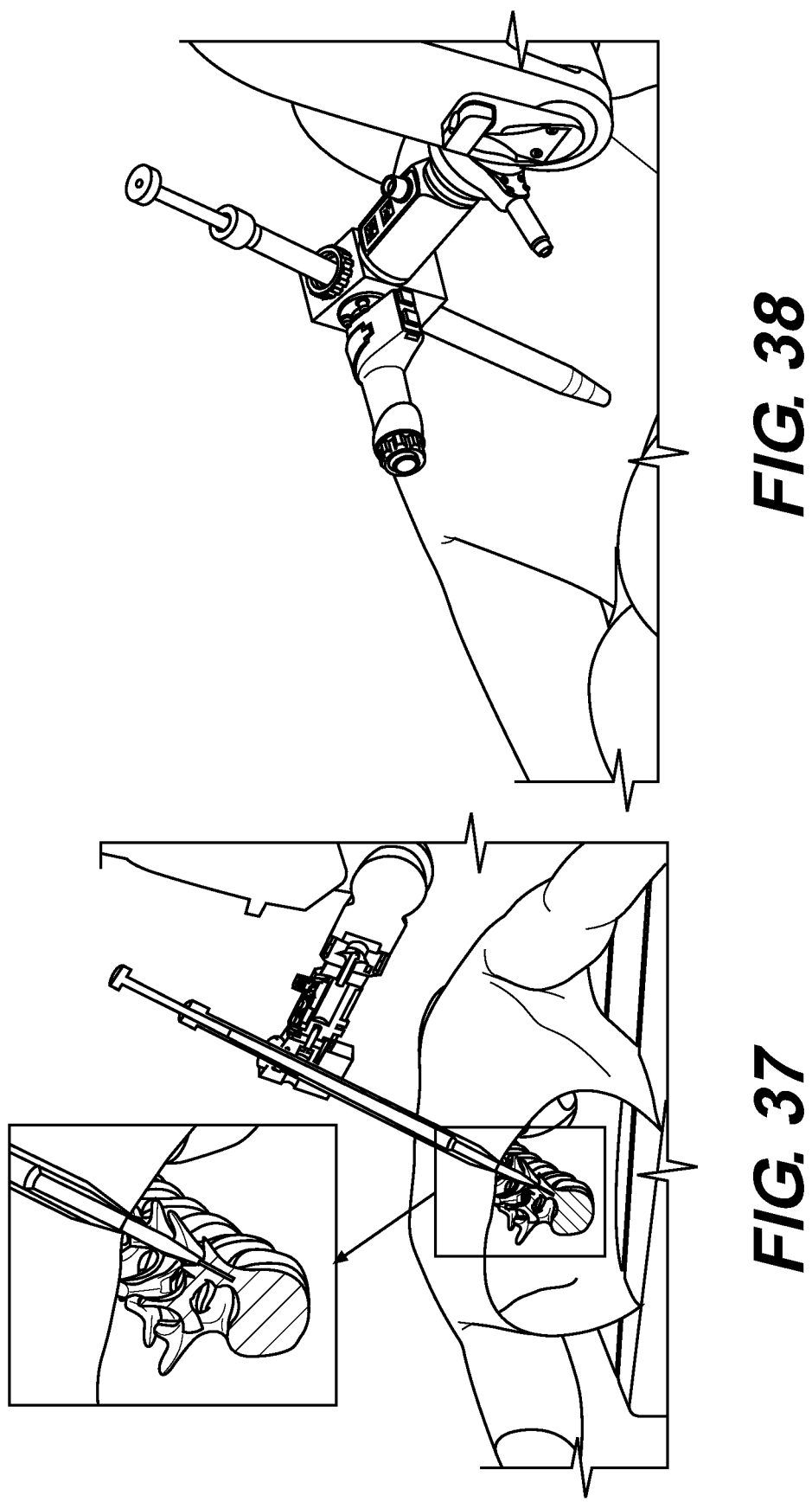
Figure 42:
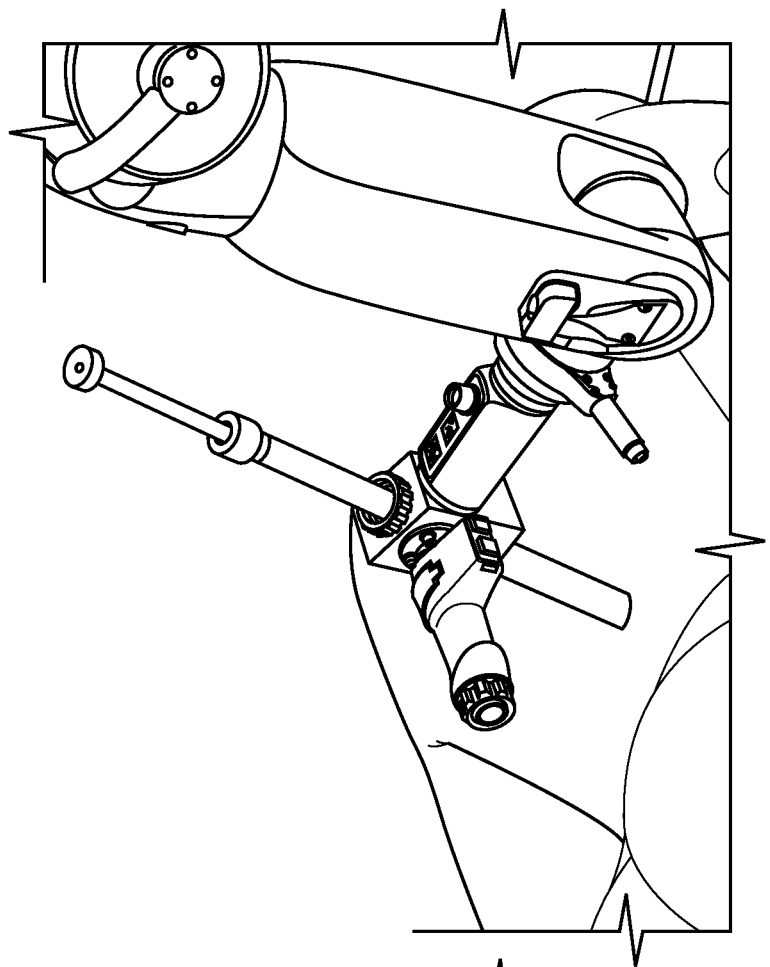
Figure 41:
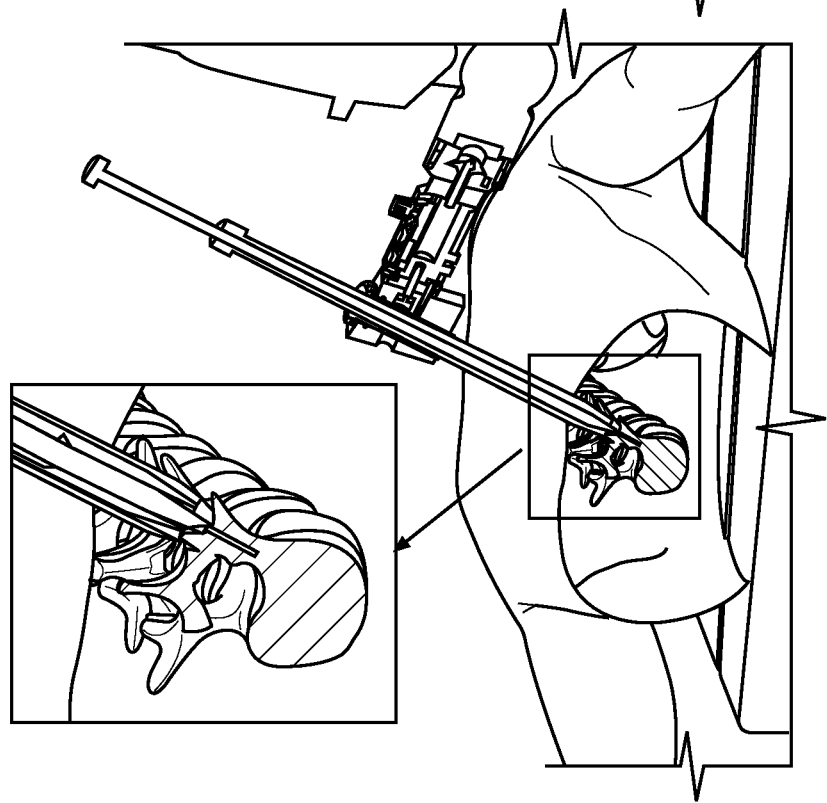
Figure 44:
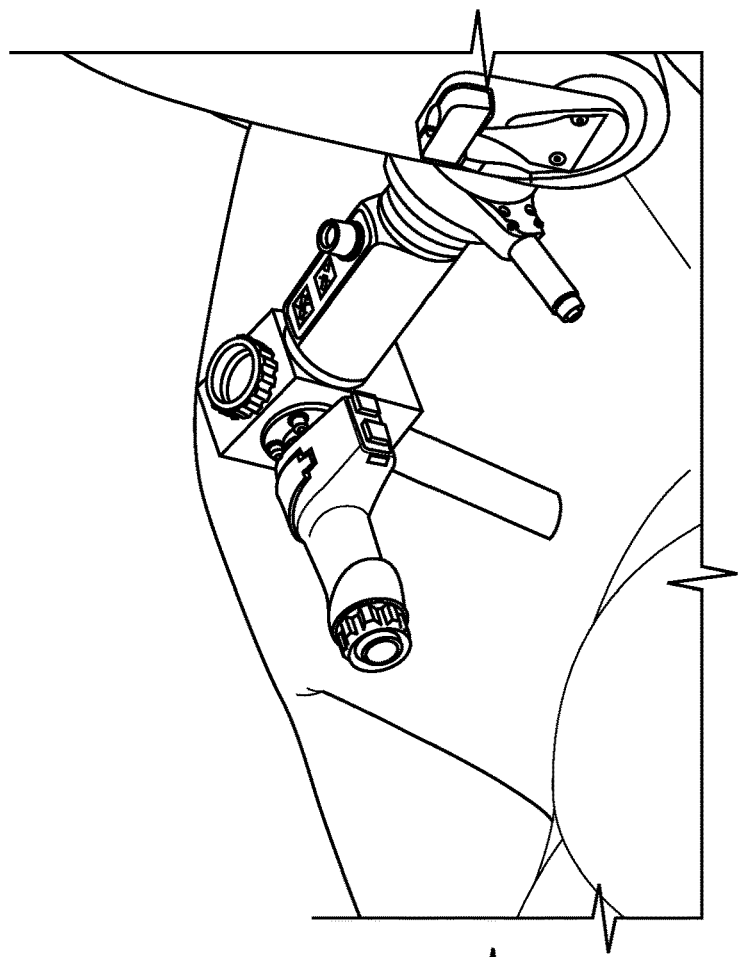
Figure 43:
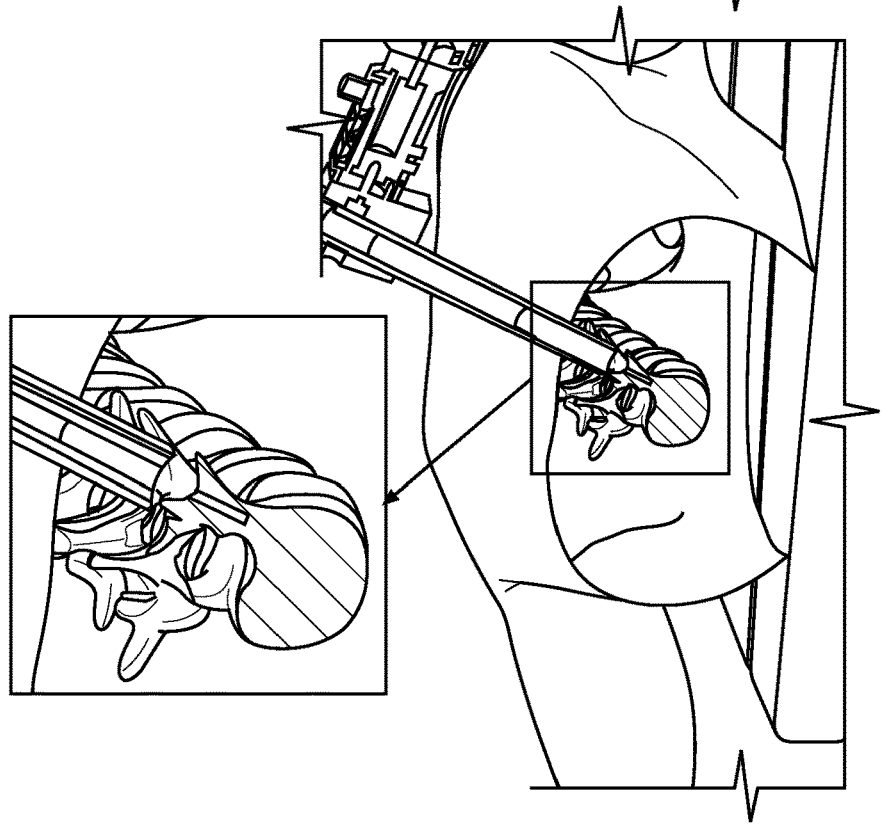

In step 2022 of method 2000, a tubular dilator and rod dilator are inserted into the master guide. The distal end of the master guide (i.e., the tool center point) is located near the patient's skin at the incision site. When inserted, the dilators will rest near the patient's skin until pushed further into the surgical site. FIGS. 33 and 34 show two illustrations of a tubular dilator inserted into the master guide. FIGS. 35 and 36 show two illustrations of a rod dilator inserted into the tubular dilator. FIG. 14 shows a rod dilator inserted in a tubular dilator that has been inserted in a master guide. The surgeon can push rod dilator down to the surgical site at the patient's vertebra to push open the access area around the drilled hole. After pushing the rod dilator down, the tubular dilator can be pushed down. The trajectory of the rod dilator and tubular dilator are maintained due to the orientation of the master guide's guiding shaft. FIGS. 37 and 38 show two illustrations of a rod dilator pushed through an incision to a patient's vertebra. FIGS. 39 and 40 show two illustrations of a tubular dilator pushed through the incision to the patient's vertebra. After the dilators have been pushed to the surgical site, the surgeon can maneuver the robotic arm along the defined trajectory such that the distal end of the master guide's guide shaft resides at the surgical site. FIGS. 41 and 42 show two illustrations of a master guide maneuvered through an incision to a patient's vertebra. Once the master guide is maneuvered to the patient's vertebra, the tubular and rod dilators can be removed. FIGS. 43 and 44 show two illustrations of a master guide located at a patient's vertebra with dilators removed.

Figure 15A:
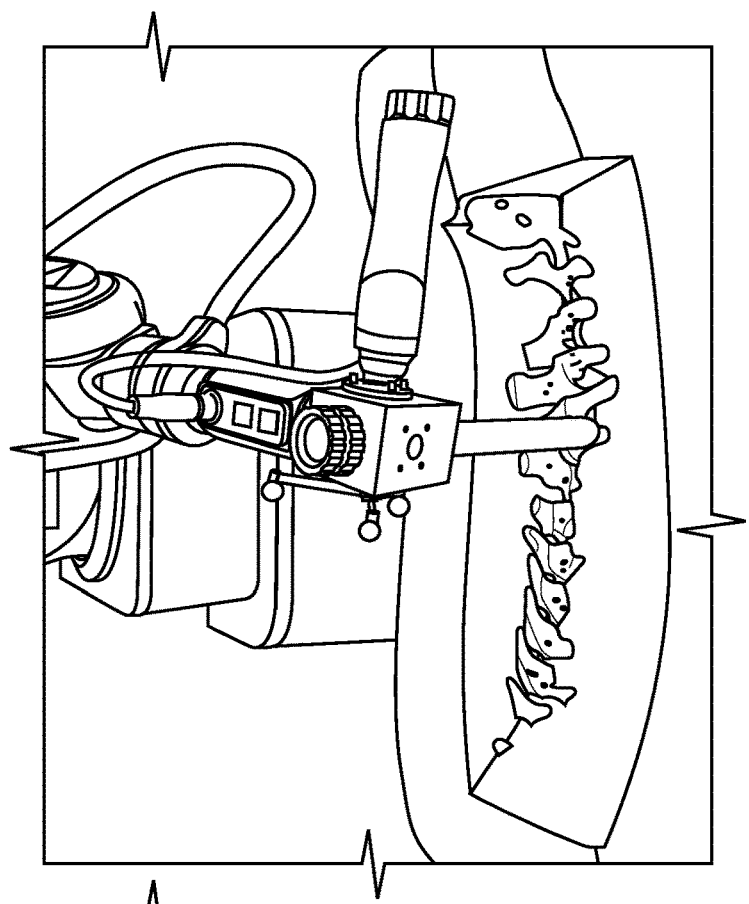
FIG. 15A and FIG. 15B show inserting a surgical tap guide into a master guide, according to an illustrative embodiment of the invention.
Figure 15B:
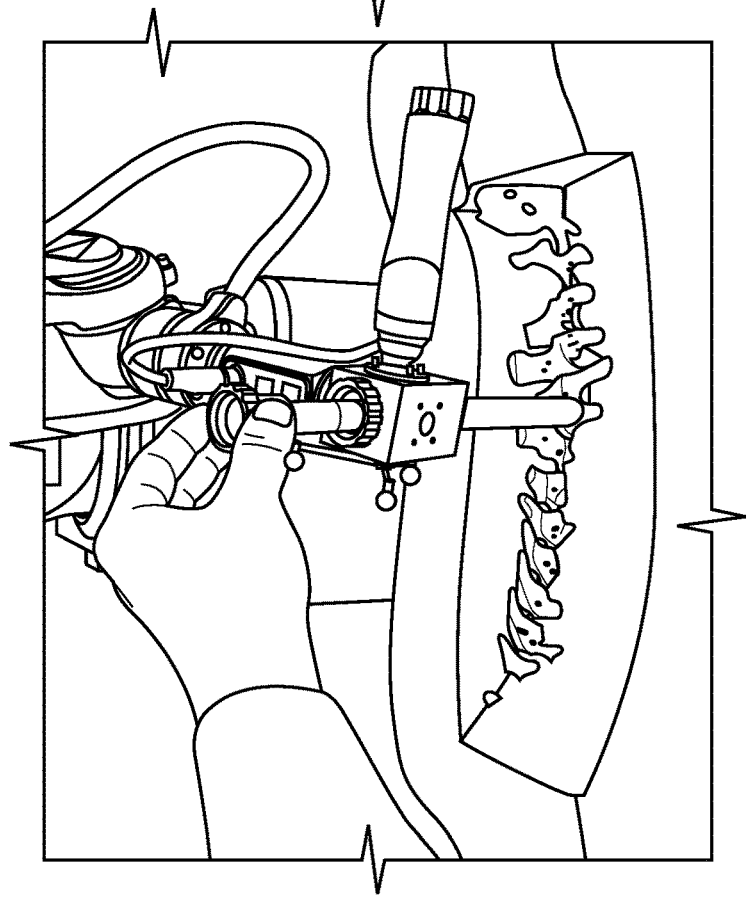
Figure 16B:
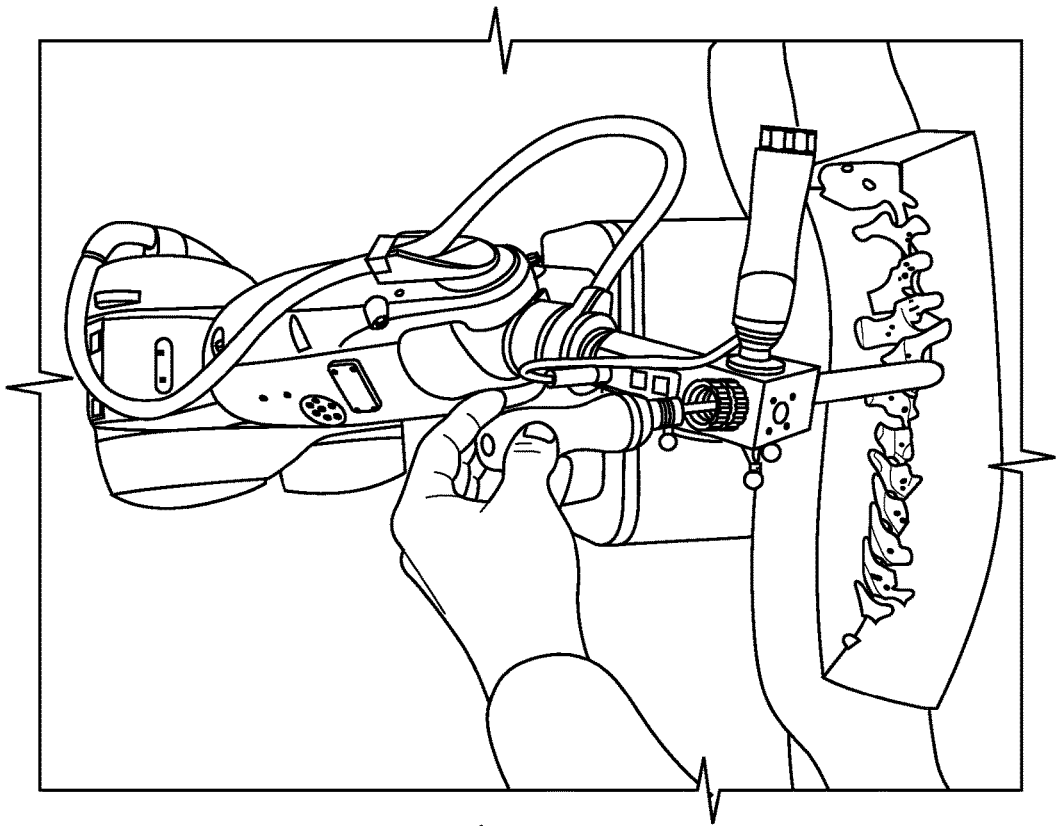
FIG. 16A and FIG. 16B show inserting a tap into a surgical tap guide, according to an illustrative embodiment of the invention.
Figure 16A:
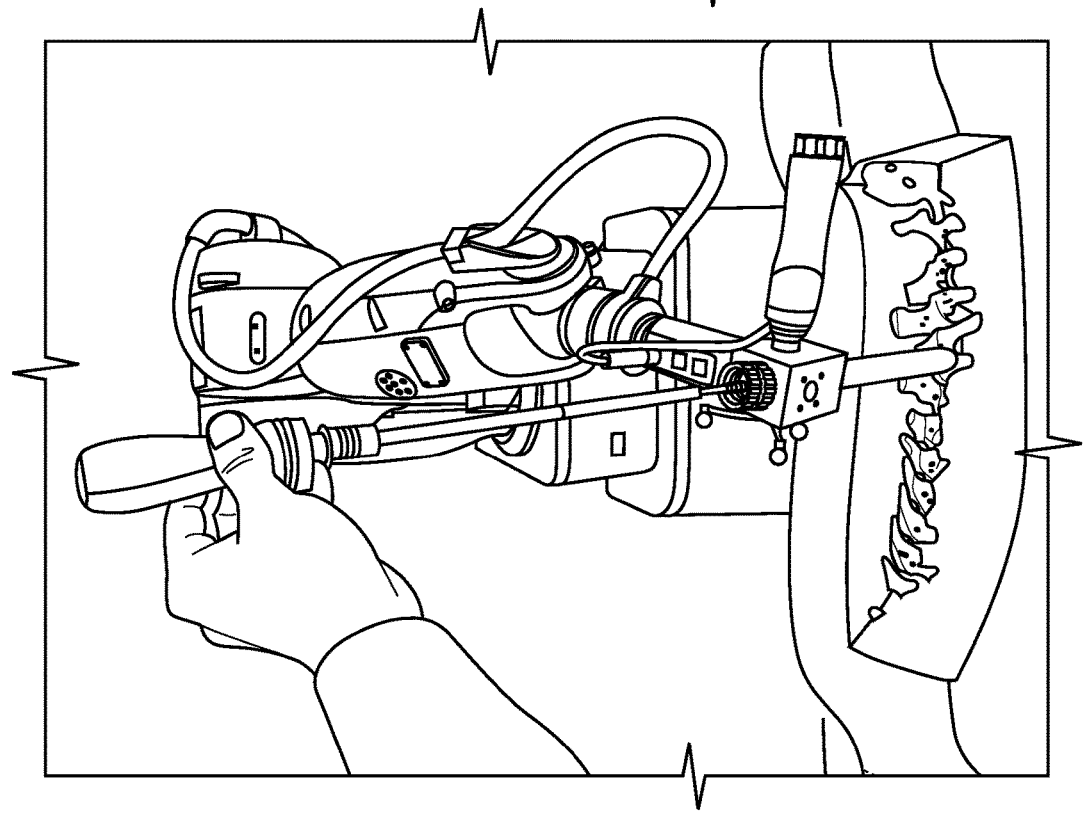
Figure 46:
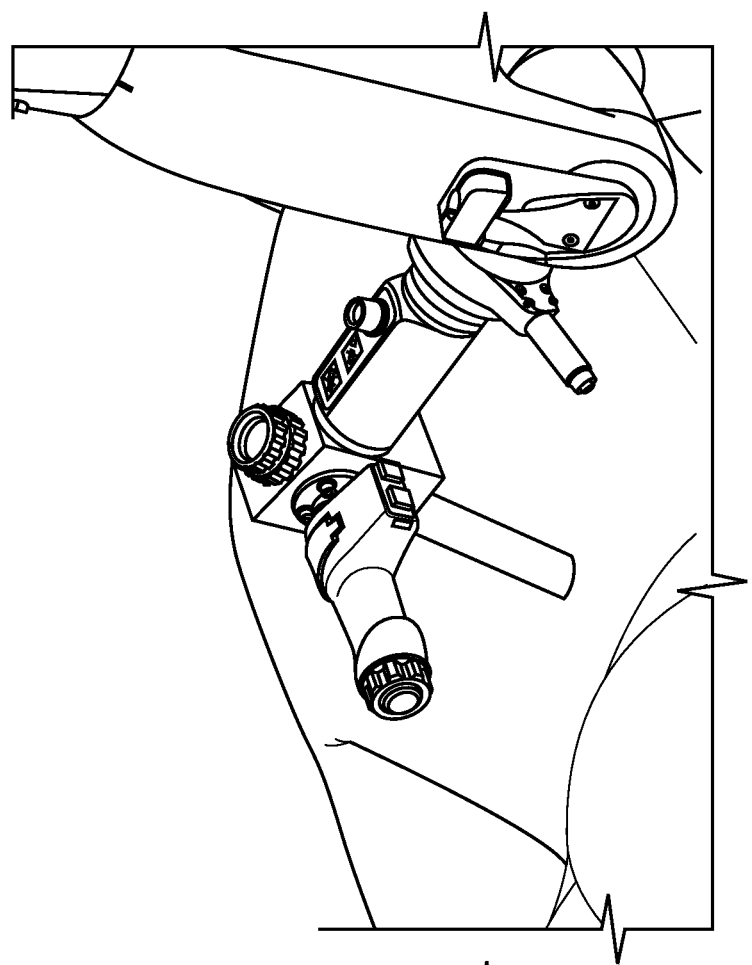
Figure 45:
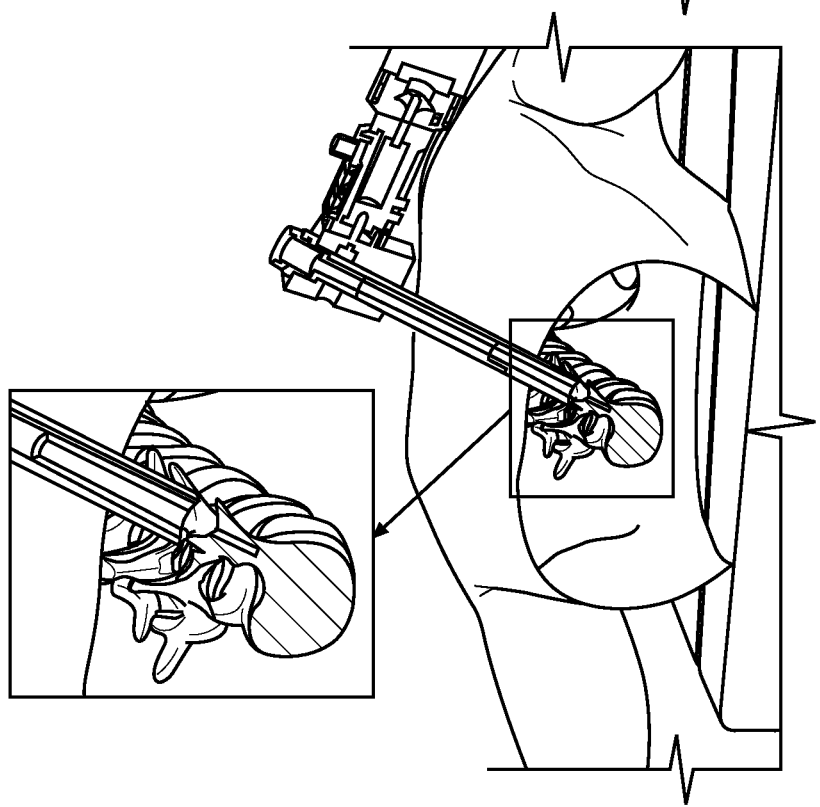
Figure 48:
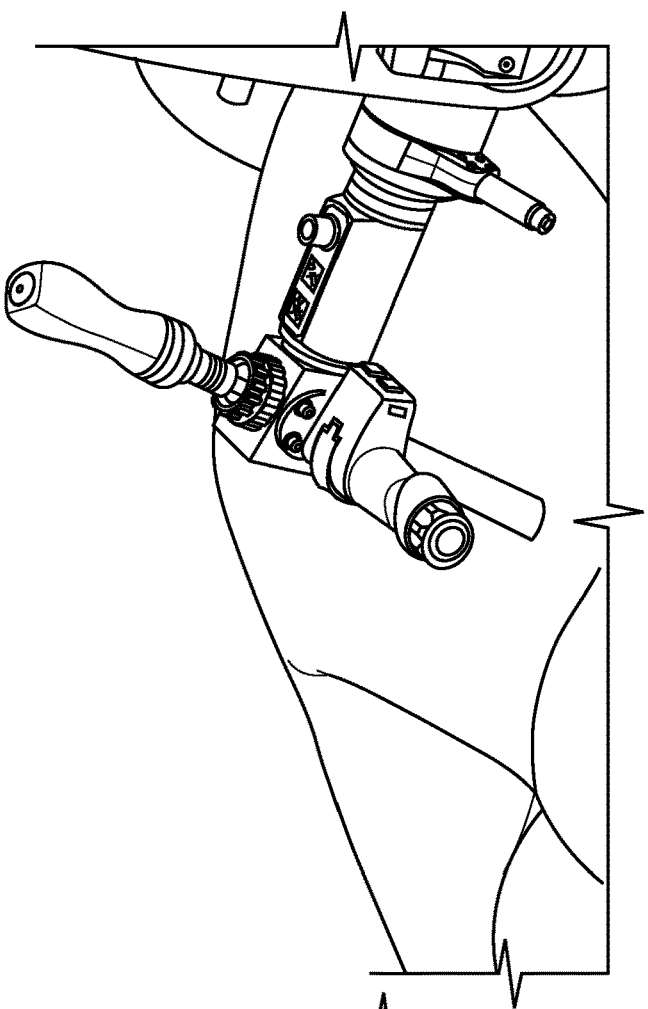
Figure 47:
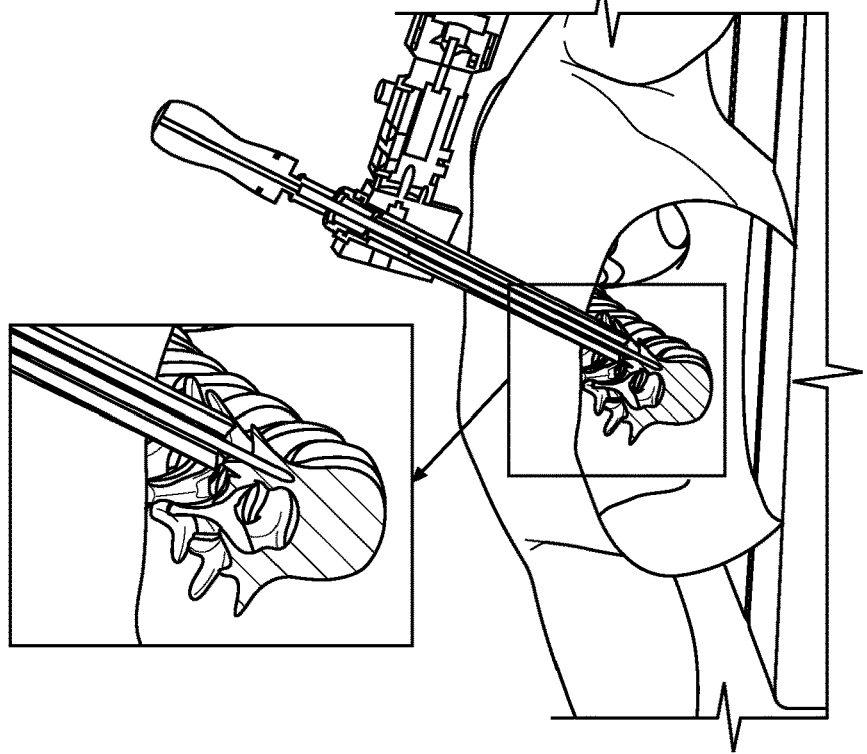

In step 2024 of method 2000, a surgical tap guide is inserted into the master guide and a surgical tap is used to tap the hole drilled earlier in the method. FIGS. 45 and 46 show two illustrations of a surgical tap guide inserted into the master guide (see FIGS. 15A-15B for surgical tap guide during and after insertion). FIGS. 47 and 48 show two illustrations of a surgical tap inserted into the surgical tap guide (see FIGS. 16A-16B for surgical tap during and after insertion). Because the trajectory defined by the universal surgical instrument guide has not changed throughout the procedure, the tap will line up with the hole drilled earlier without the use of any temporary implant (e.g., a k-wire). Once the drilled hole has been tapped, the surgical tap can be removed from the surgical tap guide.

Figure 17B:
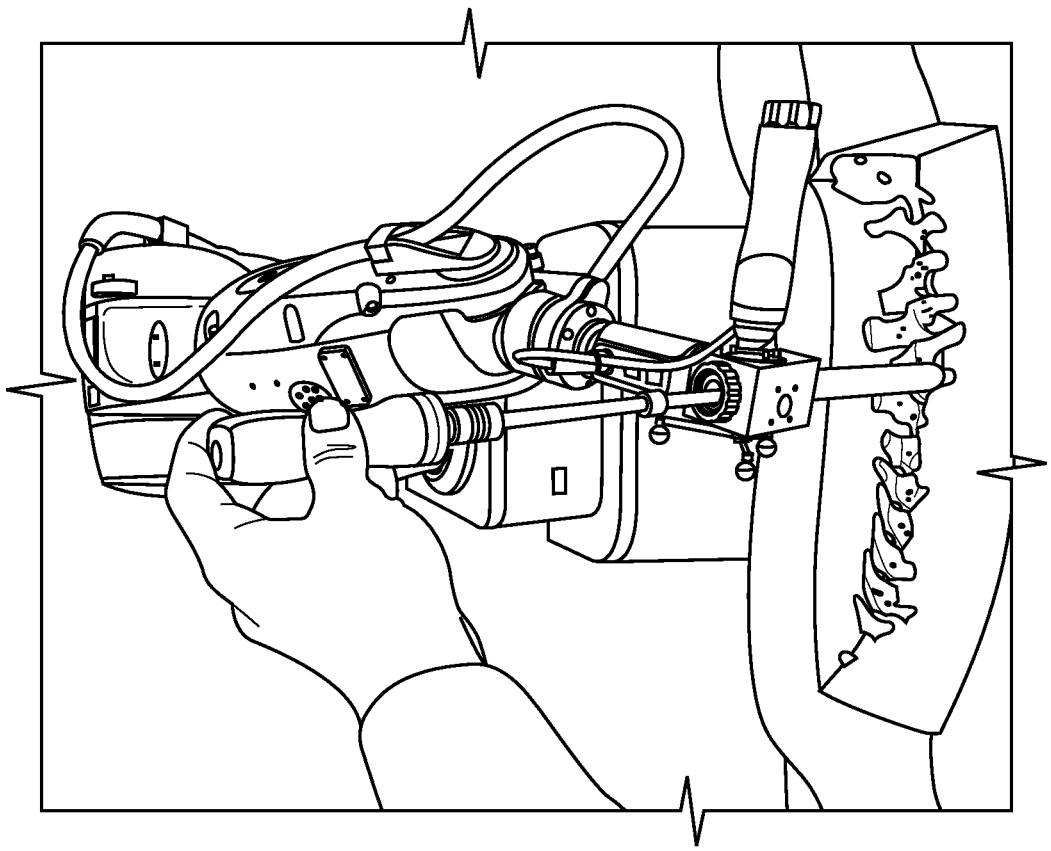
FIG. 17A and FIG. 17B show inserting a screw with releasably attached screw extender attached to a surgical screwdriver into a master guide, according to an illustrative embodiment of the invention.
Figure 17A:
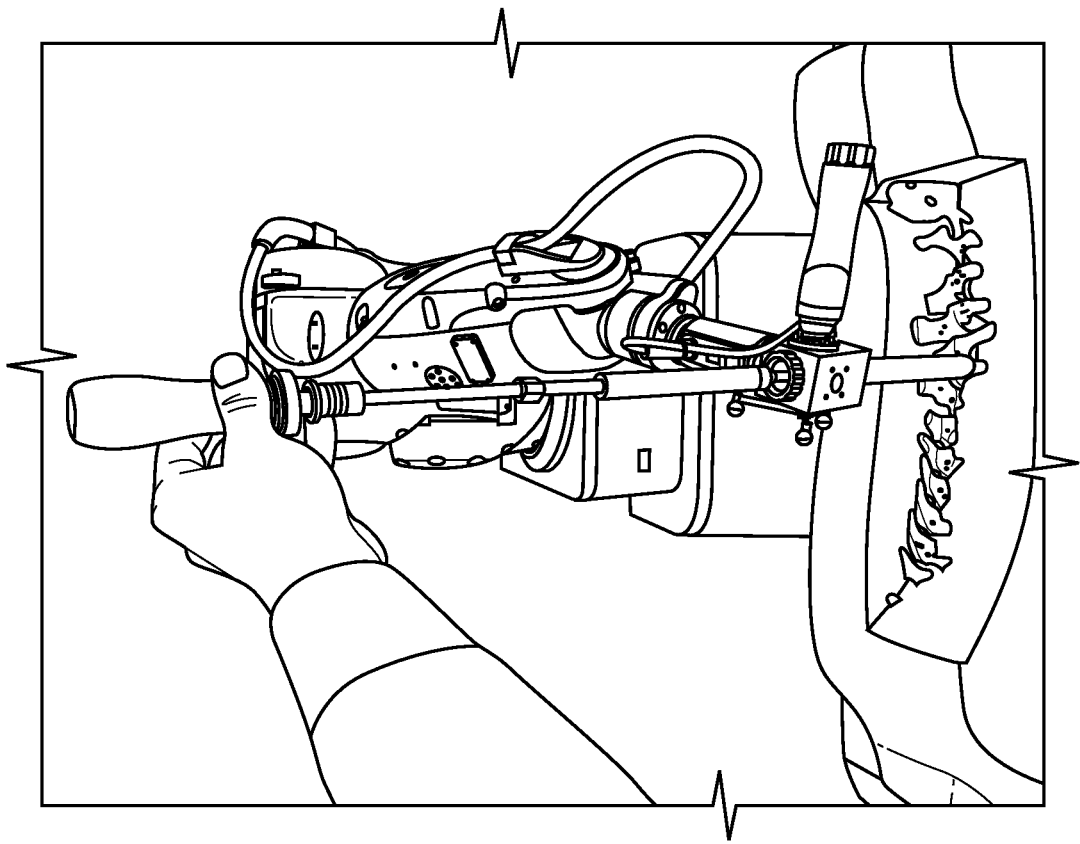
Figure 50:
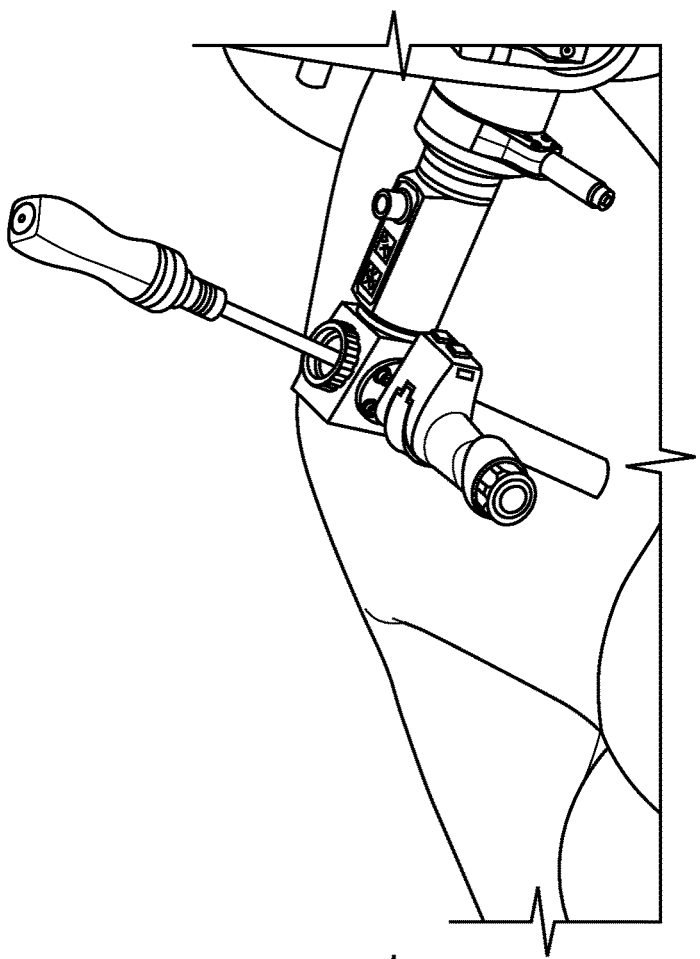
Figure 49:
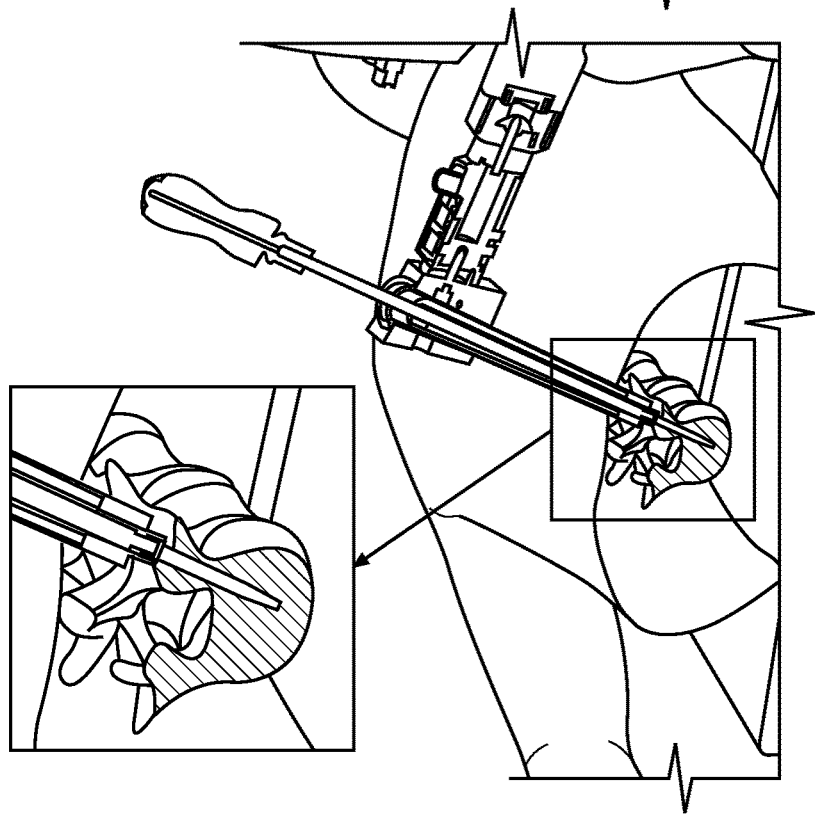

In step 2026 of method 2000, the surgical tap guide is removed from the master guide and a pedicle screw with releasably attached extender and screwdriver is inserted in the master guide. The screw will protrude slightly from the master guide and be aligned with the tapped hole in the patient's vertebra. FIGS. 49 and 50 show two illustrations of a screw being implanted in the tapped hole in the patient's vertebra (see FIGS. 17A-17B for screw, extender, and screwdriver assembly during and after insertion). The screwdriver is positioned to engage the screw's head. The screw extender is releasably attached to the screw such that the screw extender can be used to assist in additional procedures that occur after method 2000. In step 2028, the screw is implanted in the patient's vertebra by turning the screwdriver. Then, the screw driver is removed from the pedicle screw with extender assembly.

Figure 51:
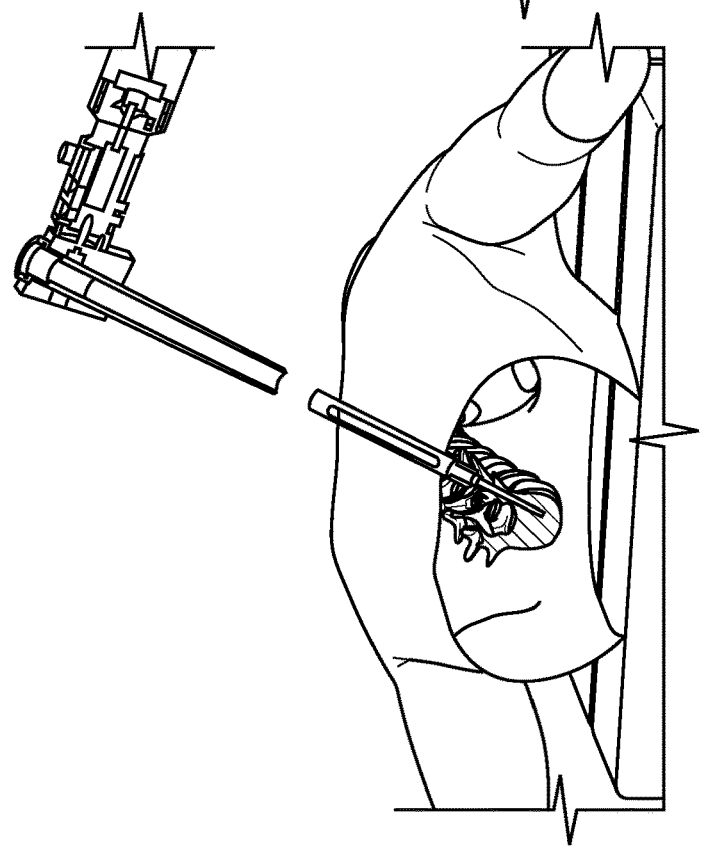
Figure 52:
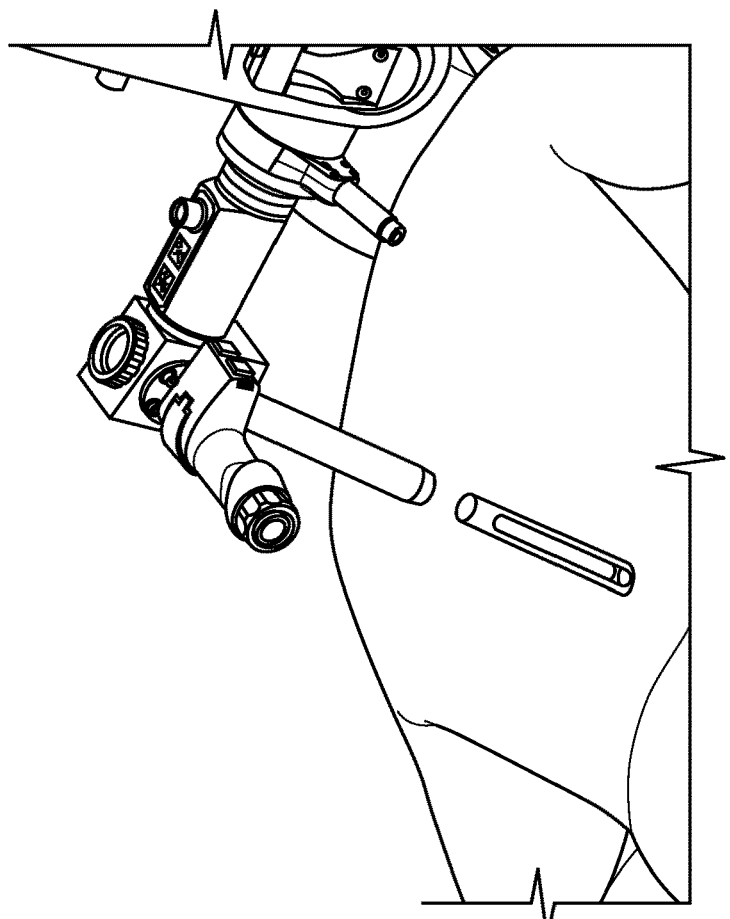

Finally, method 2000 ends in step 2030, where the robotic arm may be moved along its trajectory-mode limited axis away from the surgical site. The master guide will translate along the length of the screw extender until the master guide is separated from the screw extender. The use of the trajectory mode ensures that the screw extender is not disturbed during removal of the master guide. FIGS. 51 and 52 show two illustrations of the robotic arm after it is maneuvered away from the screw extender. Note that the orientation of the master guide and the screw extender are the same. Once the robotic arm is free from a surgical implant such that future motion need not disturb the implant, the trajectory mode can be exited and the robotic arm can be maneuvered freely as desired by the surgeon. The procedure may be complete or additional screws or other implants may be implanted.

When desired by a surgeon, method 2000 may be modified for use with a k-wire. A surgeon can proceed through the steps of method 2000 through step 2018. Then, after the hole has been drilled following a precise trajectory, the drill bit is removed and a k-wire is placed in the drilled hole with trajectory guidance from the drill guide. The drill guide may then be removed from the patient by maneuvering along the long axis of the k-wire until it is separated from the k-wire. The surgical procedure can then proceed with use of cannulated surgical instruments following methods known in the art. Using a universal surgical instrument system to place a k-wire ensures that the k-wire is correctly implanted within the drilled hole along the desired orientation, thus reducing complications that may arise from a misplaced or misoriented k-wire.

For some surgeons, it is important to be able to cross-check a drilled trajectory after drilling the hole. Integrating this function with the universal instrument guide disclosed herein can improve confidence of a surgeon. This function can be implemented using a navigated dilator which goes around a K-wire placed just after drilling. Once the trajectory is verified, the K-wire can be removed and the procedure can continue with the master guide as described herein.

Specifically, a surgeon can proceed through the steps of method 2000 through step 2018. Then, after the hole has been drilled following a precise trajectory, the drill bit is removed and a k-wire is placed in the drilled hole with trajectory guidance from the drill guide. Next, the drill guide is removed from universal surgical instrument guide. A navigated dilator (e.g., a tube with an internal diameter sufficient to accommodate the external diameter of a k-wire and navigation members that can be tracked and visualized by navigation systems) is inserted along the k-wire and pushed down to surgical site. In certain embodiments, the navigated dilator can go through the universal surgical instrument guide without being guided by it. As soon as navigated dilator is in contact with patient, the drilled trajectory can be cross-checked. Thereafter, the navigated dilator is removed from surgical site along the k-wire and then the k-wire is removed from patient. Method 2000 can then continue from step 2020 with insertion of master guide in universal instrument guide.

It is understood that the method described in FIG. 20 is exemplary. Many surgical procedures require the use of multiple surgical instruments following the same (precise) trajectory such that they benefit from the use of a universal surgical instrument guide (and accompanying universal surgical instrument system) with a robotic surgical system. Other orthopedic and non-orthopedic methods are equally adapted to utilize a universal surgical instrument guide attached to a robotic arm. Other surgeries contemplated for use with a universal surgical instrument guide and/or universal surgical instrument system include, but are not limited to, orthopedic procedures, ENT procedures, and neurosurgical procedures. Such procedures may be performed using an open, percutaneous, or MIS approach.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Having described certain implementations of methods, systems, and apparatus for performing surgery along precise trajectories without surgical instrument realignment it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A universal surgical instrument guide for accommodating surgical instruments to facilitate precise positioning of the surgical instruments using a robotic surgical system, the universal surgical instrument guide comprising:
a body arranged to be mechanically coupled to a robotic arm of the robotic surgical system, the body comprising:
a first channel comprising an interior surface sized and shaped to accommodate a fastener that securely attaches the body directly or indirectly to the robotic arm of the robotic surgical system,
a second channel having an interior surface shaped and sized to accommodate a portion of a surgical instrument,
wherein the second channel comprises a first opening, wherein a portion of the second channel adjacent to the first opening is threaded such that when the surgical instrument is inserted in the second channel, threads of the threaded portion of the second channel engage threads on the surgical instrument to secure the surgical instrument to the universal surgical instrument guide, and
wherein the second channel defines an axis such that, when the surgical instrument is inserted into the universal surgical instrument guide, movement of the surgical instrument is constrained along the axis within the universal surgical instrument guide; and
an opening sized and shaped to receive a navigation marker used by a navigation camera to track the position of the surgical instrument; and
one or more alignment members extending from the body such that the one or more alignment members are configured to engage one or more openings in the robotic arm,
wherein an axis along a length of the first channel and an axis along a length of the second channel are on a common plane.

2. The universal surgical instrument guide of claim 1 further comprising a handle support member, wherein the handle support member is attached to the body.

3. The universal surgical instrument guide of claim 1, wherein the navigation marker comprises a plurality of navigation marker elements wherein the plurality of navigation marker elements are used to triangulate a position of the universal surgical instrument guide.

4. The universal instrument guide of claim 1, wherein the body comprises a threaded bushing having an interior surface.

5. The universal instrument guide of claim 4, wherein the interior surface of the threaded bushing defines an axis parallel to an axis defined by the interior surface of the first channel and the interior surface of the threaded bushing is threaded such that the threads on the fastener engage the threads on the threaded bushing as the fastener is inserted through the threaded bushing.

6. The universal surgical instrument guide of claim 1, wherein the fastener comprises:
   a tip on a proximate end of a screw body;
   a head on a distal end of the screw body; and
   threads along a portion of the screw body.

7. The universal surgical instrument guide of claim 6, wherein the threads along the portion of the fastener are along a portion of the fastener closest to the tip of the tightening screw.

8. The universal surgical instrument guide of claim 7, wherein the portion of the fastener closest to the head is smooth such that the fastener is loosely held in place by the threaded bushing when the fastener is fully inserted into the threaded bushing.

9. The universal surgical instrument guide of claim 1, wherein the surgical instrument has a hollow tubular structure sized and shaped to receive a surgical tool selected from the group consisting of: a drill bit, a tubular dilator, a rod dilator, a surgical tap, a screw driver, a screw extender, and an awl.

10. The universal surgical instrument guide of claim 1, wherein the surgical instrument is a drill guide.

11. The universal surgical instrument guide of claim 1, wherein the surgical instrument is a drill bit and the drill bit is an anti-skiving drill bit.

12. The universal surgical instrument guide of claim 1, wherein the surgical instrument is a master guide.

13. The universal surgical instrument guide of claim 1, wherein the robotic surgical system is for use in a member selected from the group consisting of: spinal surgery, ENT surgery, neurosurgery, and orthopedic surgery.

14. The universal surgical instrument guide of claim 1, wherein the axis along the length of the first channel and the axis along the length of the second channel are perpendicular.

* * * * *